US007960434B2

(12) United States Patent
Turkson et al.

(10) Patent No.: US 7,960,434 B2
(45) Date of Patent: Jun. 14, 2011

(54) SMALL MOLECULE INHIBITORS OF STAT3 WITH ANTI-TUMOR ACTIVITY

(75) Inventors: James Turkson, Orlando, FL (US); Said M. Sebti, Tampa, FL (US); Wayne Guida, Saint Petersburg, FL (US); Man Lun Yip, Monrovia, CA (US); Nicholas J. Lawrence, Tampa, FL (US); Harshani Lawrence, Tampa, FL (US); Benjamin Greedy, Somerset (GB)

(73) Assignees: University of South Florida, Tampa, FL (US); University of Central Florida Research Foundation, Inc., Orlando, FL (US); H. Lee Moffitt Cancer Center & Research Institute, Tampa, FL (US)

( * ) Notice: Subject to any disclaimer, the term of this patent is extended or adjusted under 35 U.S.C. 154(b) by 735 days.

(21) Appl. No.: 11/805,217

(22) Filed: May 21, 2007

(65) Prior Publication Data
US 2009/0069420 A1    Mar. 12, 2009

Related U.S. Application Data

(60) Provisional application No. 60/801,750, filed on May 19, 2006.

(51) Int. Cl.
*A01N 41/02* (2006.01)
*A61K 31/255* (2006.01)
*A01N 37/18* (2006.01)
*A61K 31/165* (2006.01)

(52) U.S. Cl. ........................................ 514/518; 514/617
(58) Field of Classification Search .................. 514/518, 514/617
See application file for complete search history.

(56) References Cited

U.S. PATENT DOCUMENTS 6,187,775 B1 *   2/2001   Michejda et al. ......... 514/253.02
2007/0032418 A1 *  2/2007   Shapiro et al. .................. 514/12

FOREIGN PATENT DOCUMENTS
WO    WO 98/12201    3/1998
WO    WO 00/44774    8/2000

OTHER PUBLICATIONS

Song et al. Oncogene, 2003, vol. 22, pp. 4150-4165.*
Chen et al. J. of Med. Chem. 1978, vol. 21, No. 9, pp. 868-874.*
Becker, et al., "Three-dimensional structure of the Stat3b homodimer bound to DNA" *Nature*, 1998, pp. 145-151, vol. 394.
Blaskovich, et al., "Discovery of JSI-124 (Cucurbitacin I), a Selective Janus Kinase/Signal Transducer and Activator of Transcription 3 Signaling Pathway Inhibitor with Potent Antitumor Activity against Human and Murine Cancer Cells in Mice1" *Cancer Res.*, 2003, pp. 1270-1279, vol. 63.
Bowman, et al., "STATs in oncogenesis" *Oncogene*, 2000, pp. 2474-2488, vol. 19.
Bromberg, et al., "The role of STATs in transcriptional control and their impact on cellular function" *Oncogene*, 2000, pp. 2468-2473, vol. 19.
Bromberg, J. "Signal transducers and activators of transcription as regulators of growth, apoptosis and breast development" *Breast Cancer Res.*, 2000, pp. 86-90, vol. 2.
Bromberg, et al., "Stat3 as an Oncogene" *Cell*, 1999, pp. 295-303, vol. 98.
Buettner, et al., "Activated STAT Signaling in Human Tumors Provides Novel Molecular Targets for Therapeutic Intervention" *Clin. Cancer Res.*, 2002, pp. 945-954, vol. 8.
Catlett-Falcone, et al., "Constitutive Activation of Stat3 Signaling Confers Resistance to Apoptosis in Human U266 Myeloma Cells" *Immunity*, 1999, pp. 105-115, vol. 10.
Darnell, "Validating Stat3 in cancer therapy" *Nat Med.*, 2005, pp. 595-596, vol. 11.
Darnell, "Transcription Factors As Targets for Cancer Therapy" *Nat. Rev. Cancer*, 2002, pp. 740-749, vol. 2.
Friesner, et al., "Glide: A New Approach for Rapid, Accurate Docking and Scoring. 1. Method and Assessment of Docking Accuracy" *J. Med. Chem.*, 2004, pp. 1739-1749, vol. 47.
Galbaugh, et al., "EGF-induced activation of Akt results in mTOR-dependent p70S6 kinase phosphorylation and inhibition of HC11 cell lactogenic differentiation" *BMC Cell Biol.*, 2006, pp. 34, vol. 7.
Garcia, et al., "Constitutive activation of Stat3 by the Src and JAK tyrosine kinases participates in growth regulation of human breast carcinoma cells" *Oncogene*, 2001, pp. 2499-2513, vol. 20.
Gouilleux, et al., "Prolactin and Interleukin-2 Receptors in T Lymphocytes Signal through a MGF-STAT&Like Transcription Factor" *Endocrinology*, 1995, pp. 5700-5708, vol. 136.
Halgren, et al., "Glide: A New Approach for Rapid, Accurate Docking and Scoring. 2. Enrichment Factors in Database Screening" *J. Med. Chem.*, 2004, pp. 1750-1759, vol. 47.

(Continued)

*Primary Examiner* — Sreeni Padmanabhan
*Assistant Examiner* — Samira Jean-Louis
(74) *Attorney, Agent, or Firm* — Saliwanchik, Lloyd & Eisenschenk

(57) ABSTRACT

The present invention concerns compounds, compositions containing these compounds, and methods of using these compounds and compositions as inhibitors of Stat3 signaling, Stat3 dimerization, Stat3-DNA binding, Stat5-DNA binding, and/or aberrant cell growth in vitro or in vivo, e.g., as anti-cancer agents for treatment of cancer, such as breast cancer. The compounds of the invention include, but are not limited to, NSC 74859 (S3I-201), NSC 42067, NSC 59263, NSC 75912, NSC 11421, NSC 91529, NSC 263435, and pharmaceutically acceptable salts and analogs of the foregoing. Other non-malignant diseases characterized by proliferation of cells that may be treated using the compounds of the invention, but are not limited to, cirrhosis of the liver; graft rejection; restenosis; and disorders characterized by a proliferation of T cells such as autoimmune diseases, e.g., type 1 diabetes, lupus and multiple sclerosis. The invention further includes an in-vitro screening test for the presence of malignant cells in a mammalian tissue; a method of identifying inhibitors of constitutive Stat3 activation, Stat3-DNA binding, Stat5-DNA binding, and/or Stat3 dimerization; and a method of identifying anti-cancer agents.

16 Claims, 28 Drawing Sheets
(1 of 28 Drawing Sheet(s) Filed in Color)

OTHER PUBLICATIONS

Jing, et al., "Targeting Stat3 with G-quartet oligodeoxynucleotides in human cancer cells" *DNA Cell Biol.*, 2003, pp. 685-696, vol. 22.

Johnson, et al., "Overexpressed pp60c-src Can Induce Focus Formation Without Complete Transformation of NIH 3T3" *Cells Mol. Cell. Biol.*, 1985, pp. 1073-1083, vol. 5.

Kuriyan, et al., "Modular peptide recognition domains in eukaryotic signaling" *Annu Rev Biophys Biomol Struct.*, 1997, pp. 259-288, vol. 26.

Lee, et al., "SH2-Directed Ligands of the Lck Tyrosine Kinase" *J. Med. Chem.*, 2000, pp. 1173-1179, vol. 43.

Mora, et al., "Constitutive Activation of Stat3 in Human Prostate Tumors and Cell Lines: Direct Inhibition of Stat3 Signaling Induces Apoptosis of Prostate Cancer Cells" *Cancer Res.*, 2002, pp. 6659-6666, vol. 62.

Nagel-Wolfrum, et al., "The Interaction of Specific Peptide Aptamers With the DNA Binding Domain and the Dimerization Domain of the Transcription Factor Stat3 Inhibits Transactivation and Induces Apoptosis in Tumor Cells" *Mol Cancer Res.*, 2004, pp. 170-182, vol. 2.

Seidel, et al., "Spacing of palindromic half sites as a determinant of selective STAT (signal transducers and activators of transcription) DNA binding and transcriptional activity" *Proc. Natl. Acad. Sci. USA*, 1995, pp. 3041-3045, vol. 92.

Shao, et al., "Structural Requirements for Signal Transducer and Activator of Transcription 3 Binding to Phosphotyrosine Ligands Containing the YXXQ Motif" *J Biol Chem.*, 2004, pp. 18967-18973, vol. 279.

Sheinerman, et al., "Sequence, structure and energetic determinants of phosphopeptide selectivity of SH2 domains" *J Mol Biol.*, 2003, pp. 823-841, vol. 334.

Shuai, K., et al., "Interferon activation of the transcription factor Stat91 involves dimerization through SH2-phosphotyrosyl peptide interactions" *Cell*, 1994, pp. 821-828, vol. 76.

Song, et al., "A low-molecular-weight compound discovered through virtual database screening inhibits Stat3 function in breast cancer cells" *Proc Natl Acad Sci USA*, 2005, pp. 4700-4705, vol. 102.

Turkson, et al., "STAT proteins: novel molecular targets for cancer drug discovery" *Oncogene*, 2000, pp. 6613-6626, vol. 19.

Turkson, et al., "STAT proteins as novel targets for drug discovery" *Expert Opin Ther Targets*, 2004, pp. 409-422, vol. 8.

Turkson, et al., "Stat3 Activation by Src induces specific gene regulation and is required for cell transformation" *Mol. Cell. Biol.*, 1998, pp. 2545-2552, vol. 18.

Turkson, et al., "Novel peptidomimetic inhibitors of signal transducer and activator of transcription 3 dimerization and biological activity" *Mol Cancer Ther.*, 2004, pp. 261-269, vol. 3.

Turkson, et al., "Phosphotyrosyl Peptides Block Stat3-mediated DNA Binding Activity, Gene Regulation, and Cell Transformation" *J. Biol. Chem.*, 2001, pp. 45443-45455, vol. 276.

Turkson, et al., "A Novel Platinum Compound Inhibits Constitutive Stat3 Signaling and Induces Cell Cycle Arrest and Apoptosis of Malignant Cells" *J Biol. Chem.*, 2005, pp. 32979-32988, vol. 280.

Turkson, et al., "Inhibition of constitutive signal transducer and activator of transcription 3 activation by novel platinum complexes with potent antitumor activity" *Mol. Cancer Ther.*, 2004, pp. 1533-1542, vol. 3.

Wagner, et al., "The SIF binding element confers sisIPDGF inducibility onto the c-fos promoter" *EMBO J.*, 1990, pp. 4477-4484, vol. 9.

Yu, C. L., et al. (1995) Enhanced DNA-binding activity of a Stat3-related protein in cells transformed by the Src oncoprotein. *Science* 269, 81-83.

Yu, et al., "The stats of cancer—new molecular targets come of age" *Nat. Rev. Cancer*, 2004, pp. 97-105, vol. 4.

Zhang, et al., "Interdomain Interaction of Stat3 Regulates Its Src Homology 2 Domain-mediated Receptor Binding Activity" *J. Biol. Chem.*, 2002, pp. 17556-17563, vol. 277.

Zhang, et al., "Activation of Stat3 in v-Src-transformed Fibroblasts Requires Cooperation of Jak1 Kinase Activity" *J. Biol. Chem.*, 2000, pp. 24935-24944, vol. 275.

Gibson B.W. et al. "Liquid Secondary Ionization Mass Spectrometric Characterization of Two Synthetic Phosphotyrosine-Containing Peptides" *Journal of the American Chemical Society*, 1987, pp. 1258-1270, vol. 109(18).

Kitas, E.A. et al. "Synthesis of *O*-Phosphototyrosine-Containing Peptides. 3. Synthesis of H-Pro-Try(*P*)-Val-OH via Dimethyl Phosphate Protection and the Use of Improved Deprotection Procedures[1]" *Journal of Organic Chemistry*, 1990, pp. 4181-4187, vol. 55.

Posternak, T. et al. "De la protection contre l'hydrolyse enzymatique exercée par les groupes phosphoryles II. Sur la préparation de quelques peptides dérivés de la phosphotyrosine et sur leur dégradation enzymatique" *Helv. Chim. Acta*, 1945, pp. 1258-1270, vol. 28.

* cited by examiner

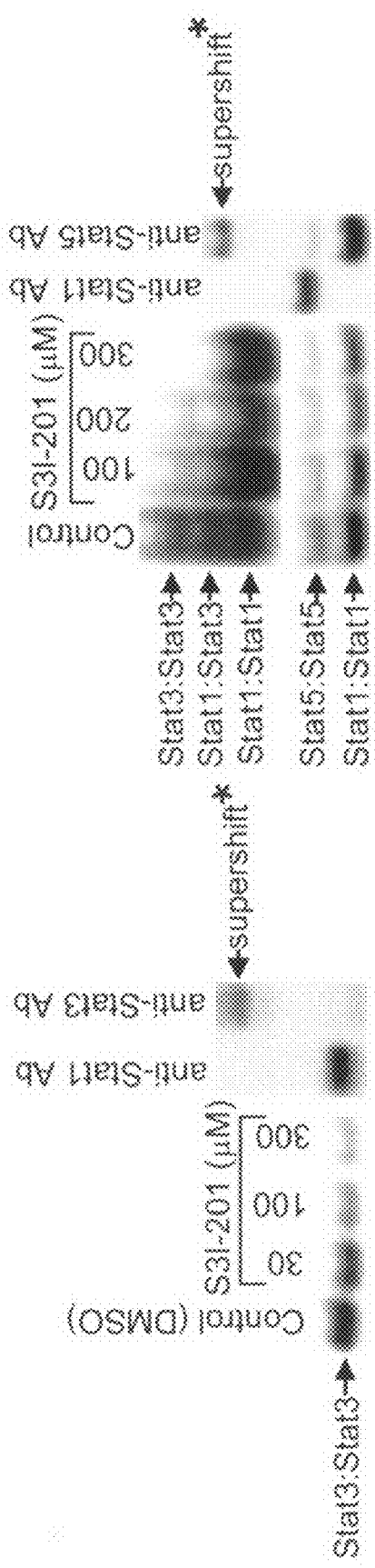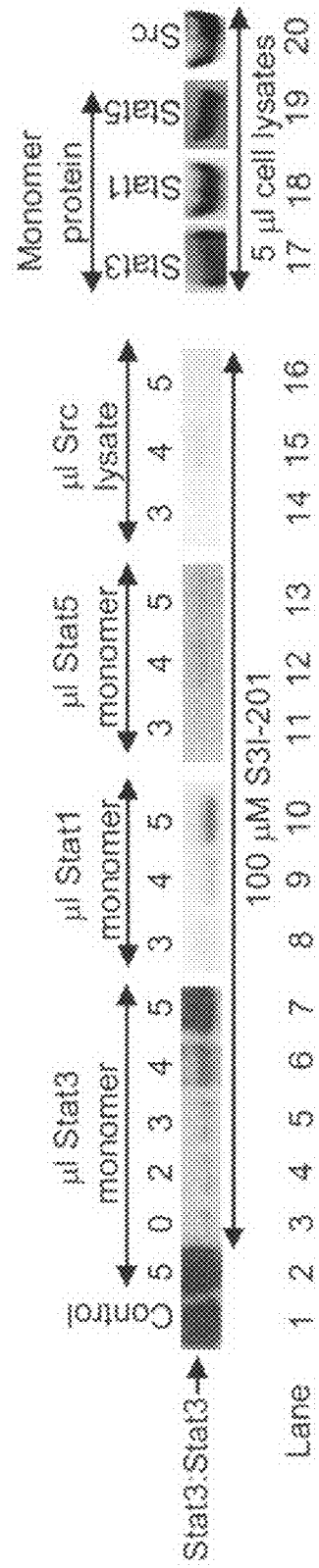
FIG. 2A-1
FIG. 2A-2
FIG. 2B-1
FIG. 2B-2

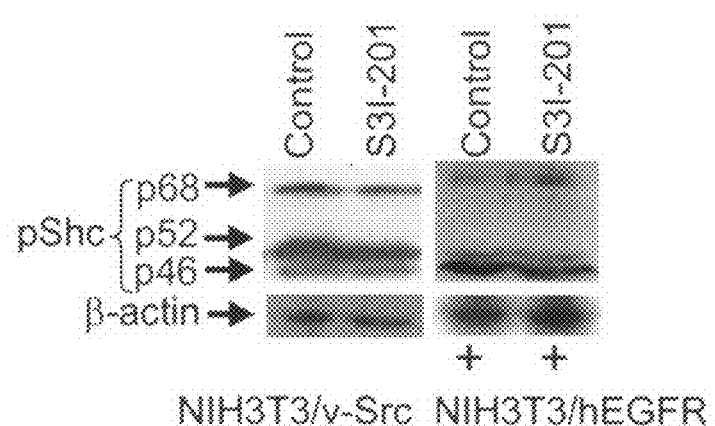
FIG. 2G-1
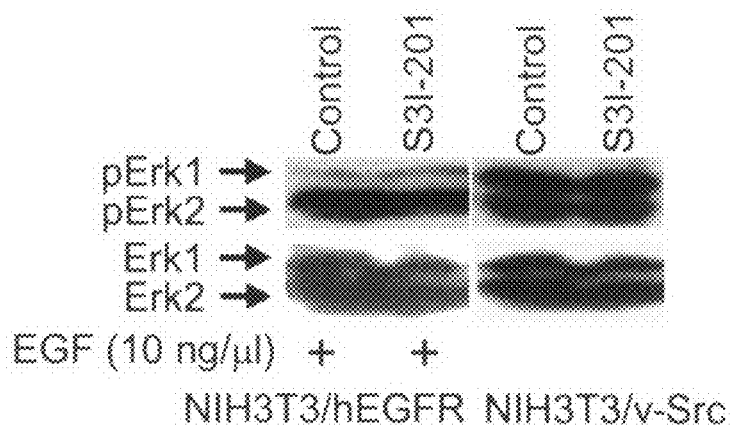
FIG. 2G-2
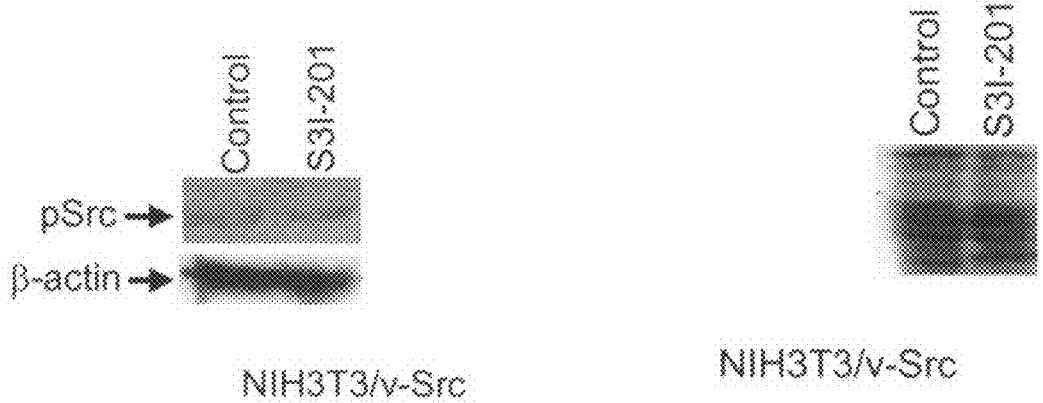
FIG. 2G-3
FIG. 2G-4

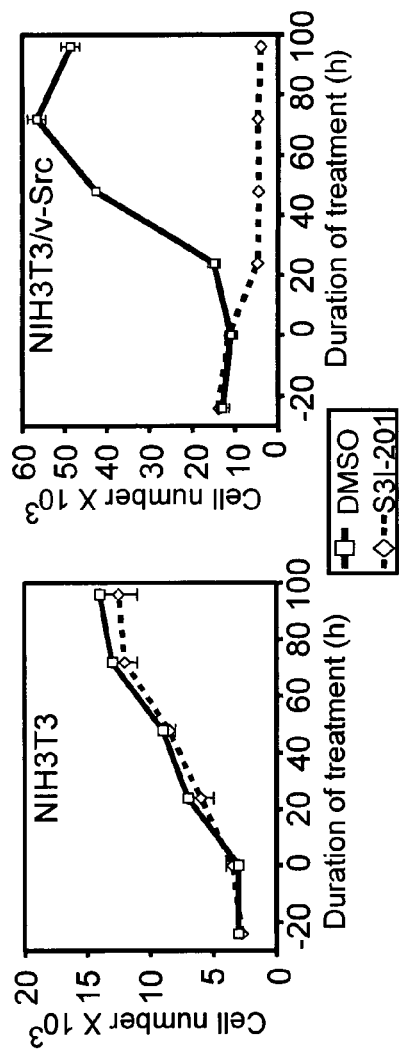
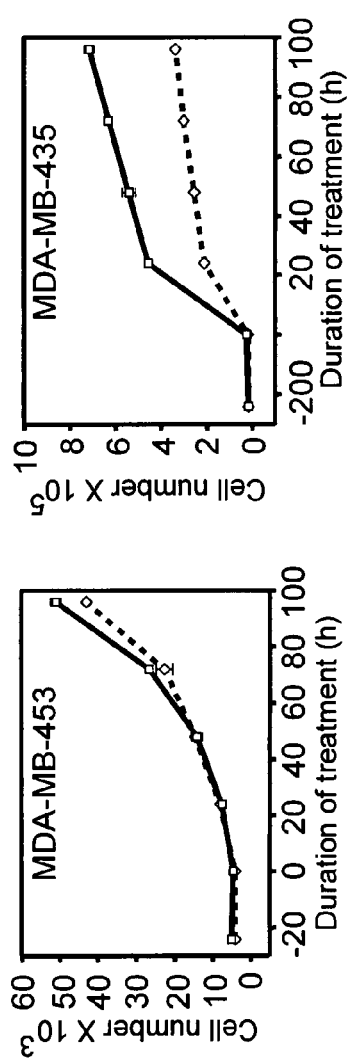
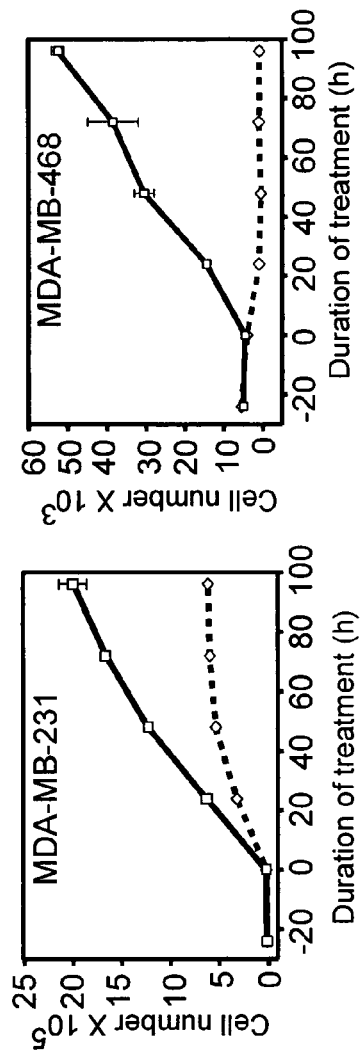
FIG. 4A FIG. 4B FIG. 4C FIG. 4D FIG. 4E FIG. 4F

NSC-74859

NSC-59263

NSC-42067

Fits in the SH2 binding groove $R^1$ = aryl and substituted aryl, heteroaryl, alkyl X = CO, SO$_2$, CONH, alkyl

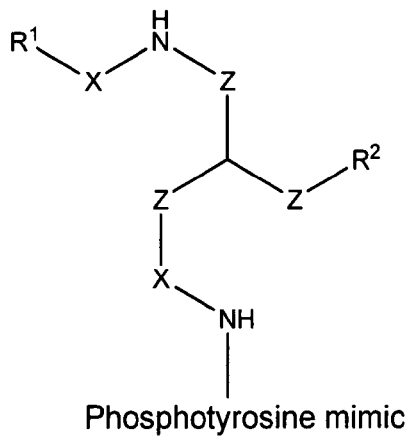

Phosphotyrosine mimic

Hydrophobic group
$R^2$ = aryl and substituted aryl, heteroaryl, alkyl

Z, if present = alkyl chain e.g. (CH$_2$) including n = 0 phosphate mimic = CO$_2$H, SO$_3$H, PO$_3$H, NO$_2$, CH$_2$CO$_2$H, CF$_2$CO$_2$H, CF(CO$_2$H)$_2$ tetrazole

FIG. 12A

Fits in the SH2 binding groove $R^1$ = aryl and substituted aryl, heteroaryl, alkyl X = CO, SO$_2$, CONH, alkyl

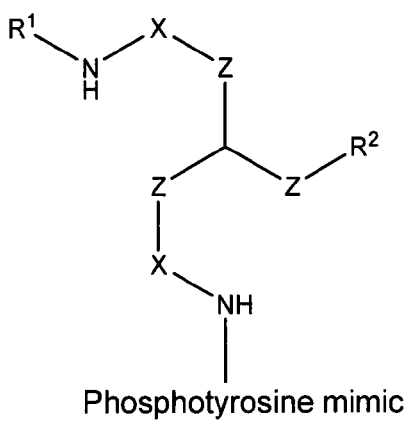

Phosphotyrosine mimic

Hydrophobic group
$R^2$ = aryl and substituted aryl, heteroaryl, alkyl

Z, if present = alkyl chain e.g. (CH$_2$) including n = 0 phosphate mimic = CO$_2$H, SO$_3$H, PO$_3$H, NO$_2$, CH$_2$CO$_2$H, CF$_2$CO$_2$H, CF(CO$_2$H)$_2$ tetrazole

FIG. 12B

Fits in the SH2
binding groove

R¹ = aryl and
substituted aryl,
heteroaryl, alkyl

X = CO, SO₂,
CONH, alkyl

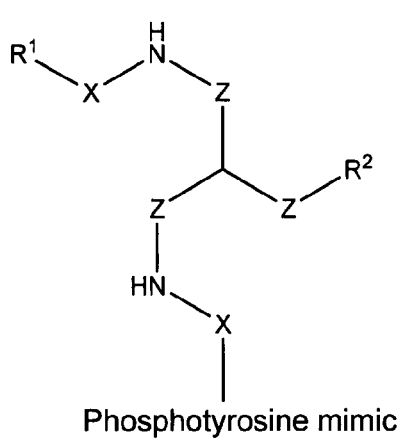

Phosphotyrosine mimic

Hydrophobic group
R² = aryl and substituted
aryl, heteroaryl, alkyl

Z, if present = alkyl chain
e.g. (CH₂) including n = 0 phosphate mimic =
CO₂H, SO₃H, PO₃H,
NO₂, CH₂CO₂H,
CF₂CO₂H, CF(CO₂H)₂
tetrazole

FIG. 12C

Fits in the SH2
binding groove

R¹ = aryl and
substituted aryl,
heteroaryl, alkyl

X = CO, SO₂,
CONH, alkyl

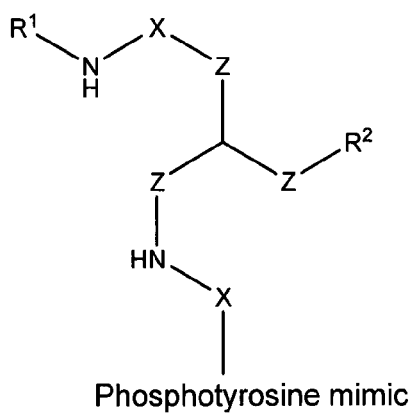

Phosphotyrosine mimic

Hydrophobic group
R² = aryl and substituted
aryl, heteroaryl, alkyl

Z, if present = alkyl chain
e.g. (CH₂) including n = 0 phosphate mimic =
CO₂H, SO₃H, PO₃H,
NO₂, CH₂CO₂H,
CF₂CO₂H, CF(CO₂H)₂
tetrazole

X = H, RPM381
X = CO₂Et, RPM384
X = CO₂H, RPM385

X = CO₂Et, RPM405
X = CO₂H, RPM411

X = CO₂Et, RPM407
X = CO₂H, RPM412

X = CO₂Et, RPM408
X = CO₂H, RPM410

X = CO₂Et, RPM415
X = CO₂H, RPM416

X = CO₂Et, RPM418
X = CO₂H, RPM418-A

X = CO₂H, RPM427

X = CO₂Me, RPM431

X = CO₂H, RPM432

X = CO₂Et, RPM444
X = CO₂H, RPM448

X = CO₂Et, RPM445
X = CO₂H, RPM447

X = CO₂H, RPM452

RPM202

NSC-263435

NSC-11421

NSC-75912

NSC-91529

SMALL MOLECULE INHIBITORS OF STAT3 WITH ANTI-TUMOR ACTIVITY

CROSS-REFERENCE TO RELATED APPLICATION

The present application claims the benefit of U.S. Provisional Application Ser. No. 60/801,750, filed May 19, 2006, which is hereby incorporated by reference herein in its entirety, including any figures, tables, nucleic acid sequences, amino acid sequences, and drawings.

GOVERNMENT SUPPORT

This invention was made with government support under grant number CA106439 awarded by the National Cancer Institute and grant number W81XWH-08-2-0101 awarded by United States Army Medical Research and Materiel Command. The government has certain rights in this invention.

BACKGROUND OF THE INVENTION

Signal transduction proteins important in carcinogenesis and cancer progression present attractive targets for the development of novel anticancer therapeutics. The family of proteins, Signal Transducer and Activator of Transcription (STAT), are activated in response to cytokines and growth factors and promote proliferation, survival, and other biological processes (Bromberg, *J. Breast Cancer Res.*, 2000, 2:86-90; Darnell, J. E., Jr. *Nat. Rev. Cancer*, 2002, 2:740-749; Yu, H. and Jove, R. *Nat. Rev. Cancer*, 2004, 4:97-105). STATs are activated by phosphorylation of a critical tyrosine residue, which is mediated by growth factor receptor tyrosine kinases, Janus kinases or the Src family kinases. Upon tyrosine phosphorylation, dimers of STATs formed between two phosphorylated monomers translocate to the nucleus, bind to specific DNA-response elements in the promoters of target genes, and induce gene expression. Aberrant activity of one of the family members, Stat3, contributes to carcinogenesis and tumor progression by upregulating gene expression and promoting dysregulated growth, survival, and angiogenesis, and modulating immune responses (Darnell, J. E., Jr. *Nat. Rev. Cancer*, 2002, 2:740-749; Yu, H. and Jove, R. *Nat. Rev. Cancer*, 2004, 4:97-105; Bromberg, J. and Darnell, J. E., Jr. *Oncogene*, 2000, 19:2468-2473; Bowman, T. et al. *Oncogene*, 2000, 19:2474-2488; Turkson, J. and Jove, R. *Oncogene*, 2000, 19:6613-6626; Buettner, R. et al. *Clin. Cancer Res.*, 2002, 8:945-954; Turkson, J. *Expert Opin Ther Targets*, 2004, 8:409-422; Darnell, J. E. *Nat. Med.*, 2005, 11:595-596).

As a critical step in STAT activation (Shuai, K. et al. *Cell*, 1994, 76:821-828), the dimerization between two STAT monomers presents an attractive target to abolish Stat3 DNA-binding and transcriptional activity and inhibit Stat3 biological functions (Turkson, J. et al. *J. Biol. Chem.*, 2001, 276: 45443-45455; Turkson, J. et al. *Mol Cancer Ther*, 2004, 3:261-269). Stat3 dimerization relies on the reciprocal binding of the SH2 domain of one monomer to the pTyr peptide containing APY*LKT (Ala-Pro-pTyr-Leu-Lys-Thr) (SEQ ID NO: 1) sequence of the other Stat3 monomer. To pursue the development of inhibitors of Stat3 signaling, key structural information gleaned from the X-ray crystal structure of the Stat3β homodimer (Becker, S. et al. *Nature*, 1998, 394:145-151) was used in the computational modeling and automated docking of small-molecules into the SH2 domain of a Stat3 monomer, relative to the bound native pTyr peptide, in order to identify binders of the Stat3 SH2 domain, and potentially disruptors of Stat3:Stat3 dimers (Shao, H. et al. *J Biol. Chem.*, 2004, 279:18967-18973; Song, H. et al. *Proc Natl Acad Sci USA*, 2005, 102:4700-4705).

BRIEF SUMMARY OF THE INVENTION

Structure-based high throughput virtual screening of the National Cancer Institute (NCI) Chemical libraries identified three compounds that selectively inhibit Stat3 DNA-binding activity in vitro, with $IC_{50}$ values of 65-86 µM, namely NSC 74859, NSC 59263, and NSC 42067. The highest scoring compound, NSC 74859 (re-synthesized as a pure sample and named S3I-201), selectively inhibits Stat3 DNA-binding activity in vitro with an $IC_{50}$ value of 86±33 µM. Furthermore, S3I-201 induces growth inhibition and apoptosis of malignant cells in part by inhibiting constitutively-active Stat3, and induces human breast tumor regression in xenograft models. These findings support the therapeutic potential of S3I-201 and other Stat3 inhibitors against tumors harboring aberrant Stat3 activity.

The present invention concerns isolated compounds, compositions containing these compounds, and methods of using these compounds and compositions as inhibitors of Stat3 and/or as inhibitors of aberrant cell growth, e.g., as anti-cancer agents. In one embodiment, the compound has a structure described by Formula A, B, C, D, E, or F in FIG. 10, 11, or 12A-D, respectively, or a pharmaceutically acceptable salt or analog thereof. In another embodiment, the compound is NSC 74859 (S3I-201; shown in FIG. 7), NSC 59263 (shown in FIG. 8), NSC 42067 (shown in FIG. 9), NSC 75912 (shown in FIG. 50), NSC 11421 (shown in FIG. 49), NSC 91529 (shown in FIG. 51), NSC 263435 (shown in FIG. 48), or a pharmaceutically acceptable salt or analog of any of the foregoing. In another embodiment, the compound is an analog of S3I-201 shown in FIGS. 13-47, i.e., a compound selected from the group consisting of HL2-006-1, HL2-006-2, HL2-006-3, HL2-006-4, HL2-006-5, HL2-011-1, HL2-011-2, HL2-011-3, HL2-011-4, HL2-011-5, BG2069-1, HL2-011-6, HL2-011-7, HL2-005, HL2-003, BG2066, BG2074, BG3004, BG3006A, BG3006B, BG3006D, BG3009, RPM381, RPM384, RPM385, RPM405, RPM411, RPM407, RPM412, RPM408, RPM410, RPM415, RPM416, RPM418, RPM418-A, RPM427, RPM431, RPM432, RPM444, RPM448, RPM445, RPM447, RPM452, RPM202, or a pharmaceutically acceptable salt or analog of any of the foregoing. In another embodiment, the compound is one listed in Table 4, or a pharmaceutically acceptable salt or analog thereof.

One aspect of the invention concerns a method of treating a proliferation disorder in a subject, comprising administering an effective amount of at least one compound of the invention to the subject. In one embodiment, the disorder is mediated by cells harboring constitutively-active Stat3.

Another aspect of the invention concerns a method of suppressing the growth of malignant cells, comprising contacting the cells in vitro or in vivo with an effective amount of at least one compound of the invention. In one embodiment, the malignant cells harbor constitutively-active Stat3.

Another aspect of the invention concerns a method of inducing apoptosis in malignant cells, comprising contacting the cells in vitro or in vivo with an effective amount of at least one compound of the invention. In one embodiment, the malignant cells harbor constitutively-active Stat3.

Another aspect of the invention concerns a method of inhibiting constitutive activation of Stat3 in cells, comprising contacting the cells in vitro or in vivo with an effective amount of at least one compound of the invention.

Another aspect of the invention concerns a method of preventing Stat3 dimerization in a mammalian cell, the method comprising contacting the cell in vitro or in vivo with an effective amount of at least compound of the invention.

Another aspect of the invention concerns a method of disrupting Stat3-DNA binding, the method comprising contacting the Stat3 with an effective amount of at least one compound of the invention.

Another aspect of the invention concerns a method of disrupting Stat5-DNA binding, the method comprising contacting the Stat5 with an effective amount of at least one compound of the invention.

Another aspect of the invention concerns an in-vitro screening test for the presence of malignant cells in a mammalian tissue, the test including: obtaining a sample containing viable cells of the tissue; culturing the sample under conditions promoting growth of the viable cells contained therein; treating the cultured sample with a compound of the invention; and analyzing the treated sample by a method effective to determine percent apoptosis of cells as an indicator of presence of malignant cells in the sample.

Another aspect of the invention concerns a method of identifying inhibitors of constitutive Stat3 activation, Stat3-DNA binding, Stat5-DNA binding, and/or Stat3 dimerization, the method comprising selecting a compound having a structure of Formula A, B, C, D, E, or F (shown in FIGS. 10-12A-D); and determining whether the compound inhibits constitutive Stat3 activation, disrupts Stat3-DNA binding, disrupts Stat5-DNA binding, prevents (e.g., reduces incidence of) Stat3 dimerization, or determining two or more of the foregoing.

Another aspect of the invention concerns a method of identifying anti-cancer agents, the method comprising selecting a compound having a structure of Formula A, B, C, D, E, or F (shown in FIGS. 10-12A-D); and determining whether the compound inhibits the growth of cancer cells in vitro or in vivo (e.g., in an animal model).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A depicts S3I-201 docked to the SH2 domain of Stat3; a solvent accessible surface of the protein (rendered on a 6 Å shell of residues surrounding the ligand) is shown. It is color coded according to the electrostatic potential. Hydrogen bonding to Lys 591, Ser 611, Ser 613, and Arg 609 is shown by white dashed lines. Carbon atoms of S3I-201 are shown in green. FIG. 1B depicts S3I-201 docked to the SH2 domain of Stat3 along with pTyr peptide. Coloring for pTyr peptide is as follows: (P: red, Y*: pink; L: orange; K: green).

FIGS. 2A-1, 2A-2, 2B-1, 2B-2, 2C-1, 2C-2, 2D, 2E, 2F, 2G-1, 2G-2, 2G-3, and 2G-4 show the effects of S3I-201 on STATs, Shc, Src, and Erks activation, and on Lck-SH2 domain-phosphopeptide binding. In FIGS. 2A-1 and 2A-2, nuclear extracts containing activated Stat1, Stat3, and/or Stat5 proteins were pre-incubated with or without S3I-201 for 30 minutes at room temperature prior to incubation with radiolabeled hSIE probe that binds Stat1 and Stat3 or MGFe probe that binds Stat1 and Stat5, or nuclear extracts were incubated with anti-Stat1, anti-Stat3, or anti-Stat5A antibody for 30 minutes at room temperature prior to incubation with radiolabeled probes, and subjecting to EMSA analysis. In FIG. 2B-1, cell lysates containing activated Stat3 were pre-incubated with S3I-201 or without (control, 0.05% DMSO) in the presence or absence of increasing amount of cell lysates containing inactive Stat3 protein (monomer), inactive Stat1 protein (monomer), inactive Stat5 protein (monomer), or Src protein prior to incubation with radiolabeled hSIE probe and subjecting to EMSA analysis. FIG. 2B-2 shows SDS-PAGE and Western blot analysis of cell lysate preparations of equal total protein containing inactive Stat3 (monomer), Stat1 (monomer), or Stat5 (monomer), or Src protein probing with anti-Stat3, anti-Stat1, anti-Stat5, or anti-Src antibody. FIG. 2C-1 shows SDS-PAGE and Western blot analysis of Stat3-YFP immunoprecipitates (i.p. YFP, left panels) probing for FLAG-Stat3 (anti-FLAG, upper panel) or Stat3-YFP (anti-YFP, lower panel), or of FLAG-Stat3 immunoprecipitates (i.p. FLAG, right panels) probing for Stat3-YFP (anti-YFP, lower panel) or FLAG-Stat3 (anti-FLAG, upper panel). FIG. 2C-2 shows SDS-PAGE and Western blot analysis of whole-cell lysates from FLAG-ST3-transiently-transfected cells (input) treated with S3I-201 or untreated (control) probing for FLAG. FIG. 2D shows in vitro ELISA for the binding of Lck-SH2-GST to the conjugate biotinylated pTyr-peptide (EPQpYEEIEL (where pY represents pTyr)) (SEQ ID NO:2), and effects of increasing concentration of S3I-201. FIG. 2E shows EMSA analysis of nuclear extract preparations from v-Src-transformed mouse fibroblasts (NIH3T3/v-Src) treated for the indicated times or from the human breast cancer MDA-MB-231, MDA-MB-435 and MDA-MB-468 cells treated for 48 hours with 100 μM S3I-201 and incubated with radiolabeled hSIE probe. FIG. 2F shows SDS-PAGE and Western blot analysis of whole-cell lysates from NIH3T3/v-Src fibroblasts untreated (control) or treated with S3I-201 (100 μM, 24 hours) probing with anti-pTyr705 Stat3 or anti-Stat3 antibody. FIGS. 2G-1, 2G-2, 2G-3, and 2G-4 show SDS-PAGE and Western blot analysis of cell lysates prepared from NIH3T3/v-Src or EGF-stimulated NIH3T3/hEGFR untreated (control) or treated with S3I-201 (100 μM, 24 hours) probing with antibodies against pShc (FIG. 2G-1), pErk1/2 (pp42/pp44), Erk1/2 (FIG. 2G-2), pSrc (FIG. 2G-3), or β-actin, or anti-phosphoTyr antibody, clone 4G10 (FIG. 2G-4). Positions of STATs:DNA complexes or proteins in gel are labeled; control lanes represent nuclear extracts treated with 0.05% DMSO, and nuclear extracts or cell lysates prepared from 0.05% DMSO-treated cells; asterisks (*) indicates supershifted complexes of STAT:probe:antibody in the presence of anti-Stat1, anti-Stat3 or anti-Stat5 antibody; values are the mean and S.D. of three independent determinations.

FIGS. 4A-4G show that S3I-201 inhibits anchorage-dependent and—independent growth only of cells that contain persistently-active Stat3. Normal mouse fibroblasts (NIH3T3) (FIG. 4A) and v-Src transformed counterparts (NIH3T3/v-Src) (FIG. 4B), as well as the human breast carcinoma cells (MDA-MB-453 [FIG. 4C]), MDA-MB-435 [FIG. 4D], MDA-MB-231 [FIG. 4E], or MDA-MB-468 [FIG. 4F]) were untreated (0.05% DMSO, control) or treated with 100 μM S3I-201 and counted by trypan blue exclusion on each of four days for viable cell number. In FIG. 4G, v-Src transformed mouse fibroblasts (NIH3T3/v-Src) and their v-Ras transformed counterparts (NIH3T3/v-Ras) were grown in soft-agar suspension and untreated (0.05% DMSO, control) or treated with 100 μM S3I-201 every 3 days until large colonies were visible, which were enumerated. Values are the mean and S.D. of 3-4 independent determinations.

In FIG. 5A, normal NIH3T3 mouse fibroblasts and their v-Src transformed counterparts (NIH3T3/v-Src), and the human breast carcinoma MDA-MB-453 and MDA-MB-435 cell lines were untreated (0.05% DMSO) or treated with 100-300 μM S3I-201 for 48 hours and subjected to Annexin V staining and Flow Cytometry. In FIG. 4B, human breast carcinoma MDA-MB-231 cells were transfected with pcDNA3 (mock), Stat3C or untransfected (Non), or the v-Src transformed mouse fibroblasts (NIH3T3/v-Src) were transfected with pcDNA3 (mock), N-terminus of Stat3 (ST3-NT) or the Stat3 SH2 domain (ST3-SH2) for 4 hours. Twenty four hours after transfection, cells were untreated (0.05% DMSO, (−)) or treated (+) with 100 μM S3I-201 for an additional 24 hours and subjected to Annexin V staining and Flow Cytometry. FIG. 5C shows SDS-PAGE and Western blot analysis of whole-cell lysates prepared from the v-Src-transformed mouse fibroblasts (NIH3T3/v-Src) or the human breast cancer MDA-MB-231 cells untreated (DMSO, control) or treated with 100 μM S3I-201 for 48 hours probing with anti-Cyclin D1, Bcl-xL and Survivin antibodies. Values are the mean and S.D. of six independent determinations. Western blot data are representative of 3 independent analyses.

In FIG. 6A, human breast (MDA-MB-231) tumor-bearing mice were given S3I-201 (5 mg/kg) i.v. every 2 or every 3 days. Tumor sizes were monitored every 2 to 3 days, converted to tumor volumes, and plotted. In FIG. 6B, upon completion of study 3 days after the last S3I-201 injection, animals were sacrificed and tumor from one control animal (DMSO-treated) or residual tumor tissue from S3I-201 treated (T1 and T2) mice were extracted and lysate preparations of equal total proteins were analyzed for Stat3 activation by incubating with radiolabeled hSIE probe and subjecting to EMSA analysis (lanes 1 to 3), or lysates from control tumor tissue of equal protein were pre-incubated with or without increasing concentration of S3I-201 prior to incubation with radiolabeled hSIE probe and subjecting to EMSA analysis (lanes 1, 4, 5 and 6). In FIG. 6C, lysate preparations from extracted tumor tissue in control or treated (T1 and T2) were subjected to SDS-PAGE and Western blot analysis for pTyr Stat3 (pYStat3, upper panel) and total Stat3 (lower panel). Values are the mean and S.D. of eight tumor-bearing mice each. Positions of Stat3:DNA complexes are shown.

FIGS. 12A-12D show the structures of T-shaped molecules (Formulas C, D, E, and F, respectively) that bind in the SH2 binding groove. The hydrophobic group containing $R_2$ binds in a STAT3 hydrophobic pocket formed from Ile634, Ile597, Lys591, and Arg595. In FIGS. 12A-12D, the XNH groups have a transposed arrangement (NHX) with respect to one another. Referring to FIGS. 12A-12D, $R_1$ and $R_2$, if present, can be an aliphatic or aromatic group; X, if present =CO, $SO_2$, CONH, or alkyl; Z, if present, is alkyl; and phosphate mimic=that shown in FIGS. 10 and 11, e.g., $CO_2H$, $SO_3H$, $PO_3H$, $NO_2$, $CH_2CO_2H$, $CF_2CO_2H$, or $CF(CO_2H)_2$ tetrazole. Preferably, $R_2$ is a hydrophobic group or part of a hydrophobic group. In one embodiment, $R_1$, if present, is H, alkyl, alkenyl, cycloalkyl, heterocycloalkyl, cylcoalkenyl, heterocycloalkenyl, acyl, and aryl, any of which may be optionally substituted; and $R_2$, if present is H, alkyl, alkenyl, cycloalkyl, heterocycloalkyl, cylcoalkenyl, heterocycloalkenyl, acyl, and aryl, any of which may be optionally substituted. In a preferred embodiment, $R_1$, if present, is aryl, substituted aryl, heteroaryl or alkyl; and $R_2$, if present is a hydrophobic group such as aryl, substituted aryl, heteroaryl or alkyl.

BRIEF DESCRIPTION OF THE SEQUENCES

SEQ ID NO: 1 is the native pTyr-peptide (APY*LKT; *=phosphorylation).

SEQ ID NO:2 is the biotinylated conjugate pTyr-peptide (EPQpYEEIEL (where pY represents pTyr)).

SEQ ID NO:3 is the sequence of the hSIE (high affinity sis-inducible element from the c-fos gene, m67 variant) oligonucleotide probe.

SEQ ID NO:4 is the sequence of the MGFe (mammary gland factor element from the bovine β-casein gene promoter) oligonucleotide probe.

DETAILED DESCRIPTION OF THE INVENTION

The present invention concerns isolated compounds, compositions comprising these compounds, and methods of using these compounds and compositions as inhibitors of Stat3 and inhibitors of aberrant cell growth, e.g., as anti-cancer agents.

Constitutively-active Stat3 is a prevalent molecular abnormality with a critical role in human malignant transformation, and which represents a valid target for novel anticancer drug design. S3I-201 (NSC 74859) is a novel inhibitor of Stat3 activity identified from the National Cancer Institute chemical libraries using structure-based virtual screening with a computer model of the Stat3 SH2 domain bound to its Stat3 phosphotyrosine peptide derived from the X-ray crystal structure of the Stat3β homodimer. S3I-201 inhibits Stat3:Stat3 complex formation, and Stat3 DNA-binding and transcriptional activities. Furthermore, S3I-201 inhibits growth and induces apoptosis preferentially in tumors cells that contain persistently activated Stat3. Constitutively-dimerized and active Stat3C and Stat3 SH2 domain rescue tumor cells from S3I-201-induced apoptosis. Finally, S3I-201 inhibits the expression of the Stat3-regulated genes Cyclin D1, Bcl-xL and Survivin, and inhibits the growth of human breast tumors in vivo. These findings strongly suggest that the antitumor activity of S3I-201 is mediated in part through inhibition of aberrant Stat3 activation and provide the proof-of-concept for the potential clinical use of Stat3 inhibitors, such as S3I-201, in tumors harboring aberrant Stat3.

Figure 48:
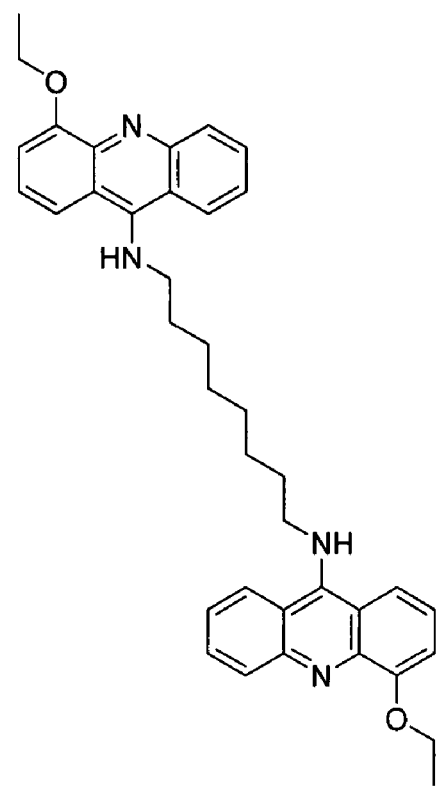
FIG. 48 shows the chemical structure of NSC-263435.
Figure 49:
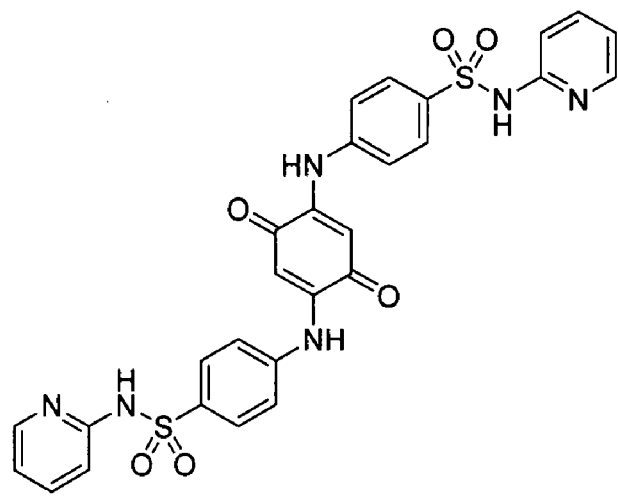
FIG. 49 shows the chemical structure of NSC-11421.
Figure 50:
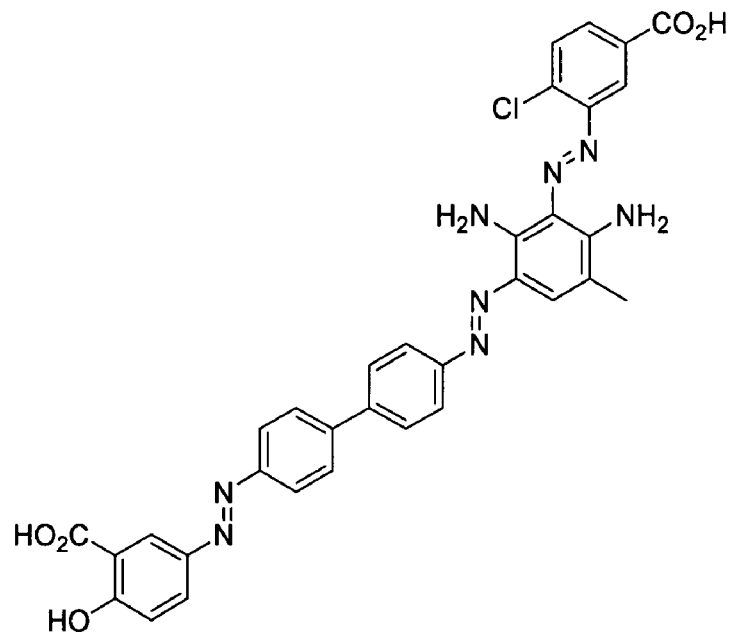
FIG. 50 shows the chemical structure of NSC-75912.
Figure 51:
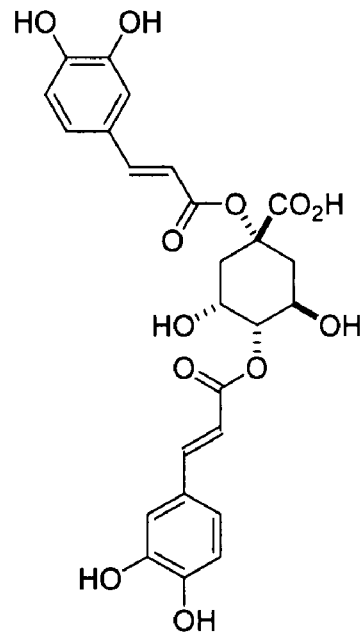
FIG. 51 shows the chemical structure of NSC-91529.

Aspects of the invention include, but are not limited to, Stat3 inhibitors, compositions comprising these compounds, and methods of using these compounds and compositions as inhibitors of Stat3 and/or as inhibitors of aberrant cell growth, e.g., as anti-cancer agents. In one embodiment, the compound has a structure encompassed by Formula A, B, C, D, E, or F in FIGS. 10-12A-D, respectively, or a pharmaceutically acceptable salt or analog thereof. In another embodiment, the compound is NSC 74859 (S3I-201; shown in FIG. 7), NSC 59263 (shown in FIG. 8), NSC 42067 (shown in FIG. 9), NSC 75912 (shown in FIG. 50), NSC 11421 (shown in FIG. 49), NSC 91529 (shown in FIG. 51), NSC 263435 (shown in FIG. 48), or a pharmaceutically acceptable salt or analog of any of the foregoing. In another embodiment, the compound is an analog of S3I-201 shown in FIGS. 13-47, i.e., a compound selected from the group consisting of HL2-006-1, HL2-006-2, HL2-006-3, HL2-006-4, HL2-006-5, HL2-011-1, HL2-011-2, HL2-011-3, HL2-011-4, HL2-011-5, BG2069-1, HL2-011-6, HL2-011-7, HL2-005, HL2-003, BG2066, BG2074, BG3004, BG3006A, BG3006B, BG3006D, BG3009, RPM381, RPM384, RPM385, RPM405, RPM411, RPM407, RPM412, RPM408, RPM410, RPM415, RPM416, RPM418, RPM418-A, RPM427, RPM431, RPM432, RPM444, RPM448, RPM445, RPM447, RPM452, and RPM202, or a pharmaceutically acceptable salt or analog of any of the foregoing. In another embodiment, the compound is one listed in Table 4, or a pharmaceutically acceptable salt or analog thereof.

One aspect of the subject invention provides methods for using the compounds of the invention as Stat3 inhibitors and/or as anti-proliferative agents. Thus, in one embodiment, the method of the invention comprises administering a compound of the invention to cells in vitro or in vivo in an amount sufficient to achieve the desired result, e.g., reduction of Stat3 activation. In another embodiment, the method comprises administering a compound of the invention to a human or non-human subject in an amount effective to achieve the desired therapeutic result. In one embodiment, more than one compound of the invention is administered to the cells in vitro or in vivo. In a preferred embodiment, the compound is S3I-201, or a pharmaceutically acceptable salt or analog thereof.

As used herein, the terms "treatment" and "treating", and grammatical variations thereof, include therapy and prophylaxis. When used as a therapy, the compounds of the invention, by themselves or in conjunction with other agents, alleviate or reduce one or more symptoms associated with a proliferation disorder (e.g., cancer). Thus, the treatment methods may or may not be curative in nature. When used as a prophylactic treatment, the compounds of the invention, by themselves or in conjunction with other agents, delay the onset of (and may prevent) one or more symptoms associated with a proliferation disorder (e.g., cancer), or may prevent the genesis of the condition.

In one aspect, the method of the invention is a method for treating a proliferation disorder, such as cancer, comprising administering an effective amount of a compound of the invention to a subject in need thereof.

In another aspect, the method of the invention is a method for inhibiting the growth of cancer cells in vitro or in vivo, comprising administering an effective amount of a compound of the invention to the cancer cells.

In another aspect, the subject invention provides compositions comprising at least one isolated compound of the invention, and a pharmaceutically acceptable carrier.

By inhibiting the growth of cells proliferating in an aberrant manner, the methods, compounds, and compositions of the present invention can be used to treat a number of cell proliferation disorders, such as cancers, including, but not limited to, leukemias and lymphomas, such as acute lymphocytic leukemia, acute non-lymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms' Tumor, bone tumors, and soft-tissue sarcomas, common solid tumors of adults such as lung cancer, colon and rectum cancer, breast cancer, prostate cancer, urinary cancers, uterine cancers, bladder cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The methods of the subject invention can be carried out in vivo or in vitro, to inhibit the growth of cells (e.g., cancer cells) in humans and non-human mammals. Treatment for a proliferation disorder can proceed by the Stat3 inhibitor's anti-proliferative activity such as pro-apoptotic activity, or by other mechanisms. In one embodiment, the proliferation disorder is one on which the Stat3 inhibitor(s) act by inhibition of Stat3 DNA-binding.

Compounds of the invention having the capability to modulate (e.g., reduce or eliminate) signaling of the STAT3 and/or STAT5 signaling pathway in vitro and/or in vivo, or to inhibit the growth of cancer cells in vitro and/or in vivo by inhibition of STAT3 and/or STAT5 signaling or a different mechanism, would be considered to have the desired biological activity in accordance with the subject invention. For therapeutic applications, compounds of the subject invention have the capability to inhibit activation of the STAT3 and/or STAT5 signaling pathway, or to inhibit the growth of cancer cells in vitro and/or in vivo by inhibition of STAT3 and/or STAT5 signaling or a different mechanism. Inhibition of STAT3 and/or STAT5 signaling can be assessed directly or indirectly by various methods, including assays for inhibition of STAT3 dimerization, inhibition of STAT3 DNA-binding, and/or inhibition of STAT5 DNA-binding, for example. Inhibition of STAT3 and/or STAT5 signaling by compounds of the invention selectively promotes apoptosis in tumor cells that harbor constitutively activated STAT3. Therefore, the desirable goals of promoting apoptosis ("programmed cell death") of selective cancerous cells and suppression of malignant transformation of normal cells within a patient are likewise accomplished through administration of antagonists or inhibitors of STAT 3 signaling of the present invention, which can be administered as simple compounds or in a pharmaceutical formulation.

In one embodiment, the proliferation disorder to be treated is a cancer producing a tumor characterized by over-activation of Stat1, Stat3, Stat5, or a combination of two or all three of the foregoing. Examples of such cancer types include, but are not limited to, breast cancer, ovarian cancer, multiple myeloma and blood malignancies, such as acute myelogenous leukemia.

In addition to cancer, the proliferation disorder to be treated using the compounds, compositions, and methods of the invention can be one characterized by aberrant Stat3 activation within cells associated with a non-malignant disease, pathological state or disorder (collectively "disease"), and likewise comprising administering or contacting the cells with a an effective amount of one or more Stat3 inhibitors to reduce or inhibit the proliferation. The proliferation, hypertrophy or overgrowth of cells that is common to these diseases is mediated by overactivation of Stat3. This protein becomes activated by a series of biochemical events. The activation of Stat3 then leads to another series of inter-related biochemical reactions or signal transduction cascades that ultimately produce cell growth and division.

In one embodiment, the proliferation disorder to be treated is characterized by a proliferation of T-cells such as autoimmune disease, e.g., type 1 diabetes, lupus and multiple sclerosis, and pathological states such as graft rejection induced by the presentation of a foreign antigen such as a graft in response to a disease condition (e.g., kidney failure). Other non-malignant diseases characterized by proliferation of cells include cirrhosis of the liver and restenosis.

The methods of the present invention can be advantageously combined with at least one additional treatment method, including but not limited to, chemotherapy, radiation therapy, or any other therapy known to those of skill in the art for the treatment and management of proliferation disorders such as cancer.

In one embodiment, the methods and compositions of the invention include the incorporation of a ras antagonist. Ras protein is the on/off switch between hormone/growth factor receptors and the regulatory cascading that result in cell division. For Ras to be activated (i.e., turned on) to stimulate the regulatory cascades, it must first be attached to the inside of the cell membrane. Ras antagonist drug development aimed at blocking the action of Ras on the regulatory cascades has focused on interrupting the association of Ras with the cell membrane, blocking activation of Ras or inhibiting activated Ras. The details of the approaches to development of Ras antagonists are reviewed in Kloog, et al., *Exp. Opin. Invest. Drugs*, 1999, 8(12):2121-2140. Thus, by the term "ras antagonist", it is meant any compound or agent that targets one or more of these phenomena so as to result in inhibition of cell proliferation.

The Ras antagonists that may be used in conjunction with the Stat3 inhibitors of the invention affect (e.g., inhibit) the binding of Ras to the cell membrane, which in turn reduces or inhibits the unwanted cell proliferation. Preferred Ras antagonists include farnesyl thiosalicylic acid (FTS) and structurally related compounds or analogs thereof, which are believed to function by displacing or dislodging Ras from its membrane anchor. These organic compounds may be administered parenterally or orally. In a particularly preferred embodiment, the Ras antagonist is formulated for oral or parenteral administration by complexation with cyclodextrin.

While compounds of the invention can be administered to cells in vitro and in vivo as isolated compounds, it is preferred to administer these compounds as part of a pharmaceutical composition. The subject invention thus further provides compositions comprising a compound of the invention, such as those shown in FIGS. 7-9 (NSC 74859 (S3I-201), NSC 59263, NSC 42067), FIGS. 48-51 (NSC 42067, NSC 75912, NSC 11421 NSC 91529, and NSC 263435), FIGS. 10-12A-D (Formulas A, B, C, D, E, and F), FIGS. 13-47 (HL2-006-1, HL2-006-2, HL2-006-3, HL2-006-4, HL2-006-5, HL2-011-1, HL2-011-2, HL2-011-3, HL2-011-4, HL2-011-5, BG2069-1, HL2-011-6, HL2-011-7, HL2-005, HL2-003, BG2066, BG2074, BG3004, BG3006A, BG3006B, BG3006D, BG3009, RPM381, RPM384, RPM385, RPM405, RPM411, RPM407, RPM412, RPM408, RPM410, RPM415, RPM416, RPM418, RPM418-A, RPM427, RPM431, RPM432, RPM444, RPM448, RPM445, RPM447, RPM452, and RPM202), and listed in Tables 4 and 5, or physiologically acceptable salt(s) or analogs of any of the foregoing; in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The compounds of the invention can be formulated according to known methods for preparing pharmaceutically useful compositions. Formulations are described in a number of sources which are well known and readily available to those skilled in the art. For example, *Remington's Pharmaceutical Science* (Martin, E. W., 1995, Easton Pa., Mack Publishing Company, $19^{th}$ ed.) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Figure 7:
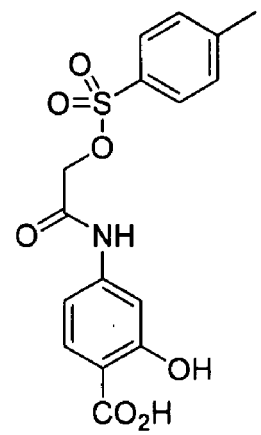
FIG. 7 shows the chemical structure of NSC-74859 (also referred to herein as S3I-201).
Figure 8:
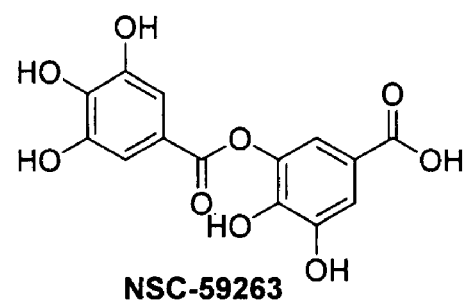
FIG. 8 shows the chemical structure of NSC-59263.
Figure 9:
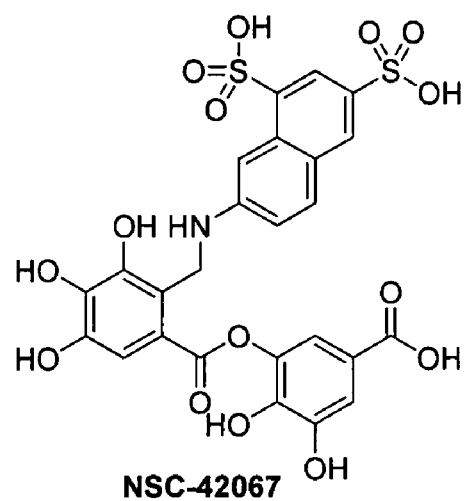
FIG. 9 shows the chemical structure of NSC-42067.
Figure 10:
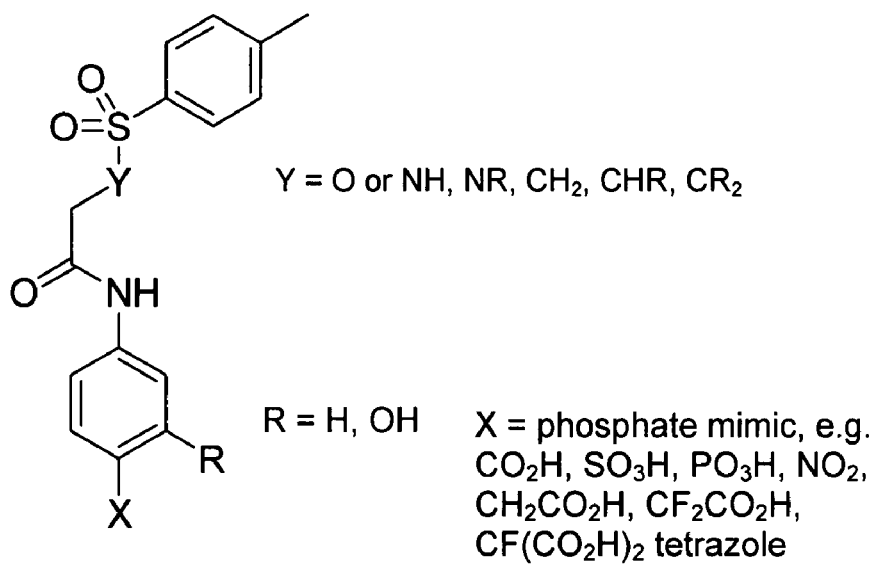
FIG. 10 shows the chemical structure of formula A, encompassing some embodiments of the invention. R, if present =H or OH; Y=O, NH, NR, $CH_2$, CHR, or $CR_2$; and X, if present=a phosphate mimic, e.g., $CO_2H$, $SO_3H$, $PO_3H$, $NO_2$, $CH_2CO_2H$, or $CF_2CO_2H$, $CF(CO_2H)_2$ tetrazole.
Figure 11:
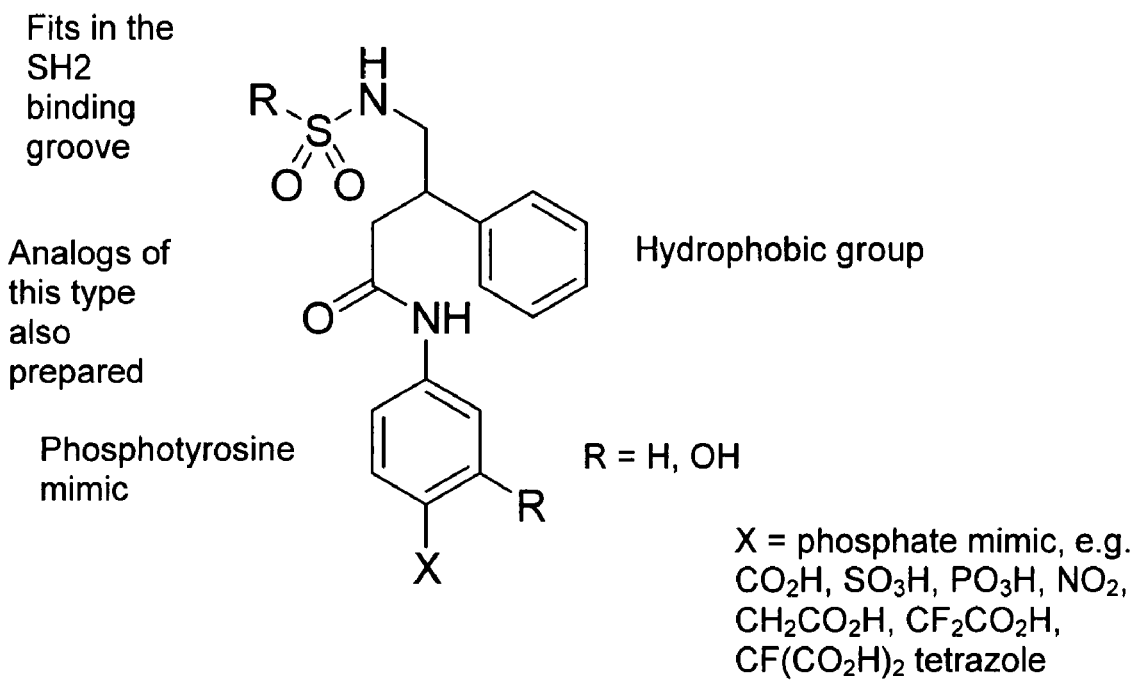
FIG. 11 shows the chemical structure of formula B, encompassing some embodiments of the invention. R, if present =H or OH; X, if present=phosphate mimic, e.g., $CO_2H$, $SO_3H$, $PO_3H$, $NO_2$, $CH_2CO_2H$, or $CF_2CO_2H$, $CF(CO_2H)_2$ tetrazole.
Figure 13:
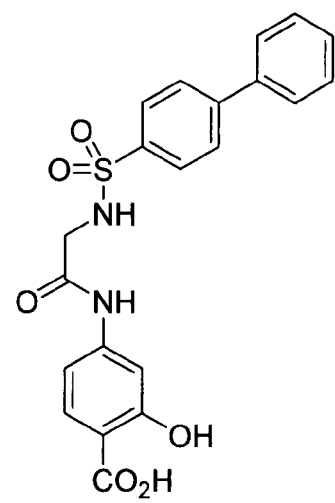
FIG. 13 shows the chemical structure of the compound HL2-006-1, an analog of S3I-201.
Figure 14:
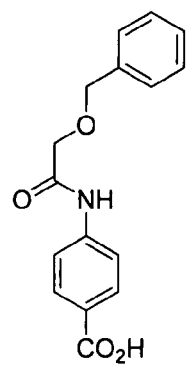
FIG. 14 shows the chemical structure of the compound HL2-006-2, an analog of S3I-201.
Figure 15:
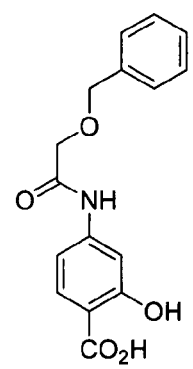
FIG. 15 shows the chemical structure of the compound HL2-006-3, an analog of S3I-201.
Figure 16:
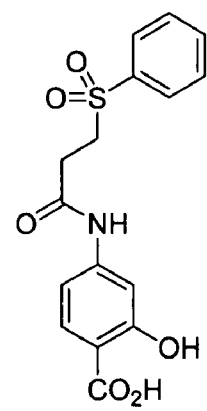
FIG. 16 shows the chemical structure of the compound HL2-006-4, an analog of S3I-201.
Figure 17:
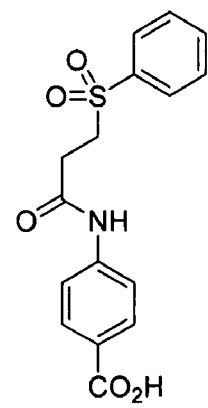
FIG. 17 shows the chemical structure of the compound HL2-006-5, an analog of S3I-201.
Figure 18:
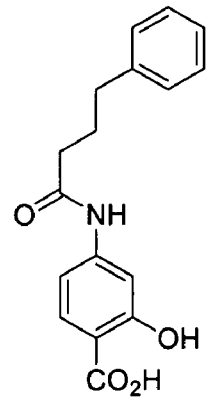
FIG. 18 shows the chemical structure of the compound HL2-011-1, an analog of S3I-201.
Figure 19:
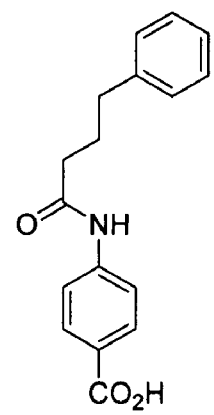
FIG. 19 shows the chemical structure of the compound HL2-011-2, an analog of S3I-201.
Figure 20:
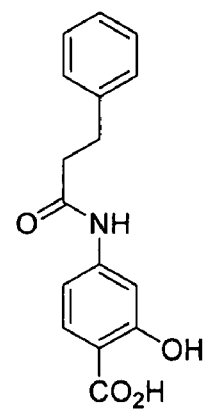
FIG. 20 shows the chemical structure of the compound HL2-011-3, an analog of S3I-201.
Figure 21:
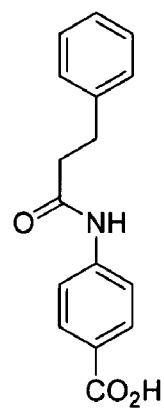
FIG. 21 shows the chemical structure of the compound HL2-001-4, an analog of S3I-201.
Figure 22:
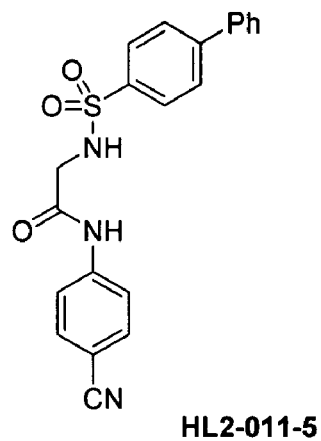
FIG. 22 shows the chemical structure of the compound HL2-011-5, an analog of S3I-201.
Figure 23:
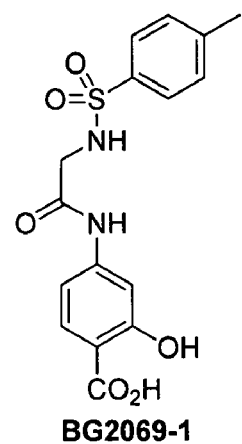
FIG. 23 shows the chemical structure of the compound BG2069-1, an analog of S3I-201.
Figure 24:
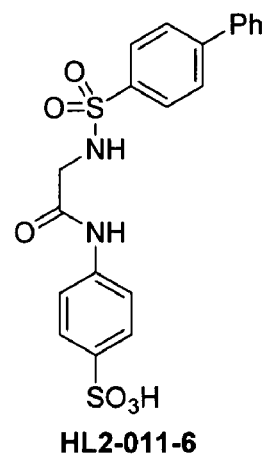
FIG. 24 shows the chemical structure of the compound HL2-011-6, an analog of S3I-201.
Figure 25:
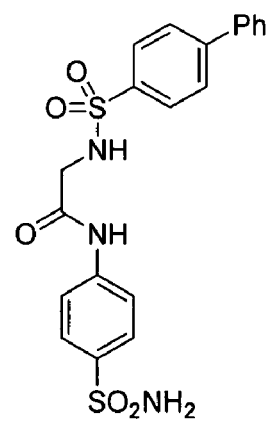
FIG. 25 shows the chemical structure of the compound HL2-011-7, an analog of S3I-201.
Figure 26:
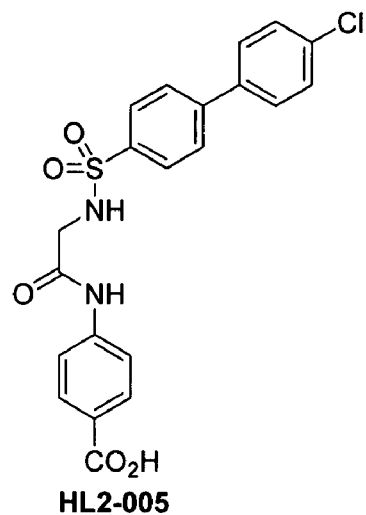
FIG. 26 shows the chemical structure of the compound HL2-005, an analog of S3I-201.
Figure 27:
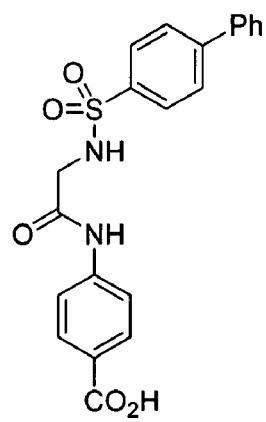
FIG. 27 shows the chemical structure of the compound HL2-003, an analog of S3I-201.
Figure 28:
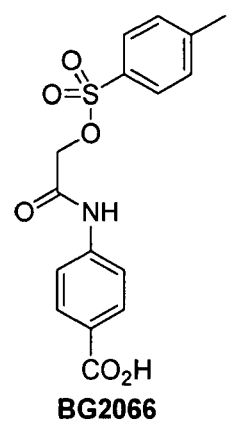
FIG. 28 shows the chemical structure of the compound BG2066, an analog of S3I-201.
Figure 29:
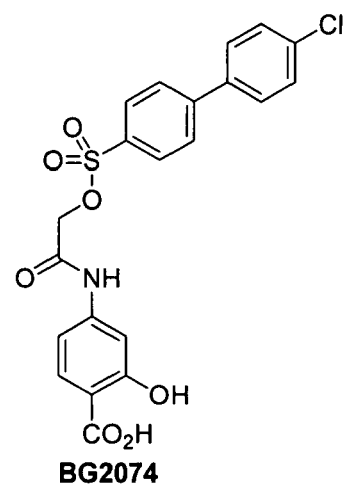
FIG. 29 shows the chemical structure of the compound BG2074, an analog of S3I-201.
Figure 30:
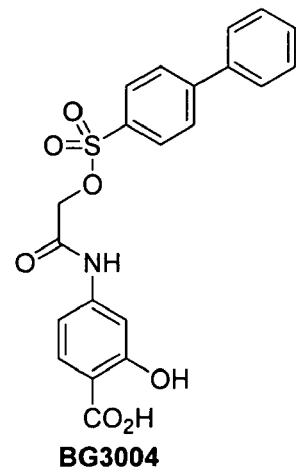
FIG. 30 shows the chemical structure of the compound BG3004, an analog of S3I-201.
Figure 31:
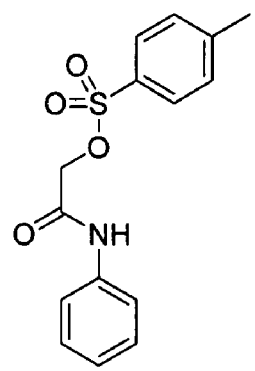
FIG. 31 shows the chemical structure of the compound BG3006A, an analog of S3I-201.
Figure 32:
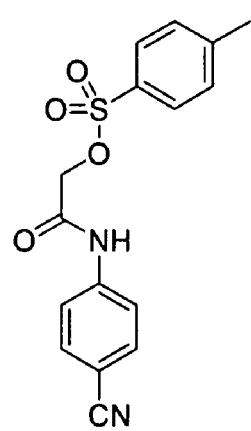
FIG. 32 shows the chemical structure of the compound BG3006B, an analog of S3I-201.
Figure 33:
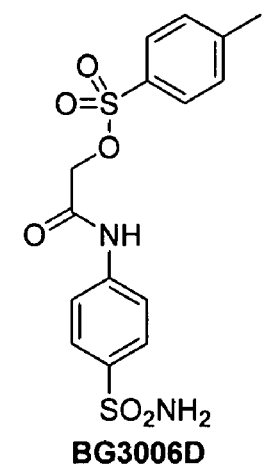
FIG. 33 shows the chemical structure of the compound BG3006D, an analog of S3I-201.
Figure 34:
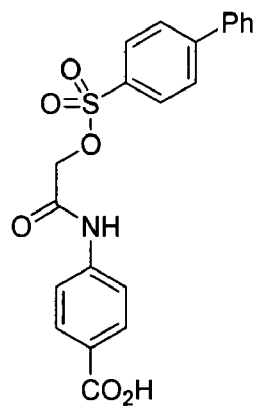
FIG. 34 shows the chemical structure of the compound BG3009, an analog of S3I-201.
Figure 35:
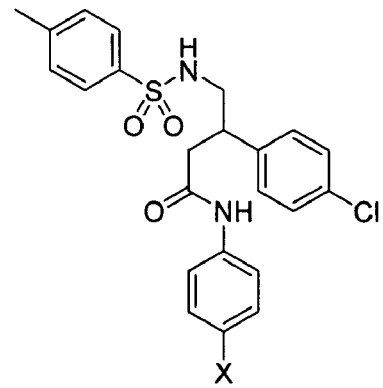
FIG. 35 shows the chemical structure of compounds RPM381, RPM384, and RPM385, wherein X=H, $CO_2Et$, and $CO_2H$, respectively.
Figure 36:
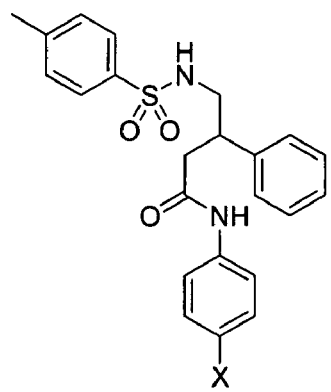
FIG. 36 shows the chemical structure of compounds RPM405 and RPM411, wherein X=$CO_2Et$ and $CO_2H$, respectively.
Figure 37:
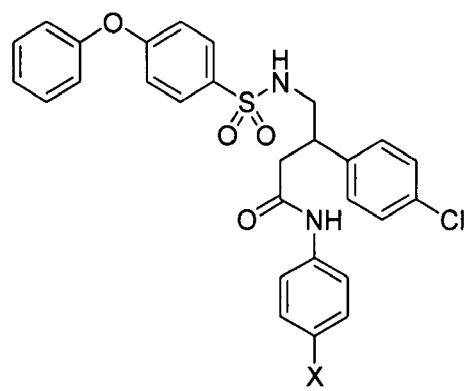
FIG. 37 shows the chemical structure of compounds RPM407 and RPM412, wherein X=$CO_2Et$ and $CO_2H$, respectively.
Figure 38:
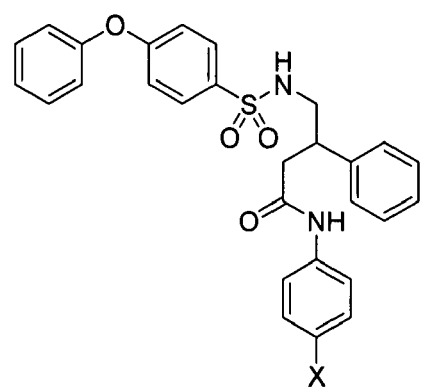
FIG. 38 shows the chemical structure of compounds RPM408 and RPM410, wherein X=$CO_2Et$ and $CO_2H$, respectively.
Figure 39:
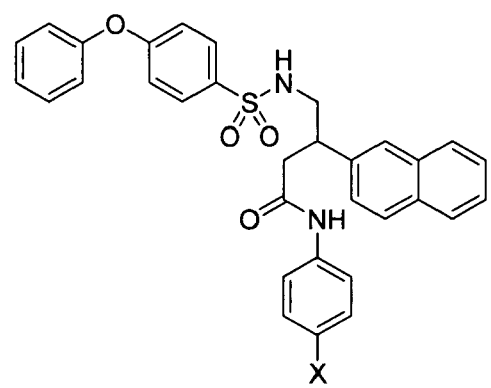
FIG. 39 shows the chemical structure of compounds RPM415 and RPM416, wherein X=$CO_2Et$ and $CO_2H$, respectively.
Figure 40:
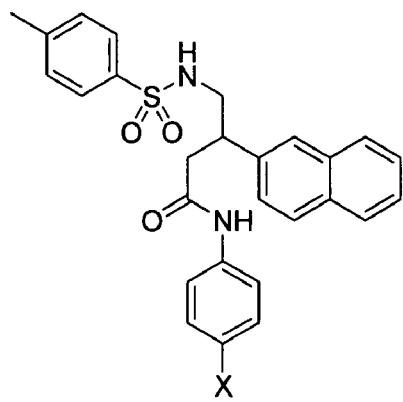
FIG. 40 shows the chemical structure of compounds RPM418 and RPM418-A, wherein X=$CO_2Et$ and $CO_2H$, respectively.
Figure 41:
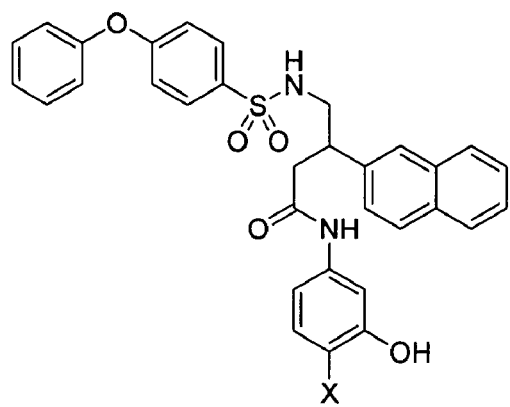
FIG. 41 shows the chemical structure of compound RPM427, wherein X=$CO_2H$.
Figure 42:
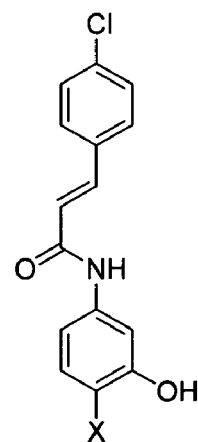
FIG. 42 shows the chemical structure of compound, RPM431, wherein X=$CO_2Me$.
Figure 43:
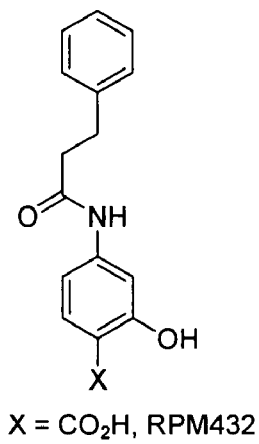
FIG. 43 shows the chemical structure of compound RPM432, wherein X=$CO_2H$.
Figure 44:
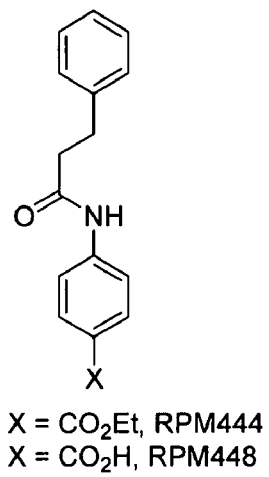
FIG. 44 shows the chemical structure of compounds RPM444 and RPM448, wherein X=$CO_2Et$ and $CO_2H$, respectively.
Figure 45:
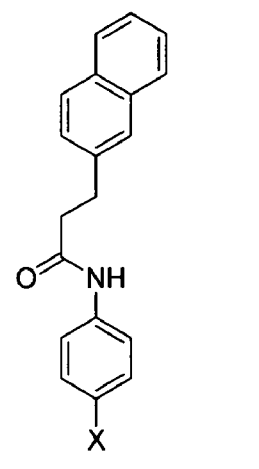
FIG. 45 shows the chemical structure of compounds RPM445 and RPM447, wherein X=$CO_2Et$ and X=$CO_2H$, respectively.
Figure 46:
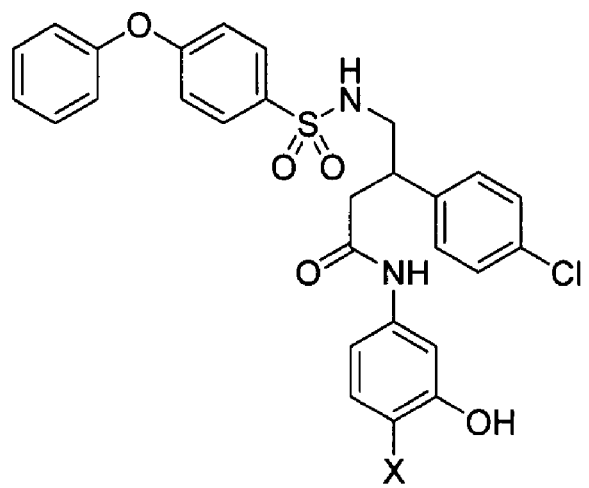
FIG. 46 shows the chemical structure of compound RPM452, wherein X=$CO_2H$.
Figure 47:
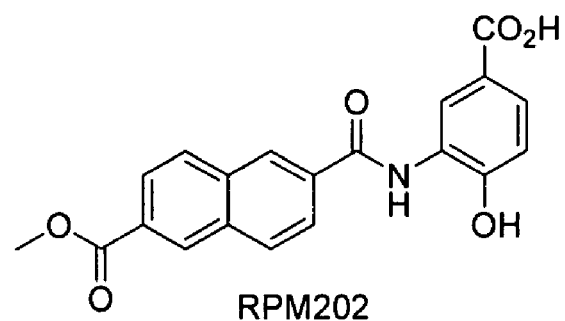
FIG. 47 shows the chemical structure of compounds RPM202.

The compounds of the present invention include all hydrates and salts of the compounds shown in FIGS. 7-9 (NSC 74859 (S3I-201), NSC 59263, NSC 42067), FIGS. 10-12A-D (Formulas A, B, C, D, E, and F), FIGS. 48-51 (NSC 42067, NSC 75912, NSC 11421 NSC 91529, and NSC 263435), or FIGS. 13-47 (e.g., HL2-006-1, HL2-006-2, HL2-006-3, HL2-006-4, HL2-006-5, HL2-011-1, HL2-011-2, HL2-011-3, HL2-011-4, HL2-011-5, BG2069-1, HL2-011-6, HL2-011-7, HL2-005, HL2-003, BG2066, BG2074, BG3004, BG3006A, BG3006B, BG3006D, BG3009, RPM381, RPM384, RPM385, RPM405, RPM411, RPM407, RPM412, RPM408, RPM410, RPM415, RPM416, RPM418, RPM418-A, RPM427, RPM431, RPM432, RPM444, RPM448, RPM445, RPM447, RPM452, and RPM202), and listed in Tables 4 and 5, or of their analogs, that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of compounds (e.g., Stat3 inhibitors) may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As used herein, the term "analogs" refers to compounds which are substantially the same as another compound but which may have been modified by, for example, adding side groups, oxidation or reduction of the parent structure. Analogs of the Stat3 inhibitors shown in FIGS. 7-9 (e.g., NSC 74859 (S3I-201), NSC 59263, and NSC 42067) FIGS. 49-52 (NSC 42067, NSC 75912, NSC 11421 NSC 91529, and NSC 263435), and other compounds disclosed herein can be readily prepared using commonly known standard reactions. These standard reactions include, but are not limited to, hydrogenation, alkylation, acetylation, and acidification reactions. Chemical modifications can be accomplished by those skilled in the art by protecting all functional groups present in the molecule and deprotecting them after carrying out the desired reactions using standard procedures known in the scientific literature (Greene, T. W. and Wuts, P. G. M. "Protective Groups in Organic Synthesis" John Wiley & Sons, Inc. New York. 3rd Ed. pg. 819, 1999; Honda, T. et al. *Bioorg. Med. Chem. Lett.,* 1997, 7:1623-1628; Honda, T. et al. *Bioorg. Med. Chem. Lett.,* 1998, 8:2711-2714; Konoike, T. et al. *J Org. Chem.,* 1997, 62:960-966; Honda, T. et al. *J. Med. Chem.,* 2000, 43:4233-4246; each of which are hereby incorporated herein by reference in their entirety). Analogs exhibiting the desired biological activity (such as induction of apoptosis, cytotoxicity, cytostaticity, induction of cell cycle arrest, etc.) can be identified or confirmed using cellular assays or other in vitro or in vivo assays. For example, assays that detect inhibition of Stat3 activation, $G_2/M$ cell cycle arrest, and/or reduction of tumor growth may be utilized.

It will be appreciated that the compounds of the invention can contain one or more asymmetrically substituted carbon atoms (i.e., carbon centers). The presence of one or more of the asymmetric centers in an analog of the invention, can give rise to stereoisomers, and in each case, the invention is to be understood to extend to all such stereoisomers, including enantiomers and diastereomers, and mixtures including racemic mixtures thereof.

FIGS. 12A-12D show formulas C-F, respectively, describing compounds of the invention. In FIGS. 12A-12D, the XNH groups have a transposed arrangement (NHX) with respect to one another.

Referring to FIGS. 12A-12D, $R_1$ and $R_2$, if present, can be an aliphatic or aromatic group; X, if present =CO, $SO_2$, CONH, or alkyl; Z, if present, is alkyl; and phosphate mimic=that shown in FIGS. 10 and 11, e.g., $CO_2H$, $SO_3H$, $PO_3H$, $NO_2$, $CH_2CO_2H$, $CF_2CO_2H$, or $CF(CO_2H)_2$ tetrazole. Preferably, $R_2$ is a hydrophobic group or part of a hydrophobic group. In one embodiment, $R_1$, if present, is H, alkyl, alkenyl, cycloalkyl, heterocycloalkyl, cylcoalkenyl, heterocycloalkenyl, acyl, and aryl, any of which may be optionally substituted; and $R_2$, if present is H, alkyl, alkenyl, cycloalkyl, heterocycloalkyl, cylcoalkenyl, heterocycloalkenyl, acyl, and aryl, any of which may be optionally substituted. In a preferred embodiment, $R_1$, if present, is aryl, substituted aryl, heteroaryl or alkyl; and $R_2$, if present is a hydrophobic group such as aryl, substituted aryl, heteroaryl or alkyl.

The term "alkyl group" is intended to mean a group of atoms derived from an alkane by the removal of one hydrogen atom. Thus, the term includes straight or branched chain alkyl moieties including, for example, methyl, ethyl, propyl, isopropyl, butyl, tert-butyl, pentyl, hexyl, and the like. Preferred alkyl groups contain from 1 to about 14 carbon atoms ($C_{1-14}$ alkyl).

The term "aryl group" is intended to mean a group derived from an aromatic hydrocarbon by removal of a hydrogen from the aromatic system. Preferred aryl groups contain phenyl or substituted phenyl groups. Thus, the term "aryl" includes an aromatic carbocyclic radical having a single ring or two condensed rings. This term includes, for example, phenyl or naphthyl.

The term "heteroaryl" refers to aromatic ring systems of five or more atoms (e.g., five to ten atoms) of which at least one atom is selected from O, N and S, and includes for example furanyl, thiophenyl, pyridyl, indolyl, quinolyl and the like.

The term "acyl group" is intended to mean a group having the formula RCO—, wherein R is an alkyl group or an aryl group.

The term "alkenyl" refers to a straight or branched chain alkyl moiety having two or more carbon atoms (e.g., two to six carbon atoms, $C_{2-6}$ alkenyl) and having in addition one double bond, of either E or Z stereochemistry where applicable. This term would include, for example, vinyl, 1-propenyl, 1- and 2-butenyl, 2-methyl-2-propenyl, etc.

The term "cycloalkyl" refers to a saturated alicyclic moiety having three or more carbon atoms (e.g., from three to six carbon atoms) and which may be optionally benzofused at any available position. This term includes, for example, cyclopropyl, cyclobutyl, cyclopentyl, cyclohexyl, indanyl and tetrahydronaphthyl.

The term "heterocycloalkyl" refers to a saturated heterocyclic moiety having three or more carbon atoms (e.g., from three to six carbon atoms) and one or more heteroatom from the group N, O, S (or oxidized versions thereof) and which may be optionally benzofused at any available position. This term includes, for example, azetidinyl, pyrrolidinyl, tetrahydrofuranyl, piperidinyl, indolinyl and tetrahydroquinolinyl.

The term "cycloalkenyl" refers to an alicyclic moiety having three or more carbon atoms (e.g., from three to six carbon atoms) and having in addition one double bond. This term includes, for example, cyclopentenyl or cyclohexenyl.

The term "heterocycloalkenyl" refers to an alicyclic moiety having from three to six carbon atoms and one or more heteroatoms from the group N, O, S (or oxides thereof) and having in addition one double bond. This term includes, for example, dihydropyranyl.

The term "halogen" means a halogen of the periodic table, such as fluorine, chlorine, bromine, or iodine.

The term "optionally substituted" means optionally substituted with one or more of the aforementioned groups (e.g., alkyl, aryl, heteroaryl, acyl, alkenyl, cycloalkyl, heterocycloalkyl, cycloalkenyl, heterocycloalkenyl, or halogen), at any available position or positions.

Specifically, "alkyl" can include, for example, methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl or pentadecyl; "alkenyl" can include vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradeceny, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, or 14-pentadecenyl; "alkoxy" can include methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy; "alkanoyl" can include acetyl, propanoyl, butanoyl, pentanoyl, hexanoyl, heptanoyl, octanoyl, nonanoyl, decanoyl, undecanoyl, dodecanoyl, tridecanoyl, tetradecanoyl, or pentadecanoyl; "cycloalkyl" can include cyclopropyl, cyclobutyl, cyclopentyl, cyclohexyl, cycloheptyl, or cyclooctyl, for example; "aryl" can include phenyl, indenyl, 5,6,7,8-tetrahydronaphthyl, or naphthyl, for example; and "heteroaryl" can include furyl, imidazolyl, tetrazolyl, pyridyl, (or its N-oxide), thienyl, pyrimidinyl (or its N-oxide), indolyl, or quinolyl (or its N-oxide), for example.

The compounds of the invention are useful for various non-therapeutic and therapeutic purposes. The compounds (e.g., Stat3 inhibitors) may be used for reducing aberrant cell growth in animals and humans. Because of such anti-proliferative properties of the compounds, they are useful in reducing unwanted cell growth in a wide variety of settings including in vitro and in vivo. In addition to their use in treatment methods, the Stat3 inhibitors of the invention are useful as agents for investigating the role of Stat3 in cellular metabolism, and controlling Stat3-mediated malignant or non-malignant cell growth in vitro or in vivo. They are also useful as standards and for teaching demonstrations.

Therapeutic application of the compounds and compositions comprising them can be accomplished by any suitable therapeutic method and technique presently or prospectively known to those skilled in the art. Further, the compounds of the invention can be used as starting materials or intermediates for the preparation of other useful compounds and compositions.

Compounds of the invention (e.g., Stat3 inhibitors) may be locally administered at one or more anatomical sites, such as sites of unwanted cell growth (such as a tumor site, e.g., injected or topically applied to the tumor), optionally in combination with a pharmaceutically acceptable carrier such as an inert diluent. Compounds of the invention may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the Stat3 inhibitor may be incorporated into sustained-release preparations and devices.

The active agent (compounds of the invention) may also be administered intravenously or intraperitoneally by infusion or injection. Solutions of the active agent can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds of the invention which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating the compounds of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds may be applied in pure-form, i.e., when they are liquids. However, it will generally be desirable to administer them topically to the skin as compositions, in combination with a dermatologically acceptable carrier, which may be a solid or a liquid.

The compounds of the subject invention can be applied topically to a subject's skin to reduce the size (and may include complete removal) of malignant or benign growths. The compounds of the invention can be applied directly to the growth. Preferably, the compound is applied to the growth in a formulation such as an ointment, cream, lotion, solution, tincture, or the like. Drug delivery systems for delivery of pharmacological substances to dermal lesions can also be used, such as that described in U.S. Pat. No. 5,167,649 (Zook).

Useful solid carriers include finely divided solids such as talc, clay, microcrystalline cellulose, silica, alumina and the like. Useful liquid carriers include water, alcohols or glycols or water-alcohol/glycol blends, in which the Stat3 inhibitor can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the Stat3 inhibitors to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Accordingly, the present invention includes a pharmaceutical composition comprising a compound of the invention in combination with a pharmaceutically acceptable carrier. Pharmaceutical compositions adapted for oral, topical or parenteral administration, comprising an amount of a compound of the invention constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Depending upon the disorder or disease condition to be treated, a suitable dose(s) may be that amount that will reduce proliferation or growth of the target cell(s). In the context of cancer, a suitable dose(s) is that which will result in a concentration of the active agent (the compound of the invention) in cancer tissue, such as a malignant tumor, which is known to achieve the desired response. The preferred dosage is the amount which results in maximum inhibition of cancer cell growth, without unmanageable side effects. Administration of a compound of the invention can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds of the invention based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such human and non-human species.

Patients in need of treatment using the methods of the present invention can be identified using standard techniques known to those in the medical or veterinary professions, as appropriate.

As used herein, the terms "cancer" and "cancerous" refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer types that may potentially be treated using the Stat3 inhibitors of the present invention are also listed in Table 1.

TABLE 1

Examples of Cancer Types

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sézary Syndrome |
| Brain Tumor, Childhood | |
| Breast Cancer | Lymphoma, Hodgkin's, Adult |

TABLE 1-continued

Examples of Cancer Types

Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sézary Syndrome
Testicular Cancer
Thymoma, Childhood
Thymoma and Thymic Carcinoma
Thyroid Cancer
Thyroid Cancer, Childhood
Transitional Cell Cancer of the Renal Pelvis and Ureter
Trophoblastic Tumor, Gestational
Unknown Primary Site, Carcinoma of, Adult
Unknown Primary Site, Cancer of, Childhood
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell Cancer
Retinoblastoma
Rhabdomyosarcoma, Childhood
Salivary Gland Cancer
Salivary Gland Cancer, Childhood
Sarcoma, Ewing's Family of Tumors
Sarcoma, Kaposi's
Sarcoma, Soft Tissue, Adult
Sarcoma, Soft Tissue, Childhood
Sarcoma, Uterine
Sezary Syndrome

TABLE 1-continued

Examples of Cancer Types

Unusual Cancers of Childhood
Ureter and Renal Pelvis, Transitional Cell Cancer
Urethral Cancer
Uterine Cancer, Endometrial
Uterine Sarcoma
Vaginal Cancer
Visual Pathway and Hypothalamic Glioma, Childhood
Vulvar Cancer
Waldenström's Macroglobulinemia
Wilms' Tumor
Skin Cancer (non-Melanoma)
Skin Cancer, Childhood As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MRI), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site. The treatment methods of the invention can be utilized for early, middle, or late stage disease, and acute or chronic disease. In some embodiments, the tumor is characterized as one exhibiting aberrant activation of Stat3.

According to the method of the subject invention, a compound of the invention can be administered to a patient by itself, or co-administered with one or more other agents such as another compound of the invention, or a different agent or agents. Co-administration can be carried out simultaneously (in the same or separate formulations) or consecutively. Furthermore, according to the method of the subject invention, compounds of the invention can be administered to a patient as adjuvant therapy. For example, compounds can be administered to a patient in conjunction with chemotherapy.

Thus, the compounds of the invention, whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the compounds of the invention, or act towards preventing any potential side effects which may be posed as a result of administration of the compounds. The Stat3 inhibitors of the subject invention can be conjugated to a therapeutic agent, as well.

Additional agents that can be co-administered to target cells in vitro or in vivo, such as in a patient, in the same or as a separate formulation, include those that modify a given biological response, such as immunomodulators. For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered. In one embodiment, the methods and compositions of the invention incorporate one or more agents selected from the group consisting of anti-cancer agents, cytotoxic agents, chemotherapeutic agents, anti-signaling agents, and anti-angiogenic agents.

EXEMPLIFIED EMBODIMENTS

1. An isolated compound having the structure of S3I-201 (shown in FIG. 7), NSC-59263 (shown in FIG. 8), NSC-42067 (shown in FIG. 9), Formula A (shown in FIG. 10), Formula B (shown in FIG. 11), Formula C (shown in FIG. 12A), Formula D (shown in FIG. 12B), Formula E, shown in FIG. 12C, Formula F (shown in FIG. 12D), NSC 75912 (shown in FIG. 50), NSC 11421 (shown in FIG. 49), NSC 91529 (shown in FIG. 51), NSC 263435 (shown in FIG. 48), HL2-006-1 (shown in FIG. 13), HL2-006-2 (shown in FIG. 14), HL2-006-3 (shown in FIG. 15), HL2-006-4 (shown in FIG. 16), HL2-006-5 (shown in FIG. 17), HL2-011-1 (shown in FIG. 18), HL2-011-2 (shown in FIG. 19), HL2-011-3 (shown in FIG. 20), HL2-011-4 (shown in FIG. 21), HL2-011-5 (shown in FIG. 22), BG2069-1 (shown in FIG. 23), HL2-011-6 (shown in FIG. 24), HL2-011-7 (shown in FIG. 25), HL2-005 (shown in FIG. 26), HL2-003 (shown in FIG. 27), BG2066 (shown in FIG. 28), BG2074 (shown in FIG. 29), BG3004 (shown in FIG. 30), BG3006A (shown in FIG. 31), BG3006B (shown in FIG. 32), BG3006D (shown in FIG. 33), BG3009 (shown in FIG. 34), RPM381 (shown in FIG. 35), RPM384 (shown in FIG. 35), RPM385 (shown in FIG. 35), RPM405 (shown in FIG. 36), RPM411 (shown in FIG. 36), RPM407 (shown in FIG. 37), RPM412 (shown in FIG. 37), RPM408 (shown in FIG. 38), RPM410 (shown in FIG. 38), RPM415 (shown in FIG. 39), RPM416 (shown in FIG. 39), RPM418 (shown in FIG. 40), RPM418-A (shown in FIG. 40), RPM427 (shown in FIG. 41), RPM431 (shown in FIG. 42), RPM432 (shown in FIG. 43), RPM444 (shown in FIG. 44) RPM448 (shown in FIG. 44), RPM445 (shown in FIG. 45), RPM447 (shown in FIG. 45), RPM452 (shown in FIG. 46), RPM202 (shown in FIG. 47), a compound listed in Table 4, a compound listed in Table 5, or a pharmaceutically acceptable salt or analog of any of the foregoing.

2. A pharmaceutical composition comprising at least one isolated compound selected from selected from embodiment 1; and a pharmaceutically acceptable carrier.

3. The composition of embodiment 2, wherein the compound is S3I-201.

4. The composition of embodiment 2 or 3, further comprising an additional anti-cancer agent.

5. The composition of any of embodiments 2-4, further comprising an agent selected from the group consisting of an antioxidant, free radical scavenging agent, peptide, growth factor, antibiotic, bacteriostatic agent, immunosuppressive, anticoagulant, buffering agent, anti-inflammatory agent, anti-angiogenic agent, anti-pyretic, time-release binder, anesthetic, steroid, and corticosteroid.

6. The composition of any of embodiments 2-5, comprising more than one of said compounds.

7. A method of treating a proliferation disorder in a subject, comprising administering an effective amount of at least one compound of embodiment 1 to the subject.

8. The method of embodiment 7, wherein said administering comprising administering an effective amount of S3I-201 to the subject.

9. The method of embodiment 7 or 8, wherein the proliferation disorder is cancer.

10. The method of any of embodiments 7-9, wherein the compound is administered locally at the site of a tumor.

11. The method of any of embodiments 7-10, wherein the proliferation disorder is cancer, and wherein the subject is suffering from a tumor and the compound inhibits growth of the tumor.

12. The method of embodiment 7 or 8, wherein the proliferation disorder is a non-malignant disease characterized by aberrant Stat3 activation of cells.

13. The method of any of embodiments 7-12, wherein the compound is administered locally at the site of the proliferation disorder.

14. The method of any of embodiments 7-9, wherein the subject is not suffering from the proliferation disorder, and wherein the compound is administered to delay onset of the proliferation disorder.

15. The method of any of embodiments 7-14, wherein the route of administration is selected from the group consisting of intravenous, intramuscular, oral, and intra-nasal.

16. The method of any of embodiments 7-15, wherein the subject is human.

17. The method of any of embodiments 7-15, wherein the subject is a non-human mammal.

18. The method of any of embodiments 7-13 or 15-17, further comprising identifying the subject as one suffering from the proliferation disorder.

19. The method of embodiment 8, wherein the subject is suffering from a tumor and wherein said administering comprises administering S3I-201 at the site of the tumor.

20. A method of suppressing the growth of, or inducing apoptosis in, malignant cells, the method comprising contacting the cells with an effective amount of at least one compound of embodiment 1.

21. The method of embodiment 20, wherein said administering is carried out in vitro.

22. The method of embodiment 20, wherein said administering is carried out in vivo.

23. The method of any of embodiments 20-22, wherein the cells are mammalian cancer cells.

24. The method of any of embodiments 20-23, wherein the cells consist essentially of human breast cancer cells.

25. The method of any of embodiments 20-24, wherein said contacting comprises contacting the cells with an effective amount of S3I-201.

26. A method of inhibiting constitutive activation of Stat3 in cells, comprising contacting the cells with an effective amount of at least one compound of embodiment 1.

27. The method of embodiment 26, wherein said administering is carried out in vitro.

28. The method of embodiment 26, wherein said administering is carried out in vivo.

29. The method of embodiment 27 or 28, wherein said contacting comprises contacting the cells with an effective amount of S3I-201.

30. The method of any of embodiments 26-29, wherein the cells are cancer cells.

31. The method of any of embodiments 26-30, wherein the cells consist essentially of human breast cancer cells.

32. A method of preventing Stat3 dimerization in a mammalian cell, the method comprising contacting the cell with an effective amount of at least compound of embodiment 1.

33. The method of embodiment 32, wherein said contacting comprises contacting the cell with an effective amount of S3I-201.

34. A method of disrupting Stat3-DNA binding or Stat5-DNA binding, the method comprising contacting the Stat3 or Stat5 with an effective amount of at least one compound of embodiment 1.

35. The method of embodiment 34, wherein said contacting comprises contacting the Stat3 or Stat5 with an effective amount of S3I-201.

36. An in-vitro screening test for presence of malignant cells in a mammalian tissue, the test comprising:
   obtaining a sample containing viable cells of said tissue;
   culturing said sample under conditions promoting growth of the viable cells contained therein;
   treating the cultured sample with a compound; and
   analyzing the treated sample by a method effective to determine percent apoptosis of cells as an indicator of presence of malignant cells in the sample, wherein the compound is at least one compound of embodiment 1.

37. The screening test of embodiment 36, wherein said treating comprising contacting the cells with S3I-201.

38. A method of identifying inhibitors of constitutive Stat3 activation, Stat3-DNA binding, Stat5-DNA binding, and/or Stat3 dimerization, the method comprising selecting a compound having a structure of Formula A, B, C, D, E, or F (shown in FIGS. 10-12A-D); and determining whether the compound inhibits constitutive Stat3 activation, disrupts Stat3-DNA binding, disrupts Stat5-DNA binding, prevents Stat3 dimerization, or determining two or more of the foregoing.

39. The method of embodiment 38, wherein the compound is not one selected from embodiment 1.

40. A method of identifying anti-cancer agents, the method comprising selecting a compound having a structure of Formulas A, B, C, D, E, or F (shown in FIGS. 10-12A-D); and determining whether the compound inhibits the growth of cancer cells in vitro or in vivo.

41. The method of embodiment 41, wherein the compound is not one selected from embodiment 1.

Assays known in the art and/or disclosed herein may be used to evaluate cell apoptosis and/or inhibition of Stat signaling in carrying out the in vitro screening test and methods set forth in the above embodiments, such as assays for inhibition of dimerization (see, for example, Schust, J., Berg, T., *Analytical Biochemistry*, 2004, 330(1):114-118, which is incorporated by reference herein in its entirety); and assays for inhibition of DNA binding (see, for example, Turkson J. et al., *J. Biol. Chem.*, 2001, 276(48):45443-45455, which is incorporated by reference herein in its entirety). Likewise, such assays may be used to confirm the desired biological activity possessed by analogs of the invention.

DEFINITIONS

As used herein, the terms "treat" or "treatment" refer to both therapeutic treatment and prophylactic or preventative measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a compound of the invention may include reduction of undesirable cell proliferation, and/or induction of apoptosis and cytotoxicity. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition (e.g., proliferation disorder) prior to administration of the Stat3 inhibitor of the invention.

As used herein, the term "(therapeutically) effective amount" refers to an amount of the compound of the invention or other agent (e.g., a drug) effective to treat a disease or disorder in a mammal. In the case of cancer or other proliferation disorder, the therapeutically effective amount of the agent may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; reduce Stat3 signaling in the target cells (such as by inhibiting the binding of DNA and Stat3), and/or relieve, to some extent, one or more of the symptoms associated with the cancer. To the extent the administered compound prevents growth of and/or kills existing cancer cells, it may be cytostatic and/or cytotoxic. For cancer therapy, efficacy can, for example, be measured by assessing the time to disease progression (TTP) and/or determining the response rate (RR).

As used herein, the term "growth inhibitory amount" of the compound of the invention refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

The terms "cell" and "cells" are used interchangeably herein and are intended to include either a single cell or a plurality of cells, in vitro or in vivo, unless otherwise specified.

As used herein, the term "anti-cancer agent" refers to a substance or treatment that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). In some embodiments, the anti-cancer agent is a ras antagonist.

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Examples of chemotherapeutic agents that may be used in conjunction with the compounds of the invention are listed in Table 2. In a preferred embodiment, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

TABLE 2

Examples of Chemotherapeutic Agents

| | |
|---|---|
| 13-cis-Retinoic Acid | Mylocel |
| 2-Amino-6- | Letrozole |
| Mercaptopurine | Neosar |
| 2-CdA | Neulasta |
| 2-Chlorodeoxyadenosine | Neumega |
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |

TABLE 2-continued

Examples of Chemotherapeutic Agents

| | |
|---|---|
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte-colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

As used herein, the term "Stat" refers to signal transducers and activators of transcription, which represent a family of proteins that, when activated by protein tyrosine kinases in the cytoplasm of the cell, migrate to the nucleus and activate gene transcription. Examples of mammalian STATs include STAT1, STAT2, STAT3, STAT4, STAT5a, STAT5b, and STAT6.

As used herein, the term "signaling" and "signaling transduction" represents the biochemical process involving transmission of extracellular stimuli, via cell surface receptors through a specific and sequential series of molecules, to genes in the nucleus resulting in specific cellular responses to the stimuli.

As used herein, the term "constitutive activation," as in the constitutive activation of the STAT pathway, refers to a condition where there is an abnormally elevated level of tyrosine phosphorylated STAT3 within a given cell(s), e.g., cancer cells, as compared to a corresponding normal (e.g., non-cancer or non-transformed) cell. Constitutive activation of STAT3 has been exhibited in a large variety of malignancies, including, for example, breast carcinoma cell lines; primary breast tumor specimens; ovarian cancer cell lines and tumors; multiple myeloma tumor specimens; and blood malignancies, such as acute myelogenous leukemia, as described in published PCT international application WO 00/44774 (Jove, R. et al.), the disclosure of which is incorporated herein by reference in its entirety.

Methods for determining whether a human or non-human mammalian subject has abnormally high levels of constitutively-activated Stat3 are known in the art and are described, for example, in U.S. patent publication 2004-0138189-A1 and PCT publication 02/078617 A, each of which are incorporated herein by reference in their entirety. Optionally, the methods of the invention further comprise identifying a patient suffering from a condition (e.g., cancer) associated with an abnormally elevated level of tyrosine phosphorylated STAT3, or determining whether the cancer cells can be characterized as having abnormally elevated levels of tyrosine phosphorylated Stat3.

As used herein, the term "pharmaceutically acceptable salt or prodrug" is intended to describe any pharmaceutically acceptable form (such as an ester, phosphate ester, salt of an ester or a related group) of a compound of the invention, which, upon administration to a subject, provides the mature or base compound (e.g., a Stat3-inhibitory compound). Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "pharmaceutically acceptable esters" as used herein, unless otherwise specified, includes those esters of one or more compounds, which are, within the scope of sound medical judgment, suitable for use in contact with the tissues of hosts without undue toxicity, irritation, allergic response and the like, are commensurate with a reasonable benefit/risk ratio, and are effective for their intended use.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state.

As used in this specification, the singular forms "a", "an", and "the" include plural reference unless the context clearly dictates otherwise. Thus, for example, a reference to "a compound" includes more than one such compound. A reference to "a Stat3 inhibitor" includes more than one such inhibitor, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

Following are examples that illustrate materials, methods, and procedures for practicing the invention. The examples are illustrative and should not be construed as limiting.

Materials and Methods

Cells and reagents. Normal mouse fibroblasts (NIH3T3) and their counterparts transformed by v-Src (NIH3T3/v-Src), v-Ras (NIH3T3/v-Ras) or overexpressing the human EGF receptor (NIH3T3/hEGFR), and the human breast cancer (MDA-MB-231, MDA-MB-435, MDA-MB-453, and MDA-MB-468) cells have all been previously reported (Turkson, J. et al. *J. Biol. Chem.*, 2001, 276:45443-45455; Yu, C. L. et al. *Science*, 1995, 269:81-83; Garcia, R. et al. *Oncogene*, 2001, 20:2499-2513; Johnson, P. J. et al. *Mol. Cell. Biol.*, 1985, 5:1073-1083). Cells were grown in Dulbecco's modified Eagle's medium (DMEM) containing 10% heat-inactivated fetal bovine serum. Antibodies C-136 and E23X for Stat1, C20 and C20X for Stat3 and L-20 and L-20X for Stat5A were obtained from Santa Cruz Biotechnology, Santa Cruz, Calif., and polyclonal anti-Src and anti-phosphoSrc antibodies from Cell Signaling Technology, Danvers, Mass.

Transient transfection of cells and treatment with compound. Twelve to twenty-four hours following seeding, normal mouse fibroblasts (NIH3T3) were transiently co-transfected with 4 µg each of pLucTKS3, pLucSRE, or β-Casein Luc and 4 µg pMvSrc and 100 ng β-galactosidase (for normalizing), or the human breast carcinoma MDA-MB-231 cells were transiently transfected with pRc/CMV-Stat3C (kindly provided by J. Bromberg and J. Darnell (Bromberg, J. F. et al. *Cell*, 1999, 98:295-303)), or with FLAG-tagged N-terminus of Stat3 (Stat3-NT) or FLAG-tagged Stat3 SH2 domain (ST3-SH2) (Zhang, T. et al. *J. Biol. Chem.*, 2002, 277:17556-175563), or mock transfected for 4 hours using Lipofectamine plus (Invitrogen, Carlsbad, Calif.) and following the manufacturer's protocol. Twenty-four hours after transfection, cells were untreated (0.05% DMSO) or treated with S3I-201 (100 µM) for an additional 24 hours, harvested and cytosolic extracts prepared for luciferase assay, as previously done (Turkson, J. et al. *J. Biol. Chem.*, 2001, 276: 45443-45455; Turkson, J. et al. *Mol. Cell. Biol.*, 1998, 18:2545-2552) or cells were analyzed by Annexin V binding and Flow Cytometry.

Cytosolic extracts and cell lysates preparation, luciferase and β-galactosidase assay. Cytosolic extract preparation from mammalian cells for luciferase and β-gal assays, and from recombinant baculovirus-infected Sf9 cells to obtain Stat1, Stat3, and Stat5 monomers, and Src proteins are as described previously (Turkson, J. et al. *J. Biol. Chem.*, 2001, 276: 45443-45455; Turkson, J. et al. *Mol. Cell. Biol.*, 1998, 18:2545-2552; Zhang, Y. et al. *J. Biol. Chem.*, 2000, 275: 24935-24944). Luciferase assays were done according to the supplier's (Promega, Madison, Wis.) manual and measured with a luminometer. β-gal assays were performed on lysates from transfected cells, as previously reported (Turkson, J. et al. *J. Biol. Chem.*, 2001, 276:45443-45455; Turkson, J. et al. *Mol. Cell. Biol.*, 1998, 18:2545-2552).

Nuclear extract preparation, gel shift assays and densitometric analysis. Nuclear extract preparations and electrophoretic mobility shift assay (EMSA) were carried out as previously described (Yu, C. L. et al. *Science*, 1995, 269:81-83; Garcia, R. et al. *Oncogene*, 2001, 20:2499-2513; Turkson, J. et al. *Mol. Cell. Biol.*, 1998, 18:2545-2552). The $^{32}$P-labeled oligonucleotide probes used were hSIE (high affinity sis-inducible element from the c-fos gene, m67 variant, 5'-AGCTTCATTTCCCGTAAATCCCTA) (SEQ ID NO:3) that binds Stat1 and Stat3 (Garcia, R. et al. *Oncogene*, 2001, 20:2499-2513; Wagner, M. et al. *Pancreas*, 1999, 19:370-376) and MGFe (mammary gland factor element from the bovine β-casein gene promoter, 5'-AGATTTCTAGGAAT-TCAA) (SEQ ID NO:4) for Stat1 and Stat5 binding (Gouilleux, F. et al. *Endocrinology*, 1995, 136:5700-5708; Seidel, H. M. et al. *Proc. Natl. Acad. Sci. USA*, 1995, 92:3041-3045). Except where indicated, nuclear extracts were pre-incubated with compound for 30 minutes at room temperature prior to incubation with the radiolabeled probe. Bands corresponding to DNA-binding activities were scanned and quantified for each concentration of compound and plotted as percent of control (vehicle) against concentration of compound, from which the $IC_{50}$ values were derived, as previously reported (Turkson, J. et al. *J. Biol. Chem.*, 2001, 276:45443-45455; Turkson, J. et al. *J Biol. Chem.*, 2005, 280:32979-32988).

Immunoprecipitation (IP) and Western blotting. Whole-cell lysates and tumor tissue lysates from pulverized tumor tissue were prepared in boiling SDS sample loading buffer to extract total proteins, as previously described (Turkson, J. et al. *Mol Cancer Ther*, 2004, 3:261-269; Turkson, J. et al. *Mol. Cancer. Ther.*, 2004, 3:1533-1542; Turkson, J. et al. *J Biol. Chem.*, 2005, 280:32979-32988; Garcia, R. et al. *Oncogene*, 2001, 20:2499-2513). For IP, lysates were prepared from NIH3T3/v-Src mouse fibroblasts overexpressing the FLAG-tagged Stat3 (FLAG-ST3) and Stat3-YFP in the IP buffer (25 mM Tris-HCl, pH 7.2, 150 mM NaCl, 25 mM NaF, 0.5 mM Na orthovanadate, 20 mM PNPP, 1 mM benzamidine, 1 mM DTT, 1% Triton X-100, 2 µg/ml aprotinin, 2 µg/ml leupeptin, 1 µg/ml pepstatin, 100 µg/ml PMSF). FLAG-ST3 and Stat3-YFP were then immunoprecipitated by adding monoclonal anti-FLAG M2 (Sigma-Aldrich, St. Louis, Mo.) or anti-YFP (Santa Cruz) antibody and incubating at 4° C. overnight with gentle rocking. Protein A/G PLUS-Agarose (Santa Cruz) was added at 1:10 and incubated with rocking for 3 hours at 4° C. and centrifuged at 14,000 rpm at 4° C. for 30 seconds. Bead pellets were washed 5× in the IP buffer, equivalent volume of 3×SDS sample loading buffer added, vortexed, and boiled for 5 minutes. Equivalent amounts of total protein were electrophoresed on an SDS-7.5-15% polyacrylamide gel and transferred onto nitrocellulose membranes. Probing of nitrocellulose membranes with primary antibodies and detection of horseradish peroxidase-conjugated secondary antibodies by enhanced chemiluminescence (Amersham, Piscataway, N.J.) were performed, as described previously (Turkson, J. et al. *Mol Cancer Ther*, 2004, 3:261-269; Turkson, J. et al. *J Biol. Chem.*, 2005, 280:32979-32988; Garcia, R. et al. *Oncogene*, 2001, 20:2499-2513). The probes used were anti-cyclin D1, anti-Bcl-xL, anti-phosphoTyr-Stat3, anti-phospho-Shc, anti-Survivin, anti-Erk1/2, anti-phosphoTyr, 4G10 clone, and anti-β-actin (Cell Signaling Technology, Beverly, Mass.), anti-Stat3, anti-Stat5A, and anti-pErk1/2 (Santa Cruz), anti-Src (Cell Signaling Technology), anti-FLAG M2 (Sigma), and anti-YFP (Santa Cruz).

Lck-SH2 domain-phosphopeptide binding assay. In vitro ELISA study involving the Lck-SH2-GST protein and the conjugate pTyr peptide, biotinyl-ϵ-Ac-EPQpYEEIEL-OH (SEQ ID NO:2) (Bachem Bioscience, Pa.) was performed as previously described (Lee, T. R. and Lawrence, D. S. *J Med. Chem.*, 2000, 43:1173-1179). Briefly, 100 µl of biotinyl-ϵ-Ac-EPQpYEEIEL-OH (Bachem) (in 50 mM Tris, 150 mM NaCl, pH 7.5) was added to each well of a streptavidin-coated 96-well microtiter plates (Pierce, Rockford, Ill.) and incubated with shaking at 4° C. overnight. Then plates were rinsed with PBS-Tween 20 and then two times with 200 µl of BSA-T-PBS (0.2% BSA, 0.1% Tween 20, PBS). Then 50 µl of Lck-SH2-GST (Santa Cruz Biotechnology) fusion protein (6.4 ng/ml in BSA-T-PBS) was added to each well of the 96-well plate in the presence and absence of 50 µl of S3I-201 (for 30 and 100 µM final concentrations) and the plate was shaken at room temperature for 4 hours. After solutions were removed, each well was rinsed four times with BSA-T-PBS (200 µl) and 100 µl polyclonal rabbit anti-GST antibody (CHEMICON, Temecula, Calif.) (100 ng/ml in BSA-T-PBS) was added to each well, incubated at 4° C. overnight. Following washing with BSA-T-PBS, 100 µl of 200 ng/ml BSA-T-PBS horseradish peroxidase conjugated mouse anti-rabbit antibody (Amersham Biosciences) was added to each well and incubated for 45 minutes at room temperature. After 4 washing steps each with BSA-T-PBS and 3 washing steps each with PBS-T, 100 µl of peroxidase substrate (1-Step Turbo TMB-ELISA, Pierce) was added to each well and incubated for 5-15 minutes. Peroxidase reaction was stopped by adding 100 µl 1M sulfuric acid solution and absorbance was read at 450 nm with an ELISA plate reader.

Soft-agar colony formation assay. Colony formation assays were carried out in 6-well dishes, as described previously (Turkson, J. et al. *J. Biol. Chem.*, 2001, 276:45443-45455). Brie fly, each well contained 1.5 ml of 1% agarose in Dulbeco's modified Eagle's medium as the bottom layer and 1.5 ml of 0.5% agarose in Dulbeco's modified Eagle's medium containing 4000 or 6000 NIH3T3/v-Src or NIH3T3/v-Ras fibroblasts, respectively, as the top layer. Treatment with S3I-201 was initiated 1 day after seeding cells by adding 100 µl of medium with or without S3I-201, and repeating every 3 days, until large colonies were evident. Colonies were quantified by staining with 20 µl of 1 mg/ml iodonitrotetrazolium violet, incubating at 37° C. overnight, and counting the next day.

Measurement of apoptosis by Flow Cytometry. Proliferating cells were treated with or without S3I-201 for up to 48 hours. In some cases, cells were first transfected with Stat3C, ST3-NT, or ST3-SH2 domain or mock-transfected for 24 hours prior to treatment with compound for an additional 24-48 hours. Cells were then detached and analyzed by Annexin V binding (BD Biosciences, San Diego) according to the manufacturer's protocol and Flow Cytometry to quantify the percent apoptosis.

Mice and in vivo tumor studies. Six-week-old female athymic nude mice were purchased from Harlan (Indianapolis, Ind.) and maintained in the institutional animal facilities approved by the American Association for Accreditation of Laboratory Animal Care. Athymic nude mice were injected in the left flank area s.c. with 5×10⁶ human breast cancer MDA-MB-231 cells in 100 μL of PBS. After 5 to 10 days, tumors with a diameter of 3 mm were established. Animals were given S3I-201 i.v. at 5 mg/kg every 2 or 3 days for two weeks and monitored every 2 or 3 days. Animals were stratified so that the mean tumor sizes in all treatment were nearly identical. Tumor volume was calculated according to the formula $V=0.52 \times a^2 \times b$, where a, smallest superficial diameter, b, largest superficial diameter.

It should be understood that the examples and embodiments described herein are for illustrative purposes only and that various modifications or changes in light thereof will be suggested to persons skilled in the art and are to be included within the spirit and purview of this application.

Example 1

Computational Modeling and Virtual Screening

The computational modeling and virtual screening study used the GLIDE (Grid-based Ligand Docking from Energetics) software (Friesner, R. et al. *J. Med. Chem.*, 2004, 47:1739-1749; Halgren, T. et al. *J. Med. Chem.*, 2004, 47:1750-1759) (available from Schrödinger, L.L.C.) for the docking simulations, and relied on the X-ray crystal structure of the Stat3β homodimer bound to DNA (Becker, S. et al. *Nature*, 1998, 394:145-151) determined at 2.25 Å resolution (IBG1 in the Protein Databank). The modeling approach was used as a platform for structure-based virtual high throughput screening of the chemical libraries of the NCI Diversity Set (≈2,400 3D structures) and the NCI Plated Set (≈151,000 3D structures). For the virtual screening, DNA was removed and only one of the two monomers was employed (see FIGS. 1A and 1B). To validate the docking approach, the native pTyr peptide, APY*LKT (SEQ ID NO: 1), was extracted from the crystal structure of one of the monomers and docked to the other monomer, whereby GLIDE produced a docking mode that closely resembled the X-ray crystal structure (data not shown). Three-dimensional structures of compounds from the NCI's chemical libraries were downloaded from the NCI DTP website and processed with LigPrep (available from Schrödinger, L.L.C.) to produce 2,392 3D structures for the Diversity Set and 150,829 3D structures for the Plated Set. Then GLIDE 2.7 SP (Standard Precision mode) docked each chemical structure (for small-molecule) into the pTyr peptide binding site within the SH2 domain of the monomer in order to obtain the best docking mode and docking score.

For stronger interactions of small-molecules within the Stat3 SH2 domain relative to the native pTyr peptide, emphasis is placed on maintaining the critical atomic contacts that make the greatest contribution to the overall binding free energy. Strong hydrogen bonding and hydrophobic interactions within the SH2 domain are observed for compounds identified with good docking scores, which will be predicted to be strong binders to Stat3 and potent Stat3 inhibitors. The best score observed from the docking studies was −11.7 kcal/mol, relative to the native phosphopeptide sequence APY*LKT (SEQ ID NO:1) (scored as −11.9 kcal/mol). Typically, compounds receiving highly favorable scores (more negative values) have structural features that include sulfonyl, carboxyl and hydroxyl functional groups. For example, the current hit, S3I-201 (NSC 74859), contains all 3 groups (FIG. 7), and from the modeling data the carboxylate moiety of S3I-201 is predicted to interact with Ser613, Ser611, and Arg609, whereas the phenolic hydroxyl group interacts with Lys591 of the phosphotyrosine binding site of the Stat3 SH2 domain.

Example 2

Figures 1, 2C:
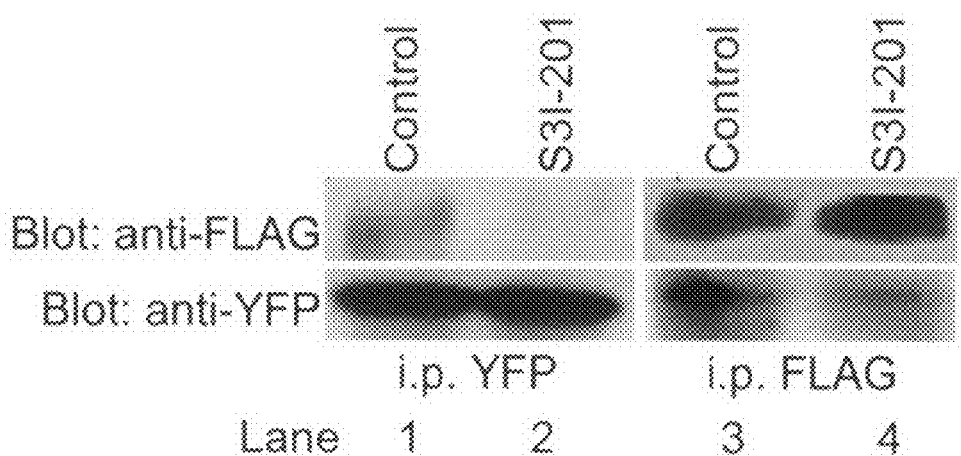
Figures 2, 2C:

Identification of a Novel Chemical Probe as an Inhibitor of Stat3 DNA-Binding Activity The best scoring compounds from the virtual screening studies were selected for experimental analysis using an in vitro Stat3 DNA-binding assay. Nuclear extracts containing activated STATs were incubated for 30 minutes with or without increasing concentrations of compounds prior to incubation with the radiolabeled hSIE probe that binds to Stat1 and to Stat3 or the MGFe probe that binds to Stat1 and to Stat5 and subjected to EMSA analysis, as described under "Materials and Methods". Results for the confirmed hit, S3I-201 (FIG. 7), show differential inhibition of DNA-binding activities of STATs. FIG. 2A, left panel shows potent inhibition of Stat3 DNA-binding activity by S3I-201 with an average $IC_{50}$ value of 86±33 μM (Table 3). For selectivity against STAT family members, nuclear extract preparations from EGF-stimulated mouse fibroblasts over-expressing the human epidermal growth factor receptor (NIH3T3/hEGFR) containing activated Stat1, Stat3, and Stat5 were pre-incubated with or without S3I-201 prior to incubation with the radiolabeled probes, as described in "Materials and Methods". EMSA analysis of the DNA-binding activities shows Stat3:Stat3 (upper), Stat1:Stat3 (intermediate) and Stat1:Stat1 (lower) bands of complexes with the hSIE probe (FIG. 2A-2) and Stat5:Stat5 (upper) and Stat1:Stat1 (lower) bands of complexes with the MGFe probe (FIG. 2A-2). S3I-201 preferentially inhibits Stat3 DNA-binding activity over that of Stat1, and inhibits that of Stat5 with a 2-fold less potency (FIG. 2A-2 and Table 3). The appearance of different degrees of activity of S3I-201 at 300 μM is due to the fact that different nuclear extract preparations were used, one from the v-Src transformed mouse fibroblasts (NIH3T3/v-Src) containing only activated Stat3 (FIG. 2A-1) and the other from the EGF-stimulated NIHT3T3/hEGFR that contains activated Stat1, Stat3, and Stat5 (FIG. 2A-2). Supershift analysis with anti-Stat3 antibody shows protein:hSIE complex (FIG. 2A-1) contains Stat3, while use of anti-Stat1 antibody or anti-Stat5 antibody confirms protein:MGFe complexes contain Stat1 or Stat5, respectively (FIG. 2A-2). These studies have identified S3I-201 from the NCI chemical libraries as a potential binder within the Stat3 SH2 domain and an inhibitor of Stat3 activation. S3I-201 shows 2-fold preference for Stat3 over Stat5 and greater than 3-fold preference over Stat1 (FIGS. 2A-1 and 2A-2, and Table 3).

TABLE 3

$IC_{50}$ (mM) values for the inhibition of STATs DNA-binding activity in vitro

| NSC # | Stat3:3 | Stat1:3 | Stat1:1 | Stat5:5 |
|---|---|---|---|---|
| 74859 (S3I-201) | 86 ± 33 | 160 ± 43 | >300 | 166 ± 17 |

Example 3

S3I-201 Disrupts Stat3:Stat3 Complex Formation In Vitro and in Intact Cells

Figure 1A:
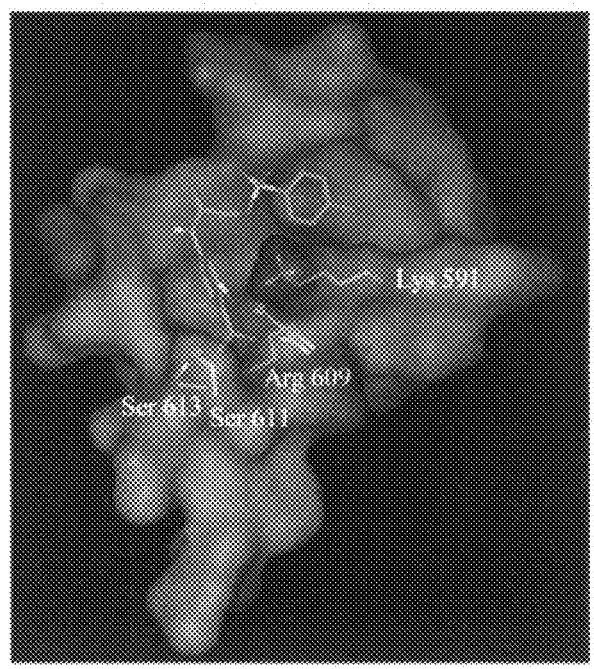
FIGS. 1A-1B show docking of S3I-201 (NSC 74859) to the SH2 domain of Stat3.
Figure 1B:
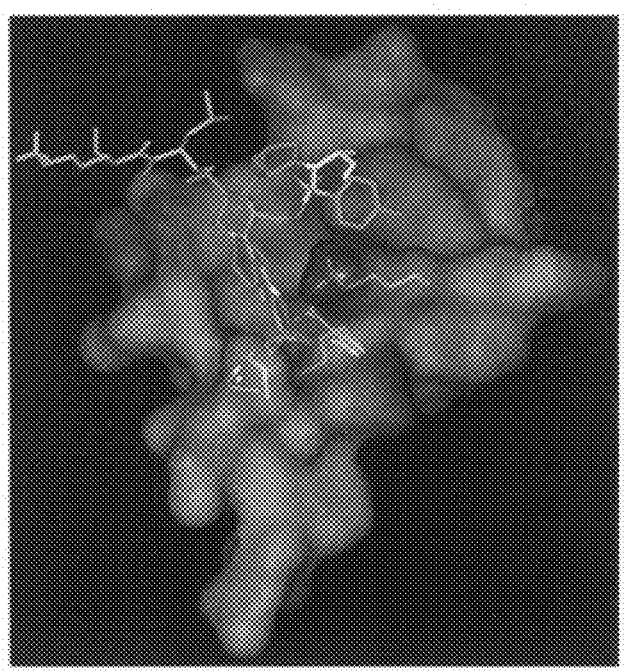

Based on the computational modeling, S3I-201 is predicted to interact with the SH2 domain of Stat3, thereby inhibiting active Stat3 DNA-binding activity (see FIGS. 1A and 1B). To provide experimental data in support of S3I-201's binding to Stat3, the present inventors investigated whether unphosphorylated, inactive Stat3 monomer could interfere with the inhibitory effect of S3I-201 on active Stat3 DNA-binding (inactive Stat3 monomer will interfere with the inhibitory activity of S3I-201 if it interacts with the compound). To make this determination, cell lysates of unphosphorylated, inactive Stat3 monomer protein prepared from Sf-9 insect cells infected with only baculovirus containing Stat3, as previously described (Turkson, J. et al. *J. Biol. Chem.*, 2001, 276:45443-45455; Turkson, J. et al. *Mol Cancer Ther*, 2004, 3:261-269; Turkson, J. et al. *Mol. Cancer. Ther.*, 2004, 3:1533-1542; Turkson, J. et al. *J Biol. Chem.*, 2005, 280:32979-32988), and cell lysates of activated Stat3 dimer protein were mixed together and the mixture was pre-incubated with S3I-201 for 30 minutes prior to incubation with the radiolabeled hSIE probe and EMSA analysis, as was previously done in FIGS. 2A-1 and 2A-2. The unphosphorylated, inactive Stat3 monomer by itself had no significant effect on DNA-binding activity of activated Stat3 (FIG. 2B-1, compare lane 2 to lane 1), as inactive Stat3 monomer is incapable of binding DNA (Turkson, J. et al. *J Biol. Chem.*, 2005, 280:32979-32988). Consistent with results in FIGS. 2A-1 and 2A-2, pre-incubation of activated Stat3 lysates with 100 µM S3I-201 completely inhibited Stat3 DNA-binding activity (FIG. 2B-1, lanes 3 and 4). By contrast, the presence of inactive Stat3 monomer diminished the inhibitory effect of S3I-201 on the activated Stat3 in a dose-dependent manner, resulting in the recovery of the active Stat3 DNA-binding activity (FIG. 2B-1, lanes 5-7). The Stat3 DNA-binding activity that was otherwise inhibited (FIG. 2B-1, lanes 3 and 4) was partially or completely restored in the presence of 4 or 5 µl of inactive Stat3 lysates, respectively (FIG. 2B-1, lanes 6 and 7). Therefore, while the inactive Stat3 monomer protein is unable to bind DNA, it is capable of interacting with S3I-201 by virtue of its SH2 domain. In turn, this interaction reduces the concentration of S3I-201 that is available to inhibit the activated Stat3. These findings support the S3I-201:Stat3 interaction, which is consistent with the predictions from the computational modeling, and suggest the interaction is independent of the activation status of Stat3. To determine whether unphosphorylated, inactive Stat1 or Stat5 monomer or the unrelated Src protein (with a SH2 domain) would have effect on S3I-201, similar studies were performed using independently prepared cell lysates from Sf-9 insect cells infected with only the baculovirus containing either Stat1, Stat5 or Src, as the present inventors have previously reported (Turkson, J. et al. *J. Biol. Chem.*, 2001, 276:45443-45455; Turkson, J. et al. *Mol Cancer Ther*, 2004, 3:261-269; Turkson, J. et al. *Mol. Cancer. Ther.*, 2004, 3:1533-1542; Turkson, J. et al. *J Biol. Chem.*, 2005, 280:32979-32988), and containing either of these proteins. In contrast to the effect observed with the inactive Stat3 monomer (FIG. 2B-1, lanes 5 to 7), EMSA analysis shows the presence of inactive Stat1, Stat5, or Src lysate induces no significant recovery of Stat3 DNA-binding activity (FIG. 2B-1, lanes 8 to 10, 11 to 13, and 14 to 16). In the case of the Stat1 monomer lysate, minimal recovery of Stat3 DNA-binding activity is observed (FIG. 2B-1, lane 10), which is evidence of a weak interaction of the Stat1 protein with S3I-201, as revealed in the initial evaluation (FIG. 2A-2). Compared to the effect of inactive Stat3 monomer lysates, the minimal to no effect of inactive Stat1 or Stat5 monomer, or the unrelated Src lysate suggests selective interaction of Stat3 with S3I-201, presumably through its SH2 domain. The amounts of proteins for each of Stat1, Stat3, or Stat5 monomer, or the Src lysate used in these studies was determined by SDS-PAGE and Western blot analysis to be nearly similar (FIG. 2B-2, lanes 17 to 20).

To further confirm the interaction of S3I-201 with Stat3 and to demonstrate that it blocks Stat3:Stat3 dimerization in intact cells, Stat3 pull-down assays involving two differently-tagged Stat3 proteins, FLAG-tagged Stat3 (FLAG-ST3) and Stat3-YFP, expressed in cells were performed. Viral Src transformed (NIH3T3/v-Src) mouse fibroblasts stably expressing Stat3-YFP were transiently-transfected with FLAG-ST3, and treated either with 0.05% DMSO (control) or with S3I-201 for 24 hours and then subjected to pull-down assay using anti-FLAG or anti-YFP antibody and SDS-PAGE. Analysis by Western blot for FLAG of whole-cell lysates shows equal expression of the FLAG-ST3 protein in the lysates in the transiently-transfected cells in both the control (DMSO-treated) and S3I-201-treated cells (FIG. 2C-2). Western blot analysis probing with anti-FLAG antibody of the Stat3-YFP immunoprecipitates shows the presence of FLAG-ST3 protein in the pulled-down lysate from control cells (FIG. 2C-1, left panel, upper lane 1), suggesting Stat3-YFP and FLAG-ST3 proteins were pulled down together as a complex. By contrast, Western blot analysis probing with anti-FLAG antibody shows no detectable level of FLAG-ST3 protein in the Stat3-YFP immunoprecipitates from S3I-201-treated cells (FIG. 2C-1, left panel, upper lane 2 vs. lane 1), suggesting the disruption by S3I-201 of the complex formation between Stat3-YFP and FLAG-ST3 proteins. The amounts of Stat3-YFP in the immunoprecipitates are shown (FIG. 2C-1, lower left panel). Similarly, Western blot analysis probing with anti-YFP antibody of the FLAG-ST3 immunoprecipitates shows Stat3-YFP present in the pulled-down lysate from the 0.05% DMSO-treated (control) cells (FIG. 2C-1, right panel, lower lane 3), but significantly reduced in the FLAG-ST3 immunoprecipitates from the S3I-201-treated cells (FIG. 2C-1, right panel, lower lane 4 vs. lane 3). These findings suggest FLAG-ST3:Stat3-YFP complex is strongly formed in the control cells, but is significantly diminished in the S3I-201-treated cells. The FLAG-ST3 protein amounts in the immunoprecipitates are shown (FIG. 2C-1, upper right panel). Together the findings indicate that S3I-201 disrupts Stat3:Stat3 dimers, suggesting that the compound interacts with the Stat3 SH2 domain in intact cells.

Example 4

S3I-201 does not Interfere with Lck-SH2 Domain-Phosphotyrosine Interaction

Figure 2D:
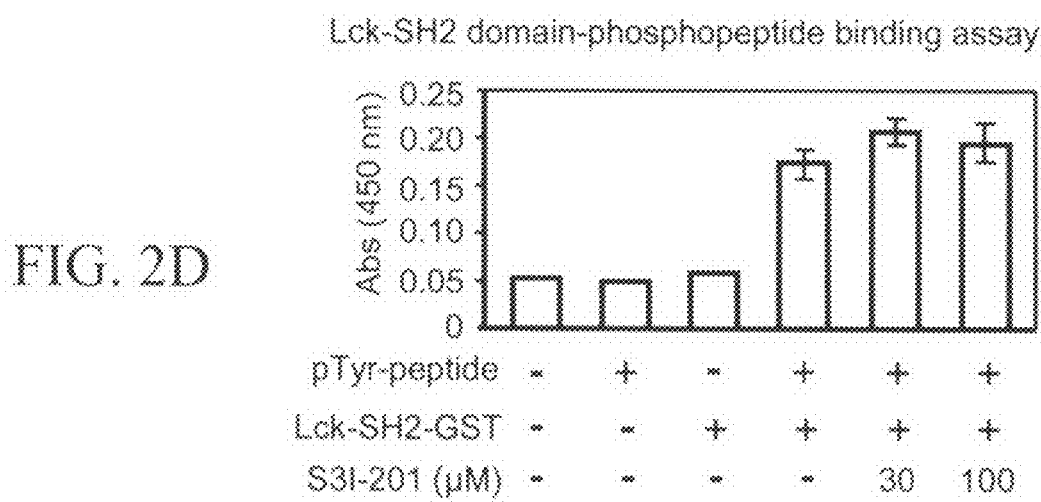

The computational modeling predicts that S3I-201 interacts with the Stat3 SH2 domain, thereby inhibiting Stat3 DNA-binding activity (FIGS. 1A and 1B). To further investigate the selectivity of S3I-201 and to rule out the possibility that it interacts with other SH2 domain-containing proteins, the present inventors evaluated its effect on the binding between the unrelated Src family protein, Lck, and the cognate phosphopeptide, EPQpYEEIEL (SEQ ID NO:2) (where pY represents pTyr of SEQ ID NO:1). The present inventors used the in vitro ELISA study involving the Lck-SH2-GST protein and the conjugate pTyr peptide, biotinyl-ε-Ac-EPQpYEEIEL-OH (SEQ ID NO:2) (Lee, T. R. and Lawrence, D. S. *J Med. Chem.*, 2000, 43:1173-1179), as described in "Materials and Methods". Results from the ELISA show that the co-presence of the Lck-SH2-GST protein and its cognate pTyr peptide results in signal induction (FIG. 2D, bar 4), suggesting an interaction between the two (Lee, T. R. and Lawrence, D. S. *J Med. Chem.*, 2000, 43:1173-1179). The addition of 30 µM and 100 µM S3I-201 has no effect on the signal induction (FIG. 2D, compare bars 5 and 6 to the bar 4), indicating that S3I-201 does not interfere with the binding of the Lck SH2 domain to its cognate pTyr peptide, EPQpYEEIEL (SEQ ID NO:2).

Example 5

S3I-201 Inhibits Stat3 Activation in Intact Cells

Figure 2E:
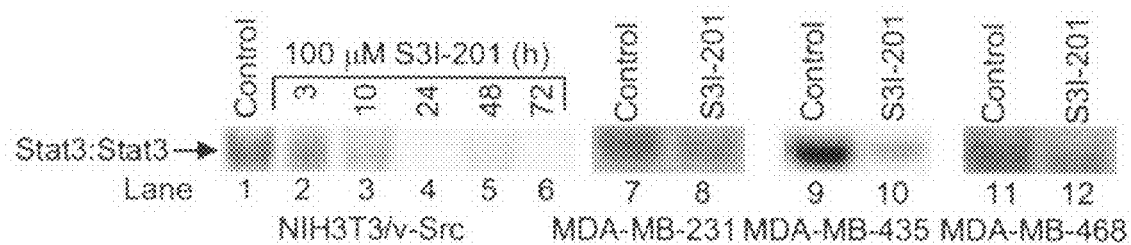
Figure 2F:
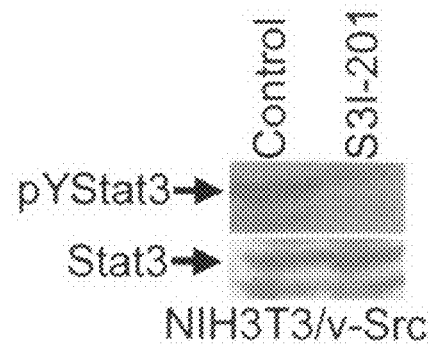

It has previously been shown that Stat3 is constitutively-activated in a variety of malignant cells (Yu, C. L. et al. *Science,* 1995, 269:81-83; Garcia, R. et al. *Oncogene,* 2001, 20:2499-2513; Turkson, J. et al. *Mol. Cell. Biol.,* 1998, 18:2545-2552). To determine the effect of S3I-201 on intracellular Stat3 activation, NIH3T3/v-Src mouse fibroblasts and human breast cancer MDA-MB-231, MDA-MB-435 and MDA-MB-468 cells that harbor constitutively-active Stat3 were treated with the compound and nuclear extracts prepared for Stat3 DNA-binding activity in vitro and EMSA analysis. Compared to control (0.05% DMSO-treated cells, lane 1), treatment with S3I-201 induced a time-dependent inhibition of constitutive Stat3 activation in NIH3T3/v-Src fibroblasts (FIG. 2E, lanes 4-6). By 24 hours, constitutive Stat3 activation was significantly inhibited in the v-Src-transformed mouse fibroblasts and in the human breast cancer MDA-MB-231, MDA-MB-435 and MDA-MB-468 cells (FIG. 2E, lanes 4-6 and 8, 10, and 12). Furthermore, SDS-PAGE and Western blot analysis of whole-cell lysates from NIH3T3/v-Src fibroblasts show pTyr705 Stat3 levels were significantly diminished following 24-hour treatment with S3I-201 (FIG. 2F), while total Stat3 protein level remained unchanged. This inhibition of tyrosine phosphorylation may be explained by the fact that by binding to the Stat3 SH2 domain, S3I-201 prevents Stat3 from binding to the pTyr motifs of the receptor tyrosine kinases (RTKs) and subsequently blocks de novo phosphorylation by tyrosine kinases. To investigate non-specific effects, SDS-PAGE and Western blot analysis was performed on whole-cell lysates from mouse fibroblasts transformed by v-Src (NIH3T3/v-Src) or overexpressing the human EGFR (NIH3T3/hEGFR) and stimulated by EGF to determine the ability to inhibit other signaling proteins. Treatment with S3I-201 for 24 hours had no significant effect on the phosphorylation of Shc (pShc), Erk1/2 (pErk1/2), or Src (pSrc) in cells (FIGS. 2G-1 and 2G-2). Total Erk1/2 protein levels were unchanged. Moreover, SDS-PAGE and Western blot analysis with the anti-pTyr antibody 4G10 clone shows no significant changes in the pTyr profile of NIH3T3/v-Src fibroblasts following 24-hour treatment with S3I-201 (FIG. 2G-4), while same treatment condition significantly diminishes pTyr705 Stat3 levels (FIG. 2F). These results together indicate that at the concentrations that inhibit Stat3 activity, S3I-201 does not significantly interfere with other signal transduction mechanisms.

Example 6

Selective Inhibition of Stat3 Transcriptional Activity by S3I-201

Figure 3A:
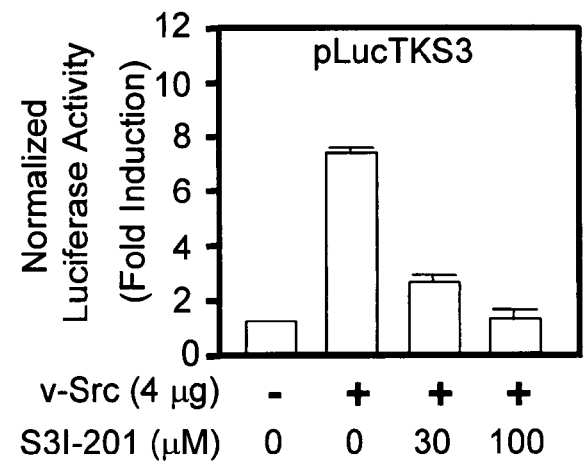
FIGS. 3A-3C show that S3I-201 suppresses Stat3-dependent but not Stat3-independent transcriptional activity. Luciferase reporter activities in cytosolic extracts prepared from normal mouse fibroblasts (NIH3T3) transiently co-transfected with the Stat3-dependent (pLucTKS3 [FIG. 3A]), or the Stat3-independent (pLucSRE [FIG. 3B] or β-Casein promoter-driven Luc [FIG. 3C]) luciferase reporters together with a plasmid expressing the v-Src oncoprotein that activates all three reporters, and untreated (0.05% DMSO, control) or treated with 100 μM S3I-201 for 24. Values are the mean and S.D. of three independent determinations.
Figure 3B:
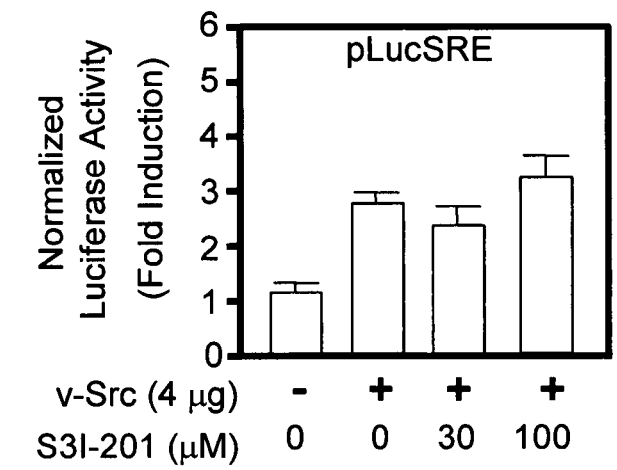
Figure 3C:
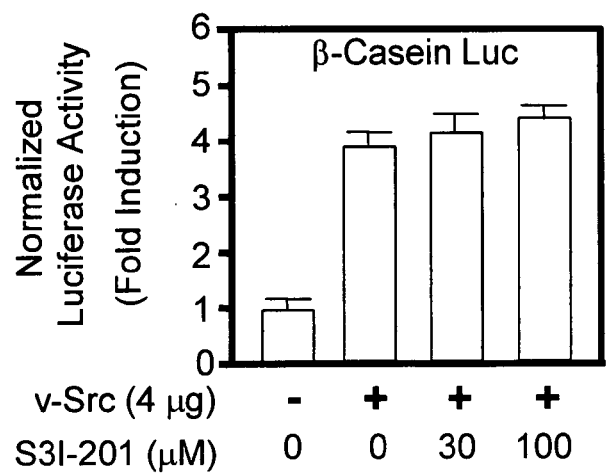

The ability of S3I-201 to inhibit Stat3:Stat3 complex formation and Stat3 DNA-binding activity prompted us to investigate its effect on Stat3-dependent transcriptional activity. Normal mouse fibroblasts (NIH3T3) were transiently co-transfected with the Stat3-dependent luciferase reporter, pLucTKS3 and a plasmid encoding the v-Src oncoprotein that activates Stat3 and cells were untreated (0.05% DMSO, control) or treated with S3I-201. As previously reported (Turkson, J. et al. *Mol. Cell. Biol.,* 1998, 18:2545-2552), v-Src protein mediated induction of the Stat3-dependent luciferase reporter, pLucTKS3 activity by about 7-fold (FIG. 3A). This Stat3-dependent pLucTKS3 induction was significantly inhibited by the treatment of cells with S3I-201 in a dose-dependent manner (FIG. 3A). To examine specificity of effects, normal mouse fibroblasts were co-transfected with the Stat3-independent luciferase reporters, pLucSRE (Turkson, J. et al. *Mol. Cell. Biol.,* 1998, 18:2545-2552) or β-Casein promoter-driven Luc (Galbaugh, T. et al. *BMC Cell Biol.,* 2006, 7:34) together with v-Src plasmid and treated with S3I-201 or without (0.05% DMSO). In contrast to the effect on the induction of pLucTKS3 luciferase reporter, v-Src-mediated induction of Stat3-independent pLucSRE (Turkson, J. et al. *Mol. Cell. Biol.,* 1998, 18:2545-2552) or the β-Casein promoter Luc (Galbaugh, T. et al. *BMC Cell Biol.,* 2006, 7:34) was not affected by treatment with S3I-201 (FIGS. 3B and 3C). These results demonstrate that S3I-201 selectively inhibits Stat3-dependent transcriptional activity, with no effect on Stat3-independent transcriptional events.

Example 7

S3I-201 Blocks Anchorage-Dependent and Independent Growth Only in Cells where Stat3 is Persistently Activated The above results of FIGS. 2 and 3 demonstrate that S3I-201 disrupts Stat3 activation. The present inventors next determined whether this Stat3 activity inhibitor is able to inhibit the anchorage-dependent and -independent (transformation) growth of human and mouse cancer cell lines and whether this inhibition is dependent on the presence of persistently-active Stat3. The human breast carcinoma (MDA-MB-231, MDA-MB-435 and MDA-MB-468) cell lines and the v-Src-transformed mouse fibroblasts (NIH3T3/v-Src) that harbor constitutively-active Stat3, and the human breast carcinoma MDA-MB-453 cell line and normal mouse fibroblasts (NIH3T3) that do not harbor aberrant Stat3 activity were treated with S3I-201 and analyzed for viable cell number by trypan blue exclusion and microscopy (FIG. 4A-4F) or MTT assay (data not shown). Treatment with S3I-201 significantly reduced viable cell numbers and inhibited growth of transformed mouse fibroblasts NIH3T3/v-Src and breast carcinoma cell lines (MDA-MB-231, MDA-MB-435 and MDA-MB-468) (FIGS. 4E, 4D, and 4F, respectively). By contrast, growth and viability of normal mouse fibroblasts (NIH3T3) and breast carcinoma cell line (MDA-MB-453) without aberrant Stat3 activity were not significantly altered (FIGS. 4A and 4B). Thus, S3I-201 affected only those cell lines harboring aberrant Stat3, consistent with inhibition of Stat3 DNA-binding activity (Table 3 and FIG. 2).

Figure 4G:
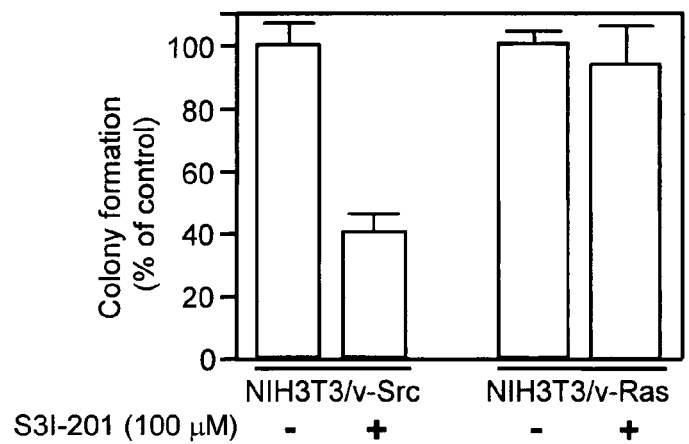

To further examine the effects of S3I-201 on Stat3 biological functions, the compound was tested for its ability to inhibit the growth of v-Src transformed mouse fibroblasts (NIH3T3/v-Src) in soft-agar suspension in colony formation assays. Results show that growth of v-Src transformed mouse fibroblasts in soft-agar suspension is significantly inhibited by S3I-201 (FIG. 4G). By contrast, soft-agar growth of v-Ras transformed counterpart (NIH3T3/v-Ras) that is independent of constitutively-active Stat3 is unaffected by treatment with S3I-201 (FIG. 4G), indicating that S3I-201 selectively inhibits Stat3-mediated malignant transformation.

Example 8

S3I-201 Preferentially Induces Apoptosis of Malignant Cells Harboring Constitutively-Active Stat3

Figure 5A:
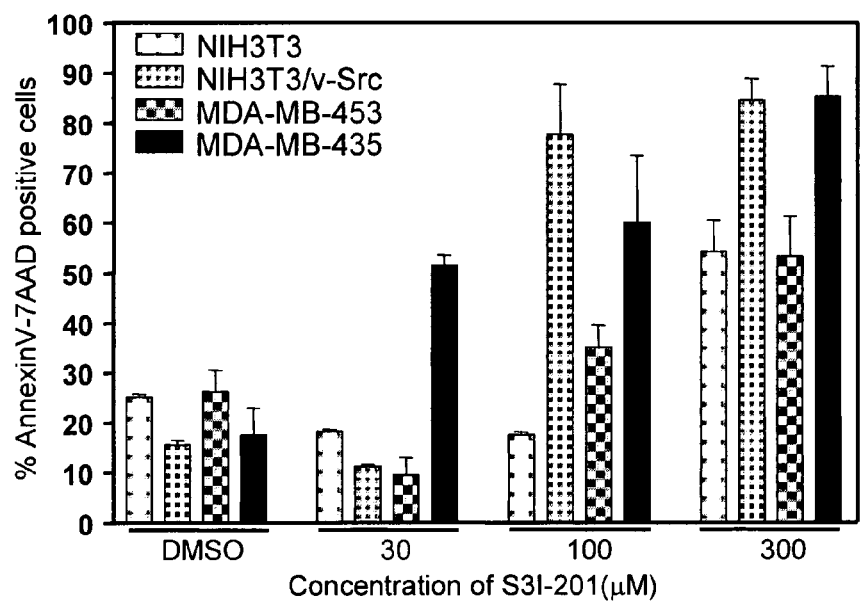
FIGS. 5A-5C show that S3I-201 inhibits Cyclin D1, Bcl-xL and Survivin expression and induces apoptosis in a Stat3-dependent manner.

The present inventors next determined if the S3I-201 induced loss of tumor cell viability is due to apoptosis. To this end, the human breast carcinoma cell lines, MDA-MB-453 and MDA-MB-435, and the normal mouse fibroblasts (NIH3T3) and their v-Src transformed counterpart (NIH3T3/v-Src) were untreated (0.05% DMSO, control) or treated with S3I-201 for 48 hours and analyzed by Annexin V binding and Flow Cytometry. At 30-100 µM, S3I-201 induced significant apoptosis in the representative human breast carcinoma cell line, MDA-MB-435 and the NIH3T3/v-Src, all of which harbor constitutively-active Stat3 (FIG. 5A). The breast carcinoma MDA-MB-435 cell line is more sensitive to 30 µM S3I-201 (FIG. 5A). By contrast, the human breast cancer MDA-MB-453 cells and the normal mouse fibroblasts (NIH3T3) that do not contain abnormal Stat3 activity are less sensitive to S3I-201 at 100 µM or less (FIG. 5A). These findings indicate that at concentrations that inhibit Stat3 activity, S3I-201 selectively induces apoptosis of transformed cells harboring aberrant Stat3 signaling, suggesting the inhibition of constitutively-active Stat3 is part of the underlying mechanism of apoptosis by S3I-210. At 300 µM or higher, S3I-201 induced general, non-specific cytotoxicity independent of Stat3 activation status.

Figure 5B:
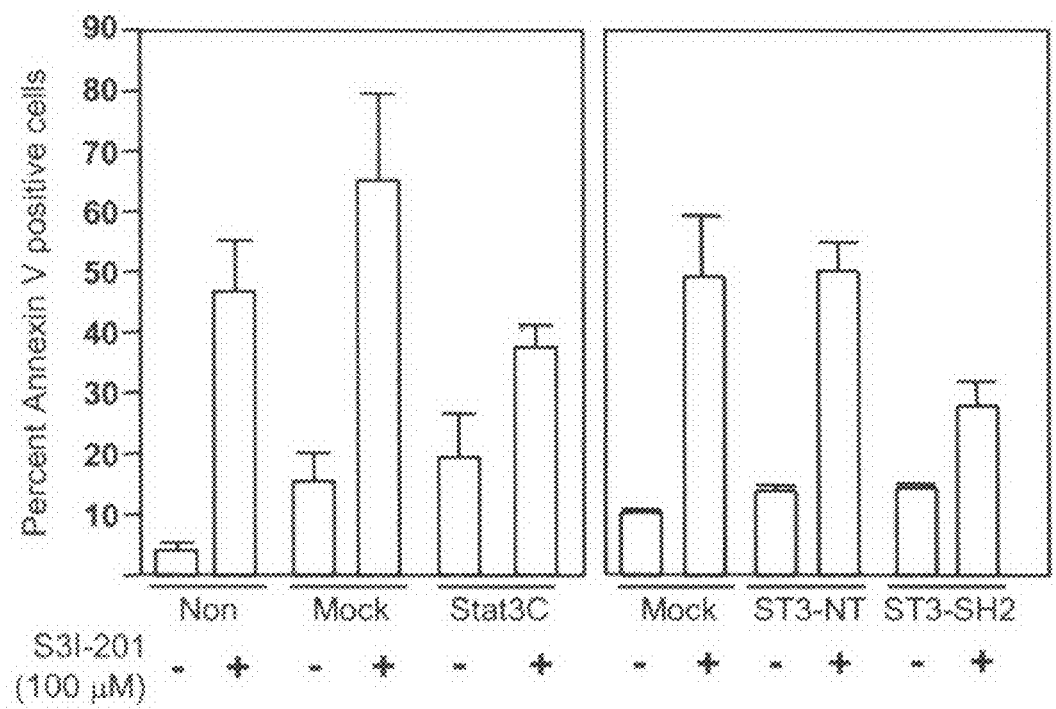

The present inventors reasoned that if the ability of S3I-201 to induce tumor cell apoptosis is due to its ability to inhibit Stat3 activation, then the constitutively-dimerized and persistently-activated Stat3C (Bromberg, J. F. et al. *Cell*, 1999, 98:295-303) should rescue from S3I-201-induced apoptosis. To this end, the breast carcinoma MDA-MB-231 cells that harbor activated Stat3 were transiently transfected with Stat3C and evaluated for apoptosis. Twenty-four hours after transfection, cells were treated or untreated with S3I-201 for an additional 24-48 hours, harvested and analyzed by Annexin V binding and Flow Cytometry. Consistent with results in FIG. 5A, S3I-201 induced 50-80% apoptosis in untransfected or mock-transfected human breast carcinoma MDA-MB-231 cells (FIG. 5B, left panel). By contrast, cells transfected with Stat3C and treated with S3I-201 showed greatly diminished apoptosis (FIG. 5B, left panel)—less than 2-fold compared with 9- or 5-fold apoptosis in non-transfected or mock-transfected cells, respectively. There is increased in the background level of cell death, which could be due to the effects of transfection. The rescue from the apoptotic effects of S3I-201 can be explained on the basis that the artificially-designed activated Stat3C is not inhibited by S3I-201 and is sufficient to promote the biological effects of the endogenous Stat3. Thus the activated Stat3C rescues cells from the apoptotic effects of S3I-201 by compensating for the loss of endogenous Stat3 activity due to inhibition by S3I-201.

To establish that the effect of S3I-201 is due to its interaction with the Stat3 SH2 domain, similar studies were performed in cells which were transiently-transfected with either an expression vector for the N-terminal region of Stat3 (ST3-NT) or the Stat3 SH2 domain (ST3-SH2) and treated with or without S3I-201. Annexin V binding and Flow Cytometry showed that while mock-transfected cells were strongly induced by S3I-201 to undergo apoptosis (FIG. 5B, left panel), similar to the Stat3C-transfected cells, the overexpression of the Stat3-SH2 domain diminished the apoptotic effects of S3I-201 (FIG. 5B, left panel). In contrast, cells overexpressing the ST3-NT region showed strong induction of apoptosis (FIG. 5B, left panel), suggesting ST3-NT has no effect on the ability of S3I-201 to induce apoptosis of malignant cells. The present inventors infer that the exogenous ST3-SH2 domain binds to S3I-201, thereby preventing the compound from binding to and inhibiting endogenous constitutively-active Stat3 protein and its biological functions.

Example 9

Figure 5C:
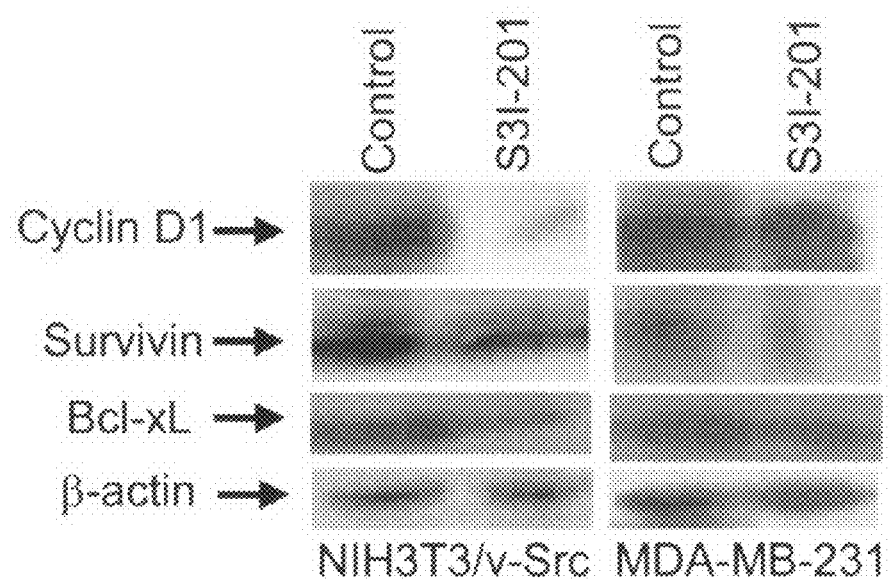

S3I-201 Represses the Expression of the Stat3 Regulated Genes Cyclin D1, Bcl-xL, and Survivin To investigate the molecular mechanisms for the cell growth inhibition and apoptosis by S3I-201, the present inventors examined the expression of the known Stat3 target genes in the v-Src-transformed mouse fibroblasts (NIH3T3/v-Src) and the human breast carcinoma MDA-MB-231 cell line that harbor constitutively-active Stat3. Immunoblot analysis of whole-cell lysates shows significant reduction in expression of the Cyclin D1, Bcl-xL and Survivin proteins in response to S3I-201 treatment (FIG. 5C), indicating that S3I-201 represses induction of the cell cycle and anti-apoptotic regulatory genes in malignant cells. These findings are consistent with the biological effects induced by S3I-201 (FIGS. 3-5), and correlate with the inhibition of aberrant Stat3 activity.

Example 10

S3I-201 Induces Regression of Human Breast Tumor Xenografts

Figure 6A:
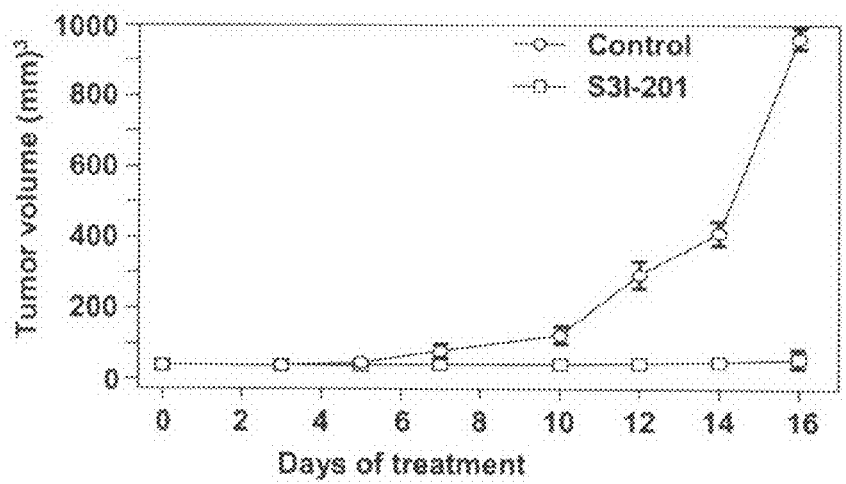
FIGS. 6A-6C show tumor growth inhibition by S3I-201.
Figure 6B:
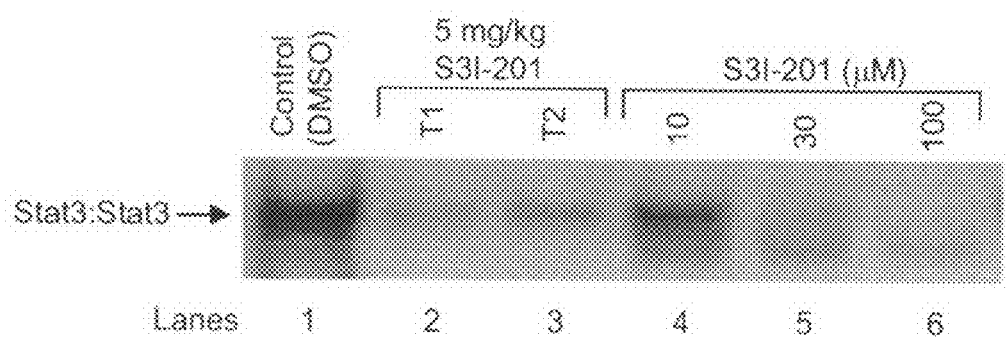
Figure 6C:
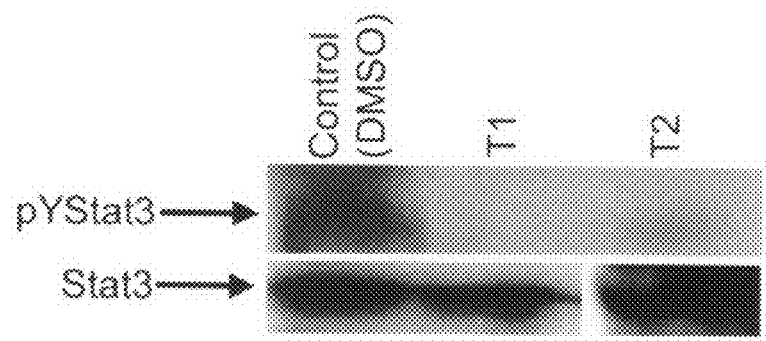

The aforementioned findings demonstrate that S3I-201 possesses a strong inhibitory activity against aberrant Stat3, potently inhibits anchorage-dependent and -independent tumor cell growth, and induces apoptosis of malignant cells in a Stat3-dependent manner. The present inventors extended these studies to evaluate the antitumor efficacy of S3I-201 using mouse models of human breast tumor xenografts that harbor constitutively-active Stat3. Human breast (MDA-MB-231) tumor-bearing mice were given i.v. injection of S3I-201 or vehicle every 2 or every 3 days for two weeks, and tumor measurements were taken every 2 to 3 days. Compared to control (vehicle-treated) tumors, which continued to grow, strong growth inhibition of human breast tumors were observed in mice that received S3I-201 (FIG. 6A). Continued evaluation of treated mice upon termination of treatment showed no resumption of tumor growth (data not shown), suggesting potentially a long-lasting effect of S3I-201 on tumor growth. To determine that target was inhibited by S3I-201, lysates were prepared from tumor tissue from one control animal and from the residual tumor tissue in two treated-mice for Stat3 DNA-binding activity in vitro, as the present inventors have previously done (Turkson, J. et al. *Mol. Cancer. Ther.*, 2004, 3:1533-1542). EMSA analysis showed strong inhibition of Stat3 DNA binding activity in residual tumor tissue from mice treated with S3I-201 (T1 and T2) compared to control tumor (FIG. 6B, lanes 1 to 3). SDS-PAGE and Western blot analysis of the lysates revealed minimal to no detection of pTyr Stat3 (pYStat3) in residual tumor tissue from treated mice (T1 and T2) compared to control (FIG. 6C, upper panel). Total Stat3 protein remained unchanged (FIG. 6C, lower panel). Moreover, EMSA analysis of in vitro Stat3 DNA-binding activity also shows that pre-incubation of lysates of equal total protein from control tumor tissue with 10, 30, and 100 µM S3I-201 prior to incubation with radiolabeled hSIE probe resulted in a dose-dependent abrogation of Stat3 activity (FIG. 6B, lanes 4 to 6), as observed originally in FIG. 2A-1. Together, these studies establish the proof-of-concept for the antitumor effect of S3I-201 in tumors that harbor constitutively-active Stat3.

The data in the Examples demonstrate the feasibility of using X-ray crystallographic data and computational modeling as a basis for a structure-based virtual screening to identify chemical probes and small-molecule binders of the Stat3 SH2 domain. The docking approach with GLIDE 2.7 (Friesner, R. et al. *J. Med. Chem.*, 2004, 47:1739-1749; Halgren, T. et al. *J. Med. Chem.*, 2004, 47:1750-1759) was first validated using the native pTyr peptide, APY*LKT, which produced a docking mode that closely resembled the X-ray crystal structure (Becker, S. et al. *Nature*, 1998, 394:145-151). By this approach, the present inventors have docked and scored small-molecules from the NCI Chemical libraries into the Stat3 SH2 domain, and identified potent binders that ranked within the top ~0.1% of the docked and scored Plated Set 3D structures. S3I-201 (NSC 74859) emerged as a potent inhibitor of Stat3 DNA-binding activity in vitro. Similar computational analysis has been applied in the development of inhibitors of Stat3 and other proteins (Shao, H. et al. *J Biol. Chem.*, 2004, 279:18967-18973; Song, H. et al. *Proc Natl Acad Sci USA*, 2005, 102:4700-4705). The docking pose of S3I-201 suggests that its aminosalicylic moiety mimics the phenylphosphate group of the PY*LKT motif. Furthermore, its carboxyl group is hydrogen bonded to the Arg 609, Ser 611 and Ser 613 of Stat3, while the phenolic hydroxyl group is hydrogen-bonded to Lys 591. Moreover, the proximity of the Lys 591 to the benzene ring that contains the phenolic hydroxyl group suggests the possibility of a stabilizing pication interaction. Also, the tolyl group is buried within a partially hydrophobic pocket, which contains the tetramethylene portion of the side chain of Lys 592 and the trimethylene portion of the side chain of Arg 595, along with residues Ile 597 and Ile 634. The present inventors believe that these features (the phosphate mimic and hydrophobic side chain) combine and explain how S3I-201 binds to the SH2 domain of Stat3.

The native pTyr peptide inhibitor of Stat3, APY*LKT (SEQ ID NO:1), was previously shown to disrupt Stat3:Stat3 dimerization, thereby inducing antitumor cell effects (Turkson, J. et al. *Mol Cancer Ther*, 2004, 3:261-269). The computational analysis predicts that S3I-201 is a reasonably strong binder within the Stat3 SH2 domain, raising the possibility that it might disrupt Stat3:Stat3 dimerization as a mode of inhibition of Stat3. Using differently-tagged Stat3 monomer proteins in pull-down assays, the present inventors demonstrate that S3I-201 disrupts the complex formation between two Stat3 monomers. S3I-201 preferentially interacts with Stat3 monomer protein over Stat1 or the Src family protein, and has a 2-fold lower potency for Stat5. In cells, the interactions with Stat3 will prevent binding of the Stat3 SH2 to RTKs and Src and/or Jaks and inhibit de novo phosphorylation and activation of Stat3 monomer. Thus, S3I-201 mediates selective inhibition of Stat3 transcriptional activity, induces cell growth inhibition, loss of viability, and apoptosis of human breast cancer and v-Src-transformed mouse cells that harbor constitutively-active Stat3, as well as blocks v-Src transformation, events which are all consistent with the abrogation of Stat3 activation (Turkson, J. et al. *J. Biol. Chem.*, 2001, 276:45443-45455; Turkson, J. et al. *Mol Cancer Ther*, 2004, 3:261-269; Garcia, R. et al. *Oncogene*, 2001, 20:2499-2513; Catlett-Falcone, R. et al. *Immunity*, 1999, 10:105-115; Mora, L. B. et al. *Cancer Res*, 2002, 62:6659-6666). The observation that overexpressed exogenous Stat3 SH2 domain, but not Stat3 N-terminus in malignant cells protects against S3I-201-induced apoptosis strongly supports the Stat3 SH2 domain as the target of S3I-201, and for that reason will bind to S3I-201 in cells, thereby preventing the S3I-201 from inhibiting endogenous Stat3 activity. Moreover, the rescue from the apoptotic effects of S3I-201 by the ectopic expression of the constitutively-active Stat3C in malignant cells demonstrates that Stat3C compensates for the absence of aberrant Stat3 signaling. Thus, these findings further strongly suggest the anti-tumor cell effects of S3I-201 are mediated by suppressing aberrant Stat3-induced dysregulation of the cell cycle control and the anti-apoptotic genes. Furthermore, in vivo antitumor effects of S3I-201 in human breast tumor xenografts establish the proof-of-concept for the therapeutic potential of S3I-201 as a Stat3 inhibitor in human tumors that harbor constitutively-active Stat3.

Described herein is the first report of a Stat3 SH2 domain binder and an inhibitor of Stat3 signaling, which is structurally different from previously identified dimerization disruptors, peptides and peptidomimetics (Turkson, J. et al. *J. Biol. Chem.*, 2001, 276:45443-45455; Turkson, J. et al. *Mol Cancer Ther*, 2004, 3:261-269), or other Stat3 inhibitors, such as the g-quartet oligonucleotides (Jing, N. et al. *DNA Cell Biol*, 2003, 22:685-696), peptide aptamers (Nagel-Wolfrum, K. et al. *Mol Cancer Res*, 2004, 2:170-182), platinum (IV) complexes (Turkson, J. et al. *Mol. Cancer. Ther.*, 2004, 3:1533-1542; Turkson, J. et al. *J Biol. Chem.*, 2005, 280:32979-32988), cucurbitacin (Blaskovich, M. A. et al. *Cancer Res*, 2003, 63:1270-1279), and STA-21 (NSC 628869) (Song, H. et al. *Proc Natl Acad Sci USA*, 2005, 102:4700-4705). While SH2 domains have been noted to have a high sequence similarity in their 100 amino acids (Sheinerman, F. B. et al. *J Mol. Biol.*, 2003, 334:823-841; Kuriyan, J. and Cowburn, D. *Annu Rev Biophys Biomol Struct.*, 1997, 26:259-288), S3I-201 has preference for Stat3 in that at concentrations that inhibit Stat3, S3I-201 has low effect on Stat1 and Stat5, no interaction with the Src family proteins, weak inhibition of Erks 1/2 and Shc activation, and low toxicity to cells with no aberrant Stat3.

The study described herein supports computational modeling application in structure-based virtual screening for identifying Stat3 inhibitors from chemical libraries, and together with another report (Song, H. et al. *Proc Natl Acad Sci USA*, 2005, 102:4700-4705) is among the first to identify Stat3 inhibitors by this approach. S3I-201 represents a new lead for developing combinatorial libraries with increased diversity, thereby setting a new course in the Stat3 inhibitor design.

Example 11

Compound Synthesis

The following compounds were prepared according to Scheme 1.

Scheme 1

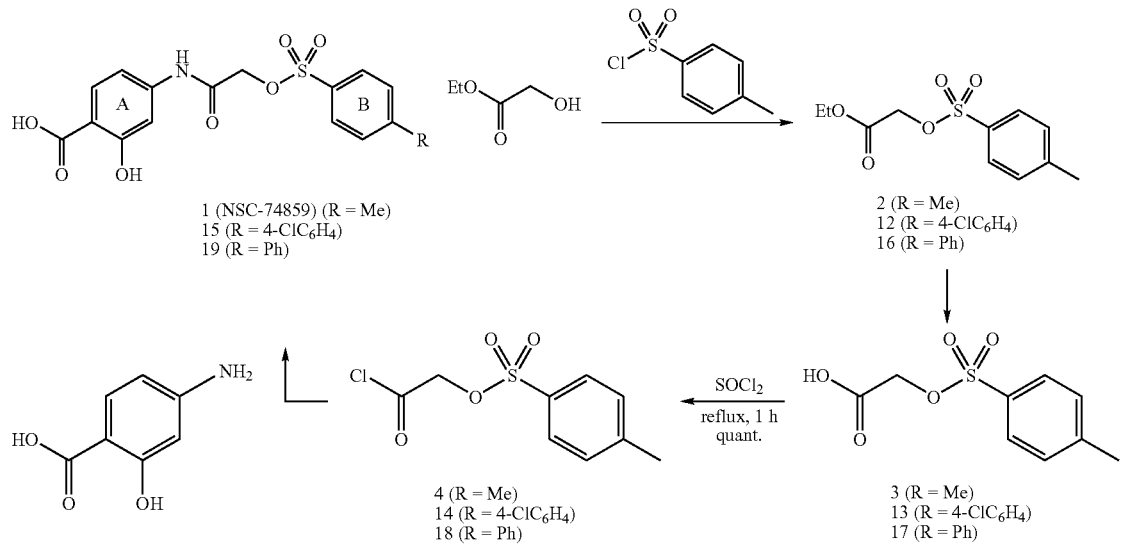

1 (NSC-74859) (R = Me)
15 (R = 4-ClC₆H₄)
19 (R = Ph)

2 (R = Me)
12 (R = 4-ClC₆H₄)
16 (R = Ph)

4 (R = Me)
14 (R = 4-ClC₆H₄)
18 (R = Ph)

3 (R = Me)
13 (R = 4-ClC₆H₄)
17 (R = Ph)

SOCl₂
reflux, 1 h
quant.

Ethyl 2-(tosyloxy)acetate (2). A solution of ethyl glycolate (500 mg, 4.8 mmol) and tosyl chloride (915 mg, 4.8 mmol) in anhydrous diethyl ether (2 ml) at 0° C. was treated dropwise with triethylamine (1.34 ml, 9.6 mmol). The temperature was maintained at 0° C. with stirring for a further 2 h. After this time, water was added and the phases separated. The aqueous phase was extracted with fresh diethyl ether. The combined organic extracts were dried (MgSO₄), filtered and the solvent removed in vacuo. The crude product was purified by column chromatography over silica gel ($R_f$=0.29, 25% ethyl acetate in hexane) affording the tosylate 2 as a colorless oil which solidified on standing as a white solid (868 mg, 70%). [This procedure was repeated on 2× scale (1.8 g, 73%)]. $\delta_H$ (400 MHz, CDCl₃) 1.22-1.27 (3H, m, CH₃), 2.46 (3H, s, ArCH₃), 4.16-4.22 (2H, m, CH₂CH₃), 4.58-4.59 (2H, m, OCH₂), 7.36 (2H, d, J=8.2 Hz, ArH), 7.84 (2H, d, J=8.2 Hz, ArH); $\delta_c$ (100.6 MHz, CDCl₃) 14.2, 21.9, 62.1, 64.9, 128.3, 130.1, 132.9, 145.5, 166.2; MS (ES⁺) 276.0 (100%, [M+H₂O]⁺) (ion not detected in ES⁻).

2-(Tosyloxy)acetic acid (3). A solution of ethyl 2-(tosyloxy)acetate (2, 860 mg, 3.33 mmol) in ethanol (4 ml) was treated at room temperature with 5% NaOH aqueous solution (2 ml). The resulting mixture was stirred at room temperature for 3 h. The ethanol was removed in vacuo and aqueous 5% HCl solution (2.7 ml) was added. The aqueous mixture was extracted with chloroform and the organic extracts dried (Na₂SO₄), filtered and the solvent removed under reduced pressure. The remaining white solid was recrystallized from hexane/ethyl acetate as a white powder (476 mg, 62%). [This reaction was repeated on 2× scale (1.449 g, 94%)]. $\delta_H$ (400 MHz, MeOD) 2.45 (3H, s, Me), 4.58 (2H, s, CH₂), 7.44 (2H, d, J=8.2 Hz, ArH), 7.82 (2H, d, J=8.2 Hz, ArH); $\delta_c$ (100.6 MHz, MeOD) 20.4, 64.7, 128.0, 129.9, 133.0, 145.6, 168.2; MS (ES⁺) 247.8 (100%, [M+H₂O]⁺); MS (ES⁻) 170.1 (100%, TsO⁻).

2-Chloro-2-oxoethyl-4-methylbenzenesulfonate (4). A mixture of 2-(tosyloxy)acetic acid (3, 400 mg, 1.74 mmol) and thionyl chloride (1 ml) was heated at reflux for 1.5 h. The excess thionyl chloride was removed in vacuo and the resulting white solid dried under high vacuum at 50° C. for 1.5 h. The product acid chloride was used without further purification.

2-Hydroxy-4-(2-(tosyloxy)acetamido)benzoic acid 1 (NSC-59263). A mixture of p-amino salicylic acid (102 mg, 0.67 mmol) and NaOH (27 mg, 0.67 mmol) in water (6 ml) was stirred at room temperature for 10 min until all of the solid material had dissolved. Na₂CO₃ (59 mg, 0.5561 mmol) was then added and the mixture cooled to 0° C. A solution of 2-chloro-2-oxoethyl-4-methylbenzenesulfonate (4, 200 mg, 0.8044 mmol) in THF (2 ml) was injected rapidly and the resulting solution allowed to warm to room temperature and stirred for 2 h. Then reaction mixture was poured into a separating funnel containing diethyl ether. The phases were separated and the aqueous phase washed with a further portion of diethyl ether. The aqueous phase was acidified to pH 1 by addition of 1N HCl solution and the product extracted into ethyl acetate. The ethyl acetate was washed twice with 1N HCl solution and the organic phase was dried (Na₂SO₄), filtered and the solvent removed in vacuo. The resulting pale yellow solid was triturated with chloroform leaving 1 as a white powder (155 mg, 63%). $\delta_H$ (400 MHz, DMSO) 2.37 (3H, s, Me), 4.68 (2H, s, CH₂), 6.93 (1H, d, J=7.4 Hz, ArH), 7.17 (1H, s, ArH), 7.46 (2H, d, J=6.8 Hz, ArH), 7.69 (1H, d, J=7.4 Hz, ArH), 7.81 (2H, d, J=6.8 Hz, ArH), 10.32 (1H, s, NH); $\delta_c$ (100.6 MHz, DMSO) 21.8, 68.0, 107.0, 110.7, 128.5, 130.9, 131.7, 132.7, 144.5, 146.0, 162.8, 164.5, 172.2; MS (ES⁺) 366.0 (100%, [M+H]⁺), 388.0 (50%, [M+Na]⁺); (ion not detected in ES⁻).

4-(2-(Tosyloxy)acetamido)benzoic acid (5). A mixture of p-aminobenzoic acid (92 mg, 0.67 mmol) and NaOH (27 mg, 0.67 mmol) in water (6 ml) was stirred at room temperature for 10 min until all of the solid material had dissolved. Na₂CO₃ (59 mg, 0.5561 mmol) was then added and the mixture cooled to 0° C. A solution of 2-chloro-2-oxoethyl-4-methylbenzenesulfonate (4, 200 mg, 0.8044 mmol) in THF (2 ml) was injected rapidly and the resulting solution allowed to warm to room temperature and stirred for 2 h. Then reaction mixture was poured into a separating funnel containing diethyl ether. The phases were separated and the aqueous phase washed with a further portion of diethyl ether. The aqueous phase was acidified to pH 1 by addition of 1N HCl solution and the product extracted into ethyl acetate. The ethyl acetate was washed twice with 1N HCl solution and the organic phase was dried (Na₂SO₄), filtered and the solvent removed in vacuo. The resulting pale orange solid was recrystallized from chloroform/MeOH (20:1) affording 5 as a white powder (146 mg, 62%). $\delta_H$ (400 MHz, DMSO) 2.37 (3H, s, Me), 4.70 (2H, s, CH₂), 7.46 (2H, d, J=8 Hz, ArH), 7.59 (2H, d, J=8.6 Hz, ArH), 7.82 (2H, d, J=8 Hz, ArH), 7.87 (2H, d, J=8.6 Hz, ArH), 10.39 (1H, s, NH), 12.72 (1H, CO₂H); $\delta_c$ (100.6 MHz, DMSO) 21.8, 68.0, 119.4, 126.4, 128.5, 130.9, 131.1, 132.7, 142.7, 146.0, 164.4, 167.5; MS (ES⁺) 349.7 (100%, [M+H]⁺), 371.7 (40%, [M+Na]⁺); MS (ES⁻) 347.9 (100%, [M−H]⁻); HRMS [M−H]⁻ requires 348.05473, found 348.05334.

Compounds 6, 7, and 8

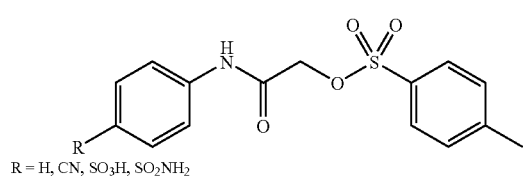

R = H, CN, SO₃H, SO₂NH₂

General Procedure: A suspension of the aniline derivative (0.455 mmol) in water (6 ml) was stirred at room temperature for 10 min. Na₂CO₃ (40 mg, 0.455 mmol) was then added and the mixture cooled to 0° C. A solution of 2-chloro-2-oxoethyl-4-methylbenzenesulfonate (4, 125 mg, 0.5 mmol) in THF (2 ml) was injected rapidly and the resulting solution allowed to warm to room temperature and stirred for 2 h.

2-Oxo-2-(phenylamino)ethyl 4-methylbenzenesulfonate (6): A white precipitate formed in the reaction mixture. This precipitate was collected by filtration, washed with water and dried under high vacuum. This afforded 6 as an off white powder (103 mg, 74%). An analytical sample was obtained by recrystallization from hexane/ethyl acetate (white needles). $\delta_H$ (400 MHz, MeOD) 2.40 (3H, s, CH₃), 4.63 (2H, s, CH₂), 7.10 (1H, t, J=7.6 Hz, ArH), 7.28 (2H, t, J=7.6 Hz, ArH), 7.41-7.50 (4H, m, ArH), 7.85 (2H, d, J=8 Hz); $\delta_c$ (100.6 MHz, MeOD) 20.4, 67.2, 120.5, 124.7, 128.1, 128.6, 130.0, 132.6, 137.5, 145.9, 164.6; MS (ES⁺) 306.0 (100%, [M+H]⁺); HRMS [M+H]⁺ requires 306.07946, found 306.07944.

2-(4-Cyanophenylamino)-2-oxoethyl 4-methylbenzenesulfonate (7): A orange precipitate formed in the reaction mixture. This precipitate was collected by filtration, washed with water and dried under high vacuum. The solid was shown by NMR analysis to comprise of the desired product and starting material. The solid was purified by column chromatography ($R_f$=0.39, 50% ethyl acetate in hexane) affording 7 as an off white powder (58 mg, 39%). $\delta_H$ (400 MHz, MeOD/DMSO spike) 2.41 (3H, s, CH₃), 4.68 (2H, s, CH₂), 7.44 (2H, d, J=8 Hz, ArH), 7.66-7.71 (4H, m, ArH), 7.86 (2H, d, J=8 Hz, ArH); $\delta_c$ (1000.6 MHz, MeOD/DMSO spike) 20.5, 67.3, 107.1, 118.6, 120.1, 128.2, 130.1, 133.1, 142.2, 146.0, 165.0; MS (ES⁺) 330.7 (55%, [M+H]⁺), 347.7 (100%, [M+H₂O]⁺).

2-Oxo-2-(4-sulfamoylphenylamino)ethyl 4-methylbenzenesulfonate (8): A white precipitate formed in the reaction mixture. This precipitate was collected by filtration, washed with water and dried under high vacuum. This afforded 8 as an off white powder (109 mg, 62%). An analytical sample was obtained by recrystallization from acetone/ethyl acetate (colourless/white crystals). $\delta_H$ (400 MHz, MeOD/DMSO spike) 2.42 (3H, s, CH₃), 4.68 (2H, s, CH₂), 7.44 (2H, d, J=8 Hz, ArH), 7.67 (2H, d, J=8.4 Hz, ArH), 7.83 (2H, d, J=8.4 Hz, ArH), 7.87 (2H, d, J=8 Hz, ArH); $\delta_c$ (100.6 MHz, MeOD/DMSO spike) 20.5, 67.3, 119.8, 127.0, 128.2, 130.1, 132.7, 139.3, 141.2, 146.0, 164.9; MS (ES⁺) 348.0 (100%), 385.0 (20%, [M+H]⁺), 402.0 (50%, [M+H₂O]⁺).

The following compounds were prepared according to Scheme 2.

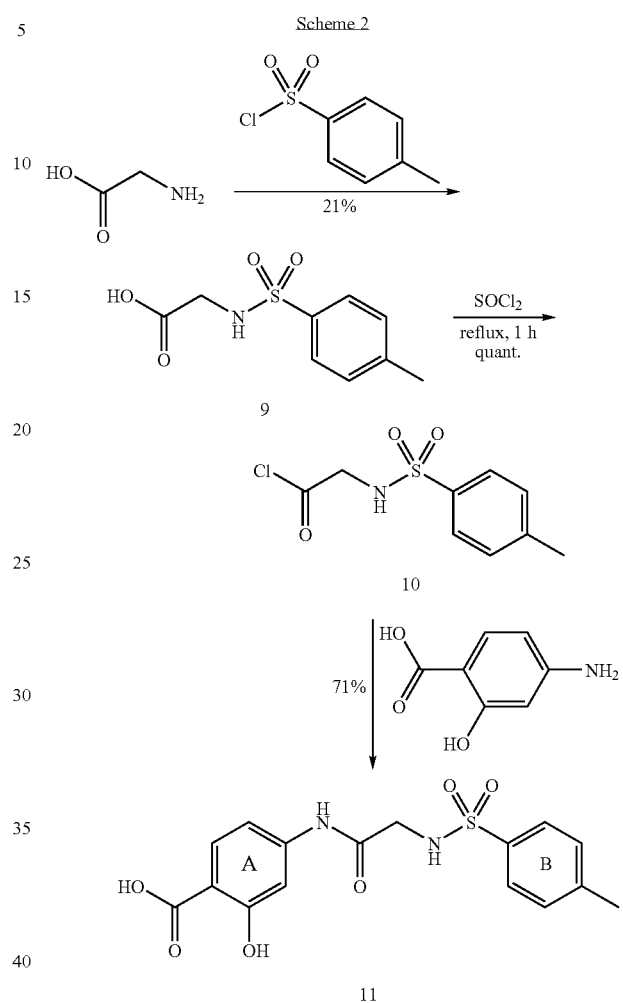

2-(4-Methylphenylsulfonamido)acetic acid (9). Glycine (1 g, 13.32 mmol) was dissolved in 1N NaOH (aq.) and a solution of tosyl chloride (2.62 g, 13.72 mmol) in diethyl ether (15 ml) was added portion wise with stirring over 10 min. The resulting mixture was allowed to stir at room temperature for 3 h. The ethereal layer was separated and the aqueous layer treated with 2N HCl solution until acidified to pH 5. After cooling the resulting solution to 0° C., the product began to precipitate from the solution. The solid was collected by filtration and the mother liquor placed in a fridge overnight causing more of the desired product to precipitate. The solid was again collected by filtration and the combined collected solid was dried under high vacuum affording 9 as a white powder (613 mg, 21%). $\delta_H$ (400 MHz, MeOD) 2.41 (3H, s, CH₃), 3.66 (2H, s, CH₂), 7.35 (2H, d, J=8 Hz, ArH), 7.73 (2H, d, J=8 Hz, ArH); $\delta_c$ (100.6 MHz, MeOD) 20.3, 43.6, 127.0, 129.5, 137.6, 143.6, 171.0; MS (ES⁺) 246.8 (100%, [M+H₂O]⁺); MS (ES⁻) 227.9 (100%, [M−H]⁻); HRMS [M−H]⁻ requires 228.03360, found 228.03364.

2-(4-Methylphenylsulfonamido)acetyl chloride (10). A mixture of 2-(4-methylphenylsulfonamido)acetic acid (9, 200 mg, 0.873 mmol) and thionyl chloride (1 ml) was heated at reflux for 1.5 h. The excess thionyl chloride was removed in vacuo and the resulting white solid dried under high vacuum at 50° C. for 1.5 h. The product acid chloride 10 was used without further purification.

Hydroxy-4-[4-methylphenylsulfonamido)acetamido]benzoic acid (11). A mixture of p-aminosalicylic acid (111 mg, 0.728 mmol) and NaOH (29 mg, 0.728 mmol) in water (6 ml) was stirred at room temperature for 10 min until all of the solid material had dissolved. $Na_2CO_3$ (64 mg, 0.604 mmol) was then added and the mixture cooled to 0° C. A solution of 2-(4-methylphenylsulfonamido)acetyl chloride (10, 216 mg, 0.873 mmol) in THF (2 ml) was injected rapidly and the resulting solution allowed to warm to room temperature and stirred for 2 h. Then reaction mixture was poured into a separating funnel containing diethyl ether. The phases were separated and the aqueous phase washed with a further portion of diethyl ether. The aqueous phase was acidified to pH 1 by addition of 1N HCl solution and the product extracted into ethyl acetate. The ethyl acetate was washed twice with 1N HCl solution and the organic phase was dried ($Na_2SO_4$), filtered and the solvent removed in vacuo. The resulting pale yellow solid was triturated with chloroform leaving 11 as an off white powder (187 mg, 71%). $\delta_H$ (400 MHz, MeOD) 2.36 (3H, s, $CH_3$), 3.72 (2H, s, $CH_3$), 6.90 (1H, dd, J=8.6 Hz and 1.8 Hz, ArH), 7.17 (1H, d, J=1.6, ArH), 7.33 (2H, d, J=8 Hz, ArH), 7.73-7.76 (3H, m, ArH); $\delta_c$ (100.6 MHz, MeOD) 21.6, 46.6, 106.7, 110.9, 127.3, 130.2, 131.7, 138.1, 143.4, 145.5, 162.7, 167.7, 172.2; MS ($ES^+$) 364.7 (100%, $[M+H]^+$), (ion not detected in $ES^-$).

Ethyl 2-(4'-chlorobiphenyl-4-ylsulfonyloxy)acetate (12). A suspension of ethyl glycolate (73 mg, 0.6964 mmol) and 4-chloro[1,1'-biphenyl]-4-sulfonyl chloride (200 mg, 0.6964 mmol) in anhydrous diethyl ether (1 ml) at 0° C. was treated dropwise with triethylamine (0.194 ml, 1.393 mmol). The temperature was maintained at 0° C. with stirring for a further 2 h. After this time, water was added and the phases separated. The aqueous phase was extracted with fresh diethyl ether. The combined organic extracts were dried ($MgSO_4$), filtered and the solvent removed in vacuo. The crude product was purified by column chromatography over silica gel ($R_f$=0.45, 25% ethyl acetate in hexane) affording 12 as a colorless oil which solidified on standing as an off white solid (213 mg, 86%). $\delta_H$ (400 MHz, $CDCl_3$) 1.25 (3H, t, J=7.2 Hz, $CH_3$), 4.21 (2H, q, J=7.2 Hz, $CH_2$), 4.65 (2H, s, $CH_2$), 7.46-7.55 (4H, m, ArH), 7.73 (2H, d, J=8.8 Hz, ArH), 8.03 (2H, d, J=8.4 Hz, ArH); $\delta_c$ (100.6 MHz, $CDCl_3$) 14.2, 62.2, 65.0, 127.9, 128.8, 129.0, 129.6, 134.8, 135.4, 137.6, 146.1, 166.2; MS ($ES^+$) 372.0 (100%, $[M+H_2O]^+$); MS ($ES^-$) 266.9 (100%, $[M-H]^-$).

2-(4'-Chlorobiphenyl-4-ylsulfonyloxy)acetic acid (13). A solution of ester 12 (200 mg, 0.5633 mmol) in ethanol (0.7 ml) was treated at room temperature with 5% NaOH aqueous solution (0.45 ml). The resulting mixture was stirred at room temperature for 3 h. The ethanol was removed in vacuo and aqueous 5% HCl solution (0.46 ml) was added. The aqueous mixture was extracted with chloroform and the organic extracts dried ($Na_2SO_4$), filtered and the solvent removed under reduced pressure. The remaining white solid was recrystallized from chloroform as a white powder (133 mg, 72%). (Material that did not crystallize was collected by column chromatography using a gradient ethyl acetate to 50% MeOH in ethyl acetate). $\delta_H$ (400 MHz, MeOD) 4.65 (2H, s, $CH_2$), 7.50 (2H, d, J=8.4 Hz, ArH), 7.70 (2H, d, J=8.4 Hz, ArH), 7.88 (2H, d, J=8.4 Hz, ArH), 8.02 (2H, d, J=8.4 Hz, ArH); $\delta_c$ (100.6 MHz, MeOD) 65.2, 127.7, 128.6, 128.8, 129.1, 134.9, 135.0, 137.7, 145.7, 168.3; MS ($ES^+$) 343.7 (100%, $[M+H_2O]^+$), 323.7 (5%, $[M+H]^+$), (ion not detected in $ES^-$).

2-Chloro-2-oxoethyl 4'-chlorobiphenyl-4-sulfonate (14). A mixture of acid 13 (100 mg, 0.306 mmol) and thionyl chloride (1 ml) was heated at reflux for 1.5 h. The excess thionyl chloride was removed in vacuo and the resulting pale yellow/white solid dried under high vacuum at 50° C. for 1.5 h. The product acid chloride 14 was used without further purification.

4-(2-(4'-Chlorobiphenyl-4-ylsulfonyloxy)acetamido)-2-hydroxybenzoic acid (15). A mixture of p-aminosalicylic acid (43 mg, 0.278 mmol) and NaOH (11 mg, 0.278 mmol) in water (6 ml) was stirred at room temperature for 10 min until all of the solid material had dissolved. $Na_2CO_3$ (25 mg, 0.231 mmol) was then added and the mixture cooled to 0° C. A suspension of 14 (105 mg, 0.306 mmol) in THF (2 ml) was injected rapidly and the resulting solution allowed to warm to room temperature and stirred for 2 h. Then reaction mixture was poured into a separating funnel containing diethyl ether. The phases were separated and the aqueous phase washed with a further portion of diethyl ether. The aqueous phase was acidified to pH 1 by addition of 1N HCl solution and the product extracted into ethyl acetate. The ethyl acetate was washed twice with 1N HCl solution and the organic phase was dried ($Na_2SO_4$) and filtered. The product was found to be in both the diethyl ether and ethyl acetate fractions so these organic phases were combined and the solvent removed in vacuo. The product was purified by column chromatography over silica gel ($R_f$=0.27, 10% MeOH in ethyl acetate) affording 15 as a yellow powder (45 mg, 35%). An analytical sample was obtained by further purification by recrystallization from EtOAc/MeOH. $\delta_H$ (400 MHz, MeOD) 4.72 (2H, s, $CH_2$), 6.89 (1H, dd, J=8.6 Hz and 1.8 Hz, ArH), 7.13 (1H, d, J=1.8 Hz, ArH), 7.46 (2H, d, J=8.4 Hz, ArH), 7.58 (2H, d, J=8.4 Hz, ArH), 7.70 (1H, d, J=8.6 Hz, ArH), 7.82 (2H, d, J=8.4 Hz, ArH), 8.03 (2H, d, J=8.4 Hz, ArH); MS ($ES^-$) 401.9 (100%), 459.8 (75%, $[M-H]^-$).

Ethyl 2-(biphenyl-4-ylsulfonyloxy)acetate (16). A suspension of ethyl glycolate (374 μl, 3.957 mmol) and biphenyl-4-sulfonyl chloride (1 g, 3.957 mmol) in anhydrous diethyl ether (2 ml) at 0° C. was treated dropwise with triethylamine (1.1 ml, 7.914 mmol). The temperature was maintained at 0° C. with stirring for a further 2 h. After this time, water was added and the phases separated. The aqueous phase was extracted with fresh diethyl ether. The combined organic extracts were dried ($MgSO_4$), filtered and the solvent removed in vacuo. The crude product was purified by column chromatography over silica gel ($R_f$=0.26, 25% ethyl acetate in hexane) affording 16 as a colourless oil (1.055 g, 83%). $\delta_H$ (400 MHz, $CDCl_3$) 1.25 (3H, t, J=6.8 Hz, $CH_3$), 4.20 (2H, q, J=6.8 Hz, $CH_2$), 4.65 (2H, s, $CH_2$), 7.44-7.51 (3H, m, ArH), 7.61 (2H, d, J=7.6 Hz, ArH), 7.76 (2H, d, J=8 Hz, ArH), 8.01 (2H, d, J=8 Hz, ArH); $\delta_c$ (100.6 MHz, $CDCl_3$) 14.2, 62.2, 65.0, 127.6, 128.1, 128.9, 129.4, 134.4, 139.2, 147.4, 166.2; MS ($ES^+$) 338.1 (100%, $[M+H_2O]^+$).

2-(Biphenyl-4-ylsulfonyloxy)acetic acid (17). A solution of ester 16 (1.05 g, 3.281 mmol) in ethanol (4 ml) was treated at room temperature with 5% NaOH aqueous solution (2.6 ml). The resulting mixture was stirred at room temperature for 3 h. The ethanol was removed in vacuo and aqueous 5% HCl solution (2.6 ml) was added. The aqueous mixture was extracted with chloroform and the organic extracts dried ($Na_2SO_4$), filtered and the solvent removed under reduced pressure. The remaining white solid was recrystallized from hexane/ethyl acetate as a white powder (806 mg, 84%). $\delta_H$ (400 MHz, MeOD) 4.66 (2H, s, $CH_2$), 7.41-7.51 (3H, m, ArH), 7.69 (2H, d, J=7.2 Hz, ArH), 7.87 (2H, d, J=8.4 Hz, ArH), 8.01 (2H, d, J=8.4 Hz, ArH); $\delta_c$ (100.6 MHz, MeOD) 64.9, 127.2, 127.7, 128.6, 128.7, 129.0, 134.5, 139.1, 147.2, 168.2.

2-Chloro-2-oxoethyl biphenyl-4-sulfonate (18). A mixture of acid 17 (200 mg, 0.685 mmol) and thionyl chloride (1 ml) was heated at reflux for 1.5 h. The excess thionyl chloride was removed in vacuo and the residue dried under high vacuum at 50° C. for 1.5 h. The product acid chloride 18 was used without further purification.

4-(2-(biphenyl-4-ylsulfonamido)acetamido)-2-hydroxybenzoic acid (19). A mixture of p-aminosalicylic acid (95 mg, 0.623 mmol) and NaOH (25 mg, 0.623 mmol) in water (6 ml) was stirred at room temperature for 10 min until all of the solid material had dissolved. $Na_2CO_3$ (55 mg, 0.517 mmol) was then added and the mixture cooled to 0° C. A suspension of 18 (213 mg, 0.685 mmol) in THF (2 ml) was injected rapidly and the resulting solution allowed to warm to room temperature and stirred for 2 h. Then reaction mixture was poured into a separating funnel containing diethyl ether. The phases were separated and the aqueous phase washed with a further portion of diethyl ether. The aqueous phase was acidified to pH 1 by addition of 1N HCl solution and the product extracted into ethyl acetate. The ethyl acetate was washed twice with 1N HCl solution and the organic phase was dried ($Na_2SO_4$), filtered and the solvent removed in vacuo. The product was found to be in both the diethyl ether and ethyl acetate fractions so these organic phases were combined and the solvent removed in vacuo. The product was purified by column chromatography over silica gel ($R_f$=0.22, 10% MeOH in ethyl acetate) affording 19 as a yellow powder (109 mg, 41%). An analytical sample was obtained by further purification by recrystallization from EtOAc/hexane. $\delta_H$ (400 MHz, DMSO) 4.76 (2H, s, $CH_2$), 6.96 (1H, d, J=8.4 Hz, ArH), 7.22 (1H, s, ArH), 7.42-7.74 (6H, m, ArH), 7.93-8.01 (4H, m, ArH), 10.37 (1H, s, NH); MS ($ES^+$) 428.0 (100%, $[M+H]^+$).

4-(2-(Biphenyl-4-ylsulfonyloxy)acetamido)benzoic acid (20). A mixture of p-aminobenzoic acid (43 mg, 0.31 mmol) and NaOH (12.5 mg, 0.31 mmol) in water (3 ml) was stirred at room temperature for 10 min until all of the solid material had dissolved. $Na_2CO_3$ (27 mg, 0.258 mmol) was then added and the mixture cooled to 0° C. A suspension of sulfonyl chloride 18 (106 mg, 0.341 mmol) in THF (1 ml) was injected rapidly and the resulting solution allowed to warm to room temperature and stirred for 2 h. Then reaction mixture was poured into a separating funnel containing diethyl ether. The phases were separated and the aqueous phase washed with a further portion of diethyl ether. The aqueous phase was acidified to pH 1 by addition of 1N HCl solution and the product extracted into ethyl acetate. The ethyl acetate was washed twice with 1N HCl solution and the organic phase was dried ($Na_2SO_4$), filtered and the solvent removed in vacuo. The resulting solid was recrystallized from hexane/ethyl acetate affording acid 20 as an off white powder (81 mg, 64%). $\delta_H$ (400 MHz, DMSO) 4.79 (2H, s, $CH_2$), 7.45-7.70 (9H, m, ArH), 7.86-8.03 (4H, m, ArH), 10.43 (1H, NH); $\delta_c$ (100.6 MHz, DMSO) 68.2, 119.4, 126.5, 127.9, 128.6, 129.2, 129.6, 129.8, 131.1, 134.3, 138.7, 142.7, 146.7, 164.4, 167.5; MS ($ES^+$) 411.7 (100%, $[M+H]^+$).

The following compounds were prepared according to similar method as shown in Scheme 3

Scheme 3

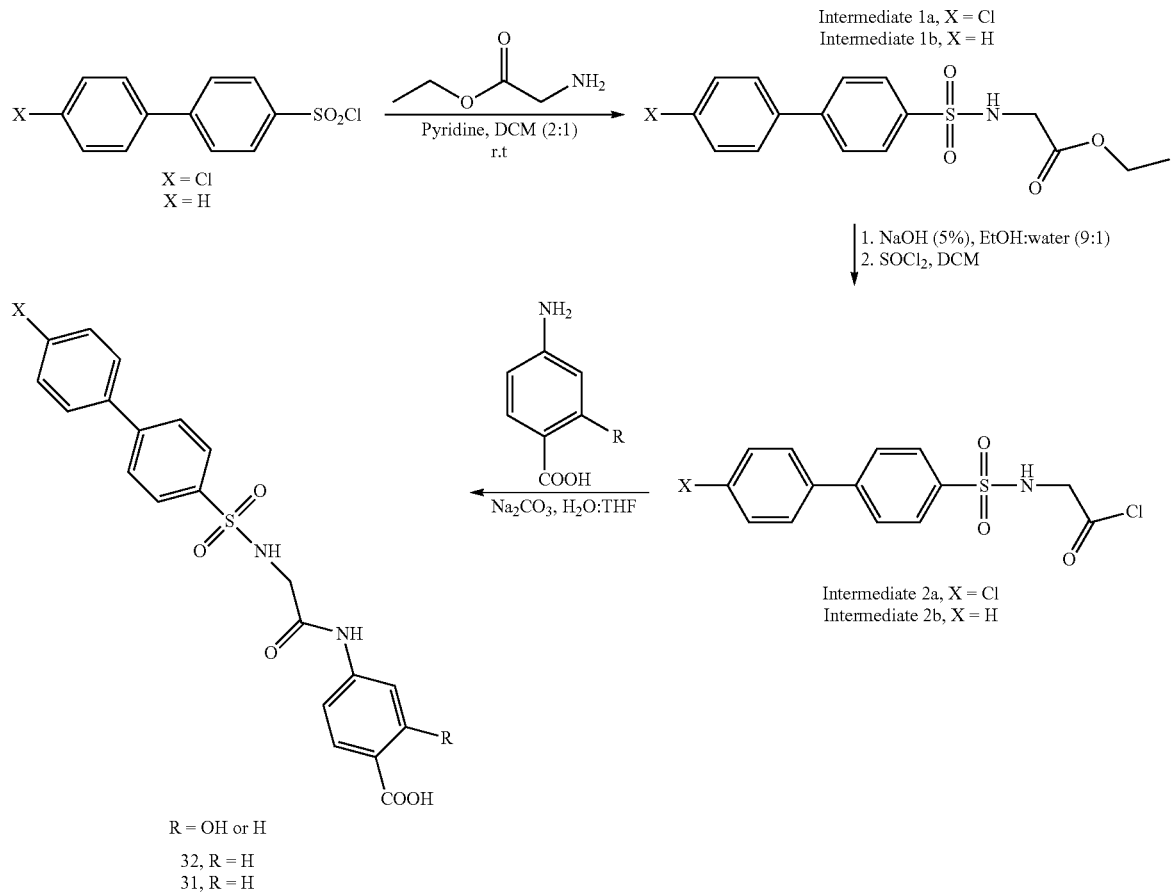

R = OH or H
32, R = H
31, R = H 32 and 31 were synthesized as outlined in the Scheme 3

Synthesis of the intermediate 1a: The sulfonyl chloride (0.995 g, 3.94 mmol) was suspended in pyridine:DCM (10 ml: 5 ml) and ethyl glycinate (0.500 g, 3.58 mmol) was added at room temperature under argon atmosphere, and stirred at room temperature for 4 h. The reaction mixture was diluted with EtOAc and washed with 4M HCl followed by brine. The organic phase was dried ($MgSO_4$) and concentrated to obtain the intermediate 1a (0.941 g). This intermediate was carried to the next stage without purification.

The intermediate 1b was synthesized using the same procedure.

Synthesis of the intermediate 2a: The intermediate 1a (900 mg, 2.82 mmol) was suspended in EtOH:$H_2O$ (9 ml: 1 ml) and NaOH (5% wt, 50 mg) was added to the reaction mixture and refluxed for 3 h. The reaction mixture was cooled to room temperature, acidified (pH=2-3) and extracted with EtOAc. The combined organic phase was dried ($MgSO_4$) and concentrated to obtain the required acid (770 mg) as a white powder. The carboxylic acid obtained was refluxed with thionyl chloride:DCM (3:1) for 2-3 h. The excess thionyl chloride was removed under vacuum to give the intermediate 2a (820 mg). This product was carried to the next stage.

The intermediate 2b was synthesized using the same procedure.

4-[2-{4-(Phenyl)phenylsulfonamido)}acetamido]benzoic acid (32). para-Aminosalicylic acid (54 mg, 0.35 mmol) was suspended in water (4 ml) and 3 drops of THF was added to dissolve the compound. $Na_2CO_3$ was added to the reaction mixture and cooled to 0° C. A solution of intermediate 2a (100 mg, 0.322 mmol) in THF (1.5 ml) was added over 15 min. The reaction mixture was stirred at room temperature for 3 h. A solution of 4M HCl was added portionwise to obtain a precipitate. The white precipitate was filtered and washed with water and dried under vacuum to obtain 32 (45 mg) as a pure compound: $^1$H NMR (DMSO-$d_6$, 400 MHz) δ 12.7 (broad s, 1H), 8.17 (t, J=12.0 Hz, 1H), 7.88-7.81 (m, 5H), 7.64 (d, J=7.2 Hz, 2H), 7.57 (d, J=8.4 Hz, 2H), 7.47 (t, J=7.2 Hz, 2H), 7.42 (d, J=4.0 Hz, 1H), 3.72 (d, J=4.0 Hz, 1H).

4-[2-{4-(4'-chlorophenyl)phenylsulfonamido)}acetamido]benzoic acid (31). The synthesis of 31 achieved in a similar manner to 32. $^1$H NMR (CD$_3$OD, 400 MHz) δ 7.95 (d, J=8.4 Hz, 2H), 7.88 (d, J=9.2 Hz, 2H), 7.72 (d, J=8.0 Hz, 2H), 7.53-7.50 (m, 4H), 7.43 (d, J=8.0 Hz, 2H), 3.80 (s, 2H).

Compounds 21, 22, 23, 24, 25, 26, 27, 28, 29 and 30 were synthesized using the procedure outlined for compound 32 from appropriate acyl chlorides and amines.

2-Hydroxy-4-(2-(4-biphenylsulfonyloxy)acetamido)benzoic acid (21). $^1$H NMR (CD$_3$OD, 400 MHz) δ 7.93 (d, J=8 Hz, 2H), 7.73 (d, J=8.4 Hz, 2H), 7.18 (d, J=8.4 Hz, 1H), 7.55 (d, J=7.6 Hz, 2H), 7.44-7.35 (3H, m), 7.16 (appd, 1H), 6.88 (dd, J=8.4, 1.2 Hz, 1H), 3.77 (s, 2H).

4-(2-(Benzyloxy)acetamido)benzoic acid (22). $^1$H NMR (CD$_3$OD, 400 MHz) δ 7.97 (d, J=6.4 Hz, 2H), 7.71 (2H, J=6.8 Hz, 2H), 7.44-7.31 (m, 5H), 4.68 (s, 2H), 4.11 (s, 2H).

4-(2-(Benzyloxy)acetamido)-2-hydroxybenzoic acid (23). $^1$H NMR (CD$_3$OD, 400 MHz) δ 7.78 (d, J=8.0 Hz, 1H), 7.42-7.30 (m, 6H), 7.07-7.05 (d, J=8.0 Hz, 1H), 4.66 (s, 2H), 4.08 (s, 2H).

4-(3-(Phenylsulfonyl)propanamido)-2-hydroxybenzoic acid (24). $^1$H NMR (CD$_3$OD, 400 MHz) δ 7.95-7.91 (m, 4H), 7.70-7.56 (m, 5H), 3.60 (t, J=8.0 Hz, 2H), 2.81 (t, J=8.0 Hz).

4-(3-(Phenylsulfonyl)propanamido)benzoic acid (25). $^1$H NMR (CD$_3$OD, 400 MHz) δ 7.94 (d, J=8.0 Hz, 4H), 7.73 (d, J=8.8 Hz, 4H), 7.69 (d, J=7.6 Hz, 2H), 7.63-7.59 (m, 2H), 7.20 (d, J=2.0 Hz, 1H), 6.93 (dd, J=8.4, 1.6 Hz, 1H), 3.60 (t, J=7.2 Hz, 2H), 2.79 (t, J=6.8 Hz, 2H).

4-(4-Phenylbutanamido)-2-hydroxybenzoic acid (26). $^1$H NMR (CD$_3$OD, 400 MHz) δ 7.31 (appd, J=1.6 Hz, 1H), 7.27-7.13 (m, 5H), 7.01 (dd, J=8.4, 1.6 Hz, 1H), 2.67 (t, J=7.2 Hz, 2H), 2.38 (t, J=6.8 Hz, 2H), 2.02-1.95 (m, 2H).

4-(4-Phenylbutanamido)benzoic acid (27). $^1$H NMR (CD$_3$OD, 400 MHz) δ 7.95 (d, J=8.8 Hz, 2H), 7.66 (d, J=8.8 Hz, 2H), 7.27-7.15 (m, 5H), 2.68 (t, J=8 Hz, 2H), 2.40 (t, J=8.0 Hz, 2H), 2.00 (m, 2H).

2-(Biphenyl-4-ylsulfonamido)-N-(4-cyanophenyl)acetamide (28). $^1$H NMR (CD$_3$OD, 400 MHz) δ 8.09 (broad t, 1H), 8.02 (d, J=8.0 Hz, 1H), 7.87 (d, J=8.8 Hz, 2H), 7.75-7.64 (m, 5H), 7.47-7.43 (m, 4H), 4.53 (s, 1H), 3.96 (appd, 1H).

4-(2-(Biphenyl-4-ylsulfonamido)acetamido)benzenesulfonic acid (29). $^1$H NMR (CD$_3$OD, 400 MHz) δ 7.94 (d, J=8.4 Hz, 2H), 7.75 (d, J=8.0 Hz, 2H), 7.71 (d, J=8.0 Hz, 2H), 7.58 (d, J=8.0 Hz, 2H), 7.50-7.38 (m, 6H), 3.78 (s, 2H).

2-(Biphenyl-4-ylsulfonamido)-N-(4-sulfamoylphenyl)acetamide (30). $^1$H NMR (CD$_3$OD, 400 MHz) δ 10.27 (s, 1H), 8.16 (broad t, 1H), 7.84 (m, 4H), 7.69-7.63 (m, 6H), 7.48 (broad t, 2H), 7.43 (d, J=6 Hz, 1H), 7.23 (s, 2H), 3.72 (appd, J=6 Hz, 2H).

The following compounds were prepared according to Scheme 4

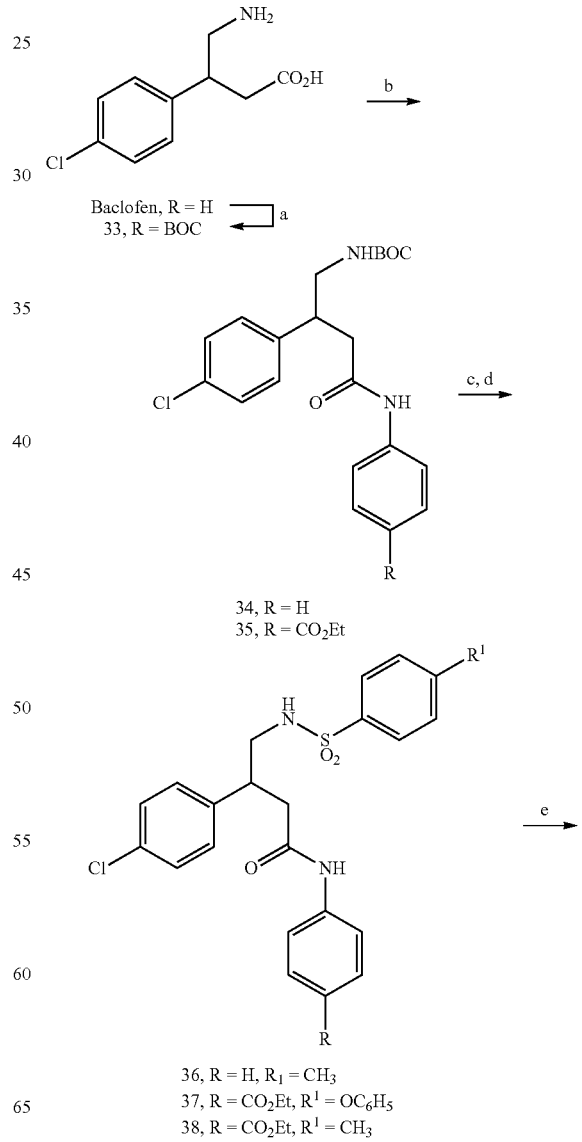

Scheme 4

Baclofen, R = H
33, R = BOC

34, R = H
35, R = $CO_2Et$

36, R = H, $R^1$ = $CH_3$
37, R = $CO_2Et$, $R^1$ = $OC_6H_5$
38, R = $CO_2Et$, $R^1$ = $CH_3$

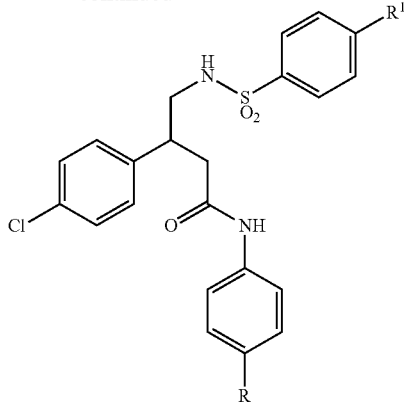

39, R = CO₂H, R¹ = CH₃
40, R = CO₂H, R¹ = OC₆H₅

Key:
a Boc₂O, dioxane, H₂O, rt, 2 h;
b aniline or ethyl 4-aminobenzoate, HATU, DIPEA, DMF, rt, Ar, overnight;
c TFA, DCM, rt, 1 h;
d 4-phenoxy benzenesulfonylchloride or tosyl chloride, K₂CO₃, dioxane, H₂O, rt, 2-3 h;
e THF, MeOH, NaOH 1M, rt, overnight.

4-(tert-Butoxycarbonylamino)-3-(4-chlorophenyl)butanoic acid (33). Ref J. of Peptide Research, 2003, 61, 331. BOC₂O (5.32 g, 24.41 mmol, 1 eq) was added to a stirred solution of Baclofen (5.20 g, 24.41 mmol) and NaOH 1M (73 ml) in water (73 ml) and 1,4-dioxane (73 ml) at 0° C. After stirring for 4 h at room temperature, a 10% aqueous solution o citric acid was added until pH 3. The formed white solid was filtered, washed with water (50 ml) and dried. The pure acid 33 was obtained without further purification (6.43 g, 20.56 mmol, 84%), mp 139-141° C. ¹H NMR (400 MHz, CD₃OD) δ 1.37 (9H, s), 2.50 (1H, dd, J 8.8, 15.2 Hz), 2.66 (1H, dd, J 5.0, 15.4 Hz), 3.12-3.27 (3H, m), 7.22 (2H, d, J 8.4 Hz), 7.27 (2H, d, J 8.4 Hz).

tert-Butyl 2-(4-chlorophenyl)-4-oxo-4-(phenylamino)butylcarbamate (34). To a solution of 33 (0.206 g, 0.657 mmol, 1.2 eq) and aniline (0.051 g, 0.548 mmol) in dry DMF (5 ml) HATU (0.315 g, 0.9087 mmol, 1.5 eq) and DIPEA (0.340 g, 2.63 mmol, 4 eq) was added at room temperature under Ar. After stirring overnight at room temperature, the reaction mixture was quenched with water (10 mL) and extracted with ethyl acetate (2×15 ml). The organic extracts were collected, dried over Na₂SO₄ and the solvent was distilled off under reduced pressure. The crude compound was purified by chromatography on silica gel (3:7 ethyl acetate/hexane, v/v, R_f 0.30) to give 34 as a white solid (0.120 g, 0.307 mol, 47%), mp 165-167° C. ¹H NMR (400 MHz, CDCl₃) δ 1.43 (9H, s), 2.55 (1H, dd, J 5.0, 13.8 Hz), 2.75 (1H, dd, J 8.4, 13.6 Hz), 3.16-3.39 (2H, m), 3.52-3.57 (1H, m), 4.60 (1H, bs), 7.07-7.13 (3H, m), 7.29-7.32 (4H, m), 7.54 (2H, d, J 8.4 Hz), 8.61 (1H, bs).

Ethyl 4-(4-(tert-butoxycarbonylamino)-3-(4-chlorophenyl)butanamido)benzoate (35). The compound was prepared from 33 and ethyl 4-aminobenzoate in a similar manner as described for preparation of 34. Chromatography on silica gel (7:3 hexanes/ethyl (R_f 0.20) afforded 35 as a brown solid in 72% yield. ¹H NMR (400 MHz, CD₃OD) δ 1.35 (9H, s, C(CH₃), 1.35 (3H, t, J 6.8 Hz, CH₂CH₃), 2.63 (1H, dd, J 8.6, 14.6 Hz, H—CHCO), 2.77 (1H, dd, J 6.2, 14.6 Hz, H—CHCO), 3.35-3.40 (1H, m, CH₂CHCH₂), 4.31 (2H, q, J 7.2 Hz, CH₂CH₃), 7.24 (2H, d, J 8.8 Hz, 2×Ar—H), 7.28 (2H, d, J 8.8 Hz, 2×Ar—H), 7.57 (2H, d, J 8.4 Hz, 2×Ar—H), 7.91 (2H, d, J 9.2 Hz, 2×Ar—H). ¹³C NMR (400 MHz, CDCl₃) δ 14.56 (s) (CH₂CH₃), 28.56 (s) (C(CH₃)₃), 40.92 (s) (CH₂CO), 42.77 (s) (CH₂CHCH₂), 45.97 (s) (CH₂NH), 61.04 (s) (C(CH₃)₃), 80.56 (s) (CH₂CH₃), 119.07 (s) (2×CH, Ar), 125.90 (s) (C, Ar), 129.08 (s) (2×CH, Ar), 129.17 (s) (2×CH, Ar), 130.90 (s) (2×CH, Ar), 133.17 (s) (C, Ar), 140.35 (s) (C, Ar), 142.65 (s) (C, Ar), 157.54 (s) (C=O), 166.47 (s) (C=O), 170.32 (s) (C=O). ν_max (pure sample)/(cm⁻¹)), 3353 (md), 1685 (st) (C=O), 1685 (st) (C=O), 1661 (st) (C=O), 1524 (st), 1273 (st), 1249 (st), 1188 (st), 769 (md).

4-Phenoxybenzenesulfonyl chloride. A solution of 4-phenoxybenzenesulfonic acid (3.14 g, 12.64 mmol) in thionyl chloride (9 ml) was refluxed for 4 h in presence of DMF (2 drops). After cooling to room temperature, diethyl ether (20 ml) was added and the resulting white solid was separated by filtration. The filtered solution was evaporated in vacuo to give 4-phenoxybenzenesulfonyl chloride as a brown oil which was used in the next step without further purification.

3-(4-Chlorophenyl)-4-(4-methylphenylsulfonamido)-N-phenylbutanamide (36). To a solution of 34 (0.106 g, 0.271 mmol) in DCM (2 ml) TFA (2 ml) was added. After stirring for 2 h at room temperature, the solvent was distilled under reduced pressure to give a brown solid. The crude residue was dissolved as obtained in 1,4-dioxane:H₂O 1:1 (5 ml) and K₂CO₃ (0.225 g, 1.63 mmol, 6 eq) was added followed by tosyl chloride (0.056 g, 0.298 mmol, 1.1 eq) at room temperature. After stirring for 2 h at room temperature, the resulting mixture was evaporated in vacuo to dryness. Water (10 ml) was added and the resulting white solid was separated by filtration and dried. Pure 36 was obtained without further purification (0.079 g, 0.179 mmol, 66%), mp 200-202° C. ¹H NMR (400 MHz, CD₃OD) δ 2.39 (3H, s, Ar—CH₃), 2.56 (1H, dd, J 9.2, 14.4 Hz, H—CHCO), 2.77 (1H, dd, J 6.8, 14.4 Hz, H—CHCO), 3.06 (1H, dd, J 8.2, 13.0 Hz, H—CHNH), 3.15 (1H, dd, J 6.8, 13.2 Hz, H—CHNH) 7.03-7.07 (1H, m, CH, Ar), 7.15 (2H, d, J 8.4 Hz, 2×CH, Ar), 7.21-7.26 (4H, s, 4×CH, Ar), 7.29 (2H, d, J 8.0 Hz, 2×CH, Ar), 7.36-7.38 (2H, m, 2×CH, Ar), 7.62 (2H, d, J 8.8 Hz, 2×CH, Ar). ¹³C NMR (400 MHz, DMSO-d₆) δ21.63 (s) (Ar—CH₃), 40.73 (s) (CH₂CO), 41.87 (s) (CH₂CHCH₂), 48.13 (s) (CH₂NH), 119.79 (s) (2×CH, Ar), 123.80 (s) (CH, Ar), 127.14 (s) (2×CH, Ar), 128.80 (s) (2×CH, Ar), 129.29 (s) (2×CH, Ar), 130.23 (s) (2×CH, Ar), 130.36 (s) (2×CH, Ar), 131.80 (s) (C, Ar), 138.14 (s) (C, Ar), 139.64 (s) (C, Ar), 141.53 (s) (C, Ar), 143.20 (s) (C, Ar), 169.81 (s) (C=O). ν_max (pure sample)/(cm⁻¹) 3340 (md) (N—H), 3141 (md) (N—H), 1665 (st) (C=O), 1598 (st), 1547 (st), 1493 (md), 1444 (st), 1154 (st), 1087 (md). MS (API-ES): m/z 443 [M+H]⁺ (100%), HRMS (API-ES) m/z found 443.1201 [M+H]⁺.

Ethyl 4-(4-(4-benzylphenylsulfonamido)-3-(4-chlorophenyl)butanamido)benzoate (37). The compound was obtained as a white solid in 65% from 35 and 4-phenoxybenzenesulfonyl chloride in a similar manner as described for preparation of 36, mp. ¹H NMR (400 MHz, CD₃OD) δ 1.36 (3H, t, J 6.8 Hz, CH₂CH₃), 2.60 (1H, dd, J 8.0, 14.8 Hz, H—CHCO), 2.82 (1H, dd, J 6.0, 14.8 Hz, H—CHCO), 3.09 (1H, dd, J 7.8, 13.4 Hz, H—CHNH), 3.16 (1H, dd, J 6.4, 13.2 Hz, H—CHNH), 4.32 (2H, q, J 7.2 Hz, CH₂CH₃), 6.99 (2H, d, J 7.2 Hz), 7.06-7.08 (2H, m), 7.18 (2H, d, J 8.4 Hz), 7.18 (2H, d, J 8.4 Hz), 7.19-7.24 (3H, m), 7.40-744 (2H, m), 7.56 (2H, d, J 8.8 Hz), 7.72 (2H, d, J 8.8 Hz), 7.91 (2H, d, J 8.8 Hz). MS (API-ES): m/z 593[M+H]⁺ (100%), HRMS (API-ES) m/z found 593.15134 [M+H]⁺.

Ethyl 4-(3-(4-chlorophenyl)-4-(4-methylphenylsulfonamido)butanamido)benzoate (38). The compound was obtained as a white solid in 96% from 35 and tosyl chloride in a similar manner as described for preparation of 28, mp 187-189° C. ¹H NMR (400 MHz, CD₃OD) δ1.36 (3H, t, J 7.2 Hz, CH₂CH₃), 2.39 (3H, s, Ar—CH₃), 2.60 (1H, dd, J 8.8, 14.8 Hz, H—CHCO), 2.82 (1H, dd, J 6.0, 14.8 Hz, H—CHCO), 3.06 (1H, dd, J 8.0, 13.2 Hz, H—CHNH), 3.14

(1H, dd, J 6.8, 13.2 Hz, H—CHNH) 4.32 (2H, q, J 7.2 Hz, CH$_2$CH$_3$), 7.15 (2H, d, J 8.8 Hz), 7.22 (2H, d, J 8.4 Hz), 7.29 (2H, d, J 8.4 Hz), 7.54 (2H, d, J 8.8 Hz), 7.62 (2H, d, J 8.4 Hz), 7.91 (2H, d, J 9.2 Hz). $^{13}$C NMR (400 MHz, DMSO-d$_6$) δ 14.88 (s) (CH$_2$CH$_3$), 21.62 (s) (Ar—CH$_3$), 40.74 (s) (CH$_2$CO), 41.76 (s) (CH$_2$CHCH$_2$), 48.25 (s) (CH$_2$NH), 61.08 (s) (CH$_2$CH$_3$), 119.06 (s) (2×CH, Ar), 124.78 (s) (C, Ar), 127.34 (s) (2×CH, Ar), 128.83 (s) (2×CH, Ar), 130.23 (s) (2×CH, Ar), 130.36 (s) (2×CH, Ar), 130.84 (s) (2×CH, Ar), 131.83 (s) (C, Ar), 138.15 (s) (C, Ar), 141.42 (s) (C, Ar), 143.20 (s) (C, Ar), 143.95 (s) (C, Ar), 165.98 (s) (C=O), 170.47 (s) (C=O). ν$_{max}$ (pure sample)/(cm$^{-1}$) 3320 (md), 3292 (md), 1712 (st) (C=O), 1677 (st) (C=O), 1598 (md), 1540 (st), 1315 (st), 1272 (st), 1149 (st), 1104 (st). MS (API-ES): m/z 515 [M+H]$^+$ (100%), HRMS (API-ES) m/z found 515.1411 [M+H]$^+$.

4-(3-(4-Chlorophenyl)-4-(4-methylphenylsulfonamido)butanamido)benzoic acid (39). A solution of 36 (0.023 g, 0.044 mmol) in methanol (1 ml) and THF (1 ml) was stirred in presence of NaOH 1M (1 ml) overnight at rt. The solution remaining was concentrated in vacuo. HCl 1M (1 ml) was added and the formed white solid was filtered, washed with water (5 ml) and dried. Pure 39 was obtained without further need for purification (0.015 g, 0.030 mmol, 68%), mp 250-252° C. $^1$H NMR (400 MHz, CD$_3$OD) δ 2.39 (3H, s, Ar—CH$_3$), 2.60 (1H, dd, J 8.8, 14.8 Hz, H—CHCO), 2.82 (1H, dd, J 6.4, 14.8 Hz, H—CHCO), 3.06 (1H, dd, J 8.0, 13.2 Hz, H—CHNH), 3.14 (1H, dd, J 6.8, 13.2 Hz, H—CHNH), 7.16 (2H, d, J 8.8 Hz), 7.23 (2H, d, J 8.4 Hz), 7.29 (2H, d, J 8.0 Hz), 7.54 (2H, d, J 9.2 Hz), 7.62 (2H, d, J 8.4 Hz), 7.92 (2H, d, J 8.8 Hz). $^{13}$C NMR (100 MHz, DMSO-d$_6$) δ. ν$_{max}$ (pure sample)/(cm$^{-1}$) 1864 (st), 1665 (st), 1653 (st), 1604 (st), 1519 (st), 1455 (st), 1324 (st), 1290 (st), 1164 (st), 1151 (st). MS (API-ES): m/z 485 [M−H]$^−$ (100%), HRMS (API-ES) m/z found 485.0935 [M−H].

The following compounds were prepared according to Scheme 5.

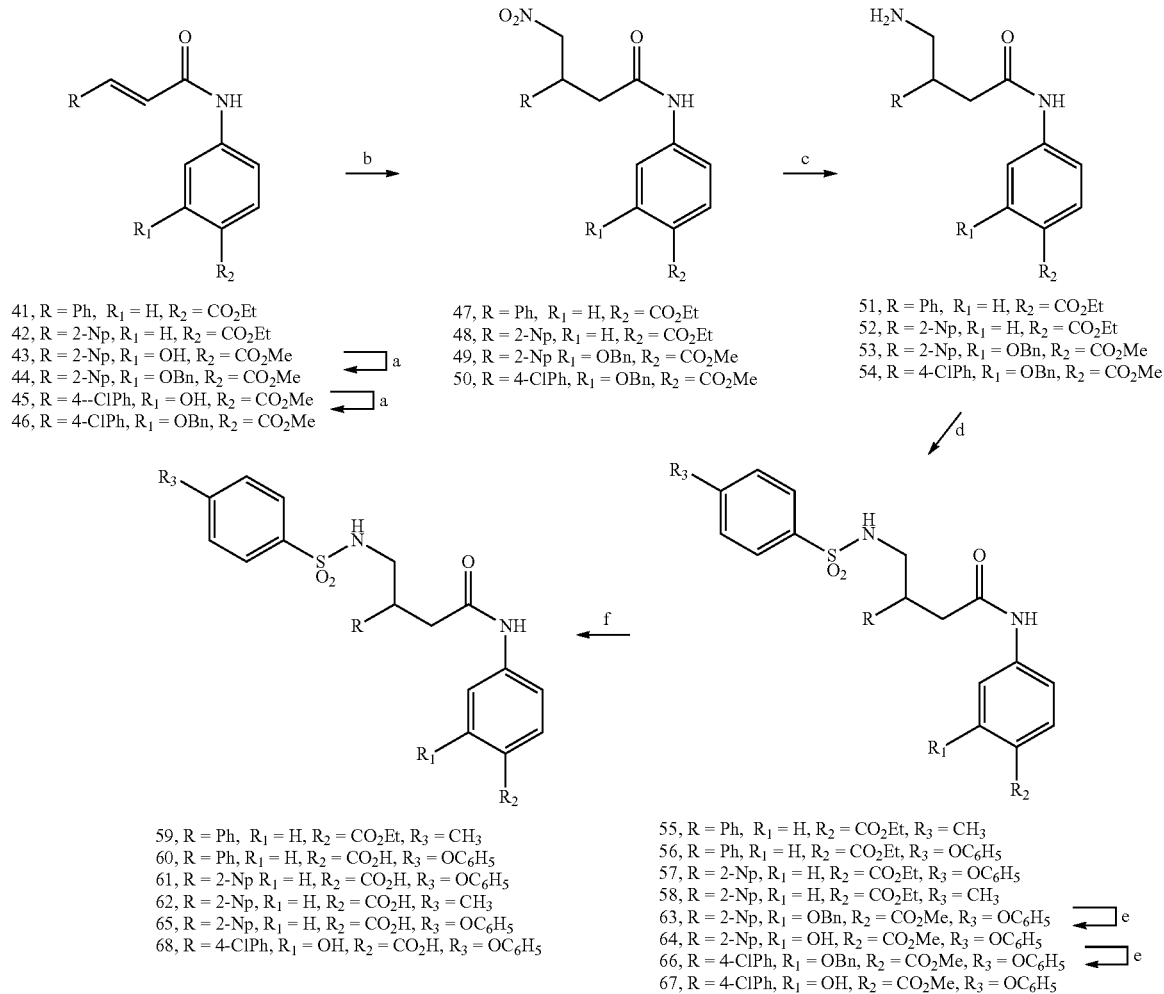

Scheme 5

41, R = Ph, R$_1$ = H, R$_2$ = CO$_2$Et
42, R = 2-Np, R$_1$ = H, R$_2$ = CO$_2$Et
43, R = 2-Np, R$_1$ = OH, R$_2$ = CO$_2$Me
44, R = 2-Np, R$_1$ = OBn, R$_2$ = CO$_2$Me
45, R = 4-ClPh, R$_1$ = OH, R$_2$ = CO$_2$Me
46, R = 4-ClPh, R$_1$ = OBn, R$_2$ = CO$_2$Me

47, R = Ph, R$_1$ = H, R$_2$ = CO$_2$Et
48, R = 2-Np, R$_1$ = H, R$_2$ = CO$_2$Et
49, R = 2-Np R$_1$ = OBn, R$_2$ = CO$_2$Me
50, R = 4-ClPh, R$_1$ = OBn, R$_2$ = CO$_2$Me

51, R = Ph, R$_1$ = H, R$_2$ = CO$_2$Et
52, R = 2-Np, R$_1$ = H, R$_2$ = CO$_2$Et
53, R = 2-Np, R$_1$ = OBn, R$_2$ = CO$_2$Me
54, R = 4-ClPh, R$_1$ = OBn, R$_2$ = CO$_2$Me

59, R = Ph, R$_1$ = H, R$_2$ = CO$_2$Et, R$_3$ = CH$_3$
60, R = Ph, R$_1$ = H, R$_2$ = CO$_2$H, R$_3$ = OC$_6$H$_5$
61, R = 2-Np R$_1$ = H, R$_2$ = CO$_2$H, R$_3$ = OC$_6$H$_5$
62, R = 2-Np, R$_1$ = H, R$_2$ = CO$_2$H, R$_3$ = CH$_3$
65, R = 2-Np, R$_1$ = H, R$_2$ = CO$_2$H, R$_3$ = OC$_6$H$_5$
68, R = 4-ClPh, R$_1$ = OH, R$_2$ = CO$_2$H, R$_3$ = OC$_6$H$_5$

55, R = Ph, R$_1$ = H, R$_2$ = CO$_2$Et, R$_3$ = CH$_3$
56, R = Ph, R$_1$ = H, R$_2$ = CO$_2$Et, R$_3$ = OC$_6$H$_5$
57, R = 2-Np, R$_1$ = H, R$_2$ = CO$_2$Et, R$_3$ = OC$_6$H$_5$
58, R = 2-Np, R$_1$ = H, R$_2$ = CO$_2$Et, R$_3$ = CH$_3$
63, R = 2-Np, R$_1$ = OBn, R$_2$ = CO$_2$Me, R$_3$ = OC$_6$H$_5$
64, R = 2-Np, R$_1$ = OH, R$_2$ = CO$_2$Me, R$_3$ = OC$_6$H$_5$
66, R = 4-ClPh, R$_1$ = OBn, R$_2$ = CO$_2$Me, R$_3$ = OC$_6$H$_5$
67, R = 4-ClPh, R$_1$ = OH, R$_2$ = CO$_2$Me, R$_3$ = OC$_6$H$_5$

Key:
a benzyl bromide, DMF, K$_2$CO$_3$, rt, Ar, overnight;
b DBU, CH$_3$NO$_2$, mw, 100° C., 15 min;
c NiCl$_2$, NaBH$_4$, MeOH, 0° C., 20 min;
d 4-phenoxybenzenesulfor chloride or tosyl chloride, K$_2$CO$_3$, dioxane, H$_2$O, rt, 2-3 h;
e ammonium formate, MeOH, 10% Pd/C, rt, Ar, 2 days;
f THF, MeOH, NaOH 1M, rt, overnight Abbreviation Ph = phenyl, Np = naphthyl.

4-(3-(4-Chlorophenyl)-4-(4-phenoxyphenylsulfonamido) butanamido)benzoic acid (40). A solution of ester 38 (0.065 g, 0.107 mmol) in methanol (1.5 ml) and THF (1.5 ml) was stirred in presence of NaOH 1M (1 ml) for 2 h at 80° C. After cooling to rt, the solution remaining was concentrated in vacuo. HCl 1M (1.5 ml) was added and the formed white solid was filtered, washed with water (10 ml) and dried. The pure acid 40 was obtained without further need for purification (0.050 g, 0.088 mmol, 83%), mp 119-121° C. $^1$H NMR (400 MHz, CD$_3$OD) δ 2.61 (1H, dd, J 8.4, 14.8 Hz, H—CHCO), 2.82 (1H, dd, J 6.0, 14.8 Hz, H—CHCO), 3.09 ($\overline{1H}$, dd, J 7.8, 13.4 Hz, H—CHNH), 3.16 (1H, dd, J 6.4, 13.2 Hz, H—CHNH), 6.99 (2H, d, J 9.2 Hz), 7.06-7.08 (2H, m), 7.17-7.24 (5H, m), 7.47.44 (2H, m), 7.54 (2H, d, J 9.2 Hz), 7.72 (2H, d, J 8.8 Hz), 7.91 (2H, d, J 9.2 Hz). $^{13}$C NMR (400 MHz, CD$_3$OD) δ. ν$_{max}$ (pure sample)/(cm$^{-1}$) 3359 (st) (OH), 1686 (st) (C=O), 1595 (st) (C=O), 1530 (st), 1487 (st), 1410 (md), 1318 (md), 1246 (st), 1150 (st) 1092 (md). MS (API-ES): m/z 563 [M+H]$^+$ (100%), HRMS (API-ES) m/z found 563.10436 [M−H]$^-$.

Ethyl 4-(3-naphthalen-2-yl-acryloylamino)benzoate (42). Anhydrous pyridine (0.331 g, 4.2 mmol, 1.2 eq) and ethyl 4-aminobenzoate (0.577 g, 3.50 mmol) were added to a solution of (E)-3-(2-naphthyl)propenoyl chloride (prepared from its corresponding acid) (0.757 g, 3.50 mmo) in anhydrous DCM (15 ml) under Ar. After stirring overnight at room temperature, the white precipitate was filtered, washed with DCM (10 ml) and dried under vacuum to give the amide 42 (0.960 g, 2.78 mmol, 80%) as a white solid, mp 173-175° C. $^1$H NMR (400 MHz, DMSO-d$_6$) δ 1.30 (3H, t, J 7.2 Hz), 4.28 (2H, t, J 7.2 Hz), 6.97 (1H, d, J 15.4 Hz), 7.54-7.57 (2H, m), 7.7 (1H, d, J 15.4 Hz), 7.77 (1H, dd, J 1.6, 9.2 Hz), 7.84 (2H, d, J 8.8 Hz), 7.93-7.97 (5H, m), 8.15 (1H, s), 10.58 (1H, bs). $^{13}$C NMR (100 MHz, DMSO-d$_6$) δ 14.88, 61.09, 119.30, 122.91, 124.18, 124.99, 127.47, 127.83, 128.38, 129.09, 129.36, 130.05, 130.98, 132.82, 133.68, 134.26, 141.64, 144.33, 164.69, 166.01. ν$_{max}$ (solid)/(cm$^{-1}$) 3357, 1702, 1660, 1619, 1607, 1591, 1521, 1403, 1282. MS (API-ES): m/z 346 [M+H]$^+$ (100%), HRMS (API-ES) m/z found 346.1443 [M+H]$^+$.

Methyl 4-(3-phenylacryloylamino)benzoate (41). This was obtained as a white solid from cinnamoyl chloride (1.1 g, 6.62 mmol) and ethyl 4-aminobenzoate (1.10 g, 6.62 mmol) in a similar manner as described for preparation of 42. The reaction mixture was stirred at room temperature overnight and the mixture was poured in HCl (aq, 2N, 20 ml). The product was extracted with DCM (2×20 ml), dried over Na$_2$SO$_4$ and the solvent removed under reduced pressure. The crude amide 41 was used in the next step without further purification.

Methyl 2-hydroxy-4-(3-naphthalen-2-yl-acryloylamino) benzoate (43). This was obtained from (E)-3-(2-naphthyl) propenoyl chloride (0.320 g, 1.48 mmol) and methyl 4-amino-2-hydroxybenzoate (0.247 g, 1.48 mmol) in a similar manner as described for preparation of 42. After stirring overnight at room temperature, the white solid was filtered, washed with DCM (ml) and dried under vacuum to give the amide 43 (0.400 g, 1.15 mmol, 79%) as an off-white solid, mp 210-212° C. $^1$H NMR (400 MHz, DMSO-d$_6$) δ 3.86 (3H, s, OCH$_3$), 6.31 (1H, d, J 15.6 Hz, CH), 7.17 (1H, dd, J 1.8, 8.8 Hz, H-6'), 7.53 (1H, d, J 1.8 Hz, H-2'), 7.54-7.57 (2H, m, 2×CH, Ar), 7.74-7.79 (3H, m, 3×CH, Ar), 7.92-7.99 (3H, m, 3×CH, Ar), 8.15 (1H, s, CH, Ar), 10.54 (1H, s, NH), 10.65 (1H, s, NH). $^{13}$C NMR (100 MHz, DMSO-d$_6$) δ 52.01 (s) (OCH$_3$), 106.95 (s) (CH, Ar), 108.27 (s) (C, Ar), 111.30 (s) (CH, Ar), 122.78 (s) (CH), 124.21 (s) (CH, Ar), 127.54 (s) (CH, Ar), 127.92 (s) (CH, Ar), 128.40 (s) (CH, Ar), 129.12 (s) (CH, Ar), 129.39 (s) (CH, Ar), 130.12 (s) (CH, Ar), 131.56 (s) (CH, Ar), 132.76 (s) (C, Ar), 133.67 (s) (C, Ar), 134.30 (s) (C, Ar), 141.91 (s) (CH), 146.35 (s) (C, Ar), 161.91 (s) (C, Ar), 164.84 (s) (C=O), 169.70 (s) (C=O). ν$_{max}$ (solid)/(cm$^{-1}$) 3352 (st), 1692 (st), 1662 (st), 1622 (st), 1597 (st), 1507 (st), 1445 (st), 1362 (st), 1265 (st), 1188 (st), 1143 (st), 1095 (st). MS (API-ES): m/z 346 [M−H]$^-$ (100%), HRMS (API-ES) m/z found 346.1088 [M−H]$^-$.

Methyl 4-[3-(4-chlorophenyl)acryloylamino]-2-hydroxybenzoate (45). This was obtained from 4-chlorocinnamoyl chloride (1.80 g, 9.47 mmol) and methyl 4-amino-2-hydroxybenzoate (1.58 g, 9.47 mmol) in a similar manner as described for preparation of 42. After stirring for 2 h at room temperature, the white precipitate was filtered, washed with DCM (10 ml) and dried under vacuum to give the amide 45 (2.41 g, 7.50 mmol, 80%) as an off-white solid, mp 208-210° C. $^1$H NMR (400 MHz, DMSO-d$_6$) 3.85 (3H, s, OCH$_3$), 6.80 (1H, d, J 15.8 Hz, CH), 7.13 (1H, dd, J 2.4, 8.8 Hz, H-6'), 7.49 (1H, d, J 2.4 Hz, H-2'), 7.50 (2H, d, J 8.4 Hz, 2×CH, Ar), 7.60 (1H, d, J 15.8 Hz, CH), 7.65 (2H, s, J 8.4 Hz, 2×CH, Ar), 7.74 (1H, s, J 8.8 Hz, H-5'), 10.50 (1H, s, NH), 10.63 (1H, s, OH). $^{13}$C NMR (100 MHz, DMSO-d$_6$) δ 52.89 (s) (OCH$_3$), 106.97 (s) (CH, Ar), 108.32 (s) (C, Ar), 111.28 (s) (CH, Ar), 123.20 (s) (CH), 129.75 (s) (2×CH, Ar), 130.20 (s) (2×CH, Ar), 131.47 (s) (CH, Ar), 134.15 (s) (C, Ar), 135.14 (s) (C, Ar), 140.47 (s) (C, Ar), 146.24 (s) (CH), 161.92 (s) (C, Ar), 164.58 (s) (C=O), 169.70 (s) (C=O). ν$_{max}$ (solid)/(cm$^{-1}$) 3346 (st), 1693 (st), 1660 (st), 1628 (st), 1597 (st), 1507 (st), 1442 (st), 1269 (st), 1189 (st). MS (API-ES): m/z 330 [M $^{35}$Cl-H]$^-$ (100%), 332 [M $^{37}$Cl-H]$^-$ 332 (35%). HRMS (API-ES) m/z found 330.0552 [M−H]$^-$.

Ethyl 4-(4-nitro-3-phenyl-butyrylamino)benzoate (47). A mixture of 41 (1.340 g, 4.44 mmol) in nitromethane (4 ml) was heated a microwave reactor (Biotage Initiator) at 100° C. for 15 min in presence of DBU (0.811 g, 5.328 mmol, 1.2 eq). After cooling to room temperature, the reaction mixture was poured into HCl 1M (10 ml). The product extracted with ethyl acetate (2×15 ml). The organic extracts were collected, dried over Na$_2$SO$_4$ and the solvent removed under reduced pressure. Chromatography on silica gel (7:3 hexanes/ethyl acetate, R$_f$ 0.20) afforded 47 (0.980 g, 2.75 mmol, 62%) as a yellow oil. $^1$H NMR (400 MHz, CDCl$_3$) δ 1.37 (3H, t, J 7.6 Hz), 2.79 (1H, dd, J 7.2, 15.2 Hz), 2.86 (1H, dd, J 7.2, 15.2 Hz), 4.07 (1H, quint, J 7.2 Hz), 4.34 (2H, q, J 7.2 Hz), 4.72 (1H, dd, J 7.8, 12.6 Hz), 4.83 (1H, dd, J 6.4, 12.4 Hz), 6.63 (1H, d, J 16 Hz), 7.11 (1H, t, J 7.6 Hz), 7.24-7.26 (2H, m), 7.27-7.36 (2H, m), 7.45 (1H, s), 7.47 (2H, d, J 8.8 Hz), 7.96 (2H, d, J 8.8 Hz). $^{13}$C NMR (400 MHz, CDCl$_3$) δ 14.55, 40.67, 40.93, 61.20, 79.50, 119.17, 126.54, 127.53, 128.45, 129.48, 130.98, 138.51, 141.60, 166.30, 168.39. MS (API-ES): m/z found 357 [M+H]$^+$ (100%), HRMS (API-ES) m/z found 357.1344 [M+H]$^+$.

Ethyl 4-(3-naphthalen-2-yl-4-nitro-butyrylamino)benzoate (48). This was prepared from corresponding amide 42 (0.995 g, 2.88 mmol) in a similar manner as described for preparation of 47. Chromatography on silica gel performed using a FlashMaster 3 purification station (75:25 hexanes/ ethyl acetate, R$_f$ 0.20) afforded 48 (0.819 g, 2.017 mmol, 70%) as a yellow oil. $^1$H NMR (400 MHz, DMSO-d$_6$) δ 1.26 (3H, t, J 7.6 Hz), 2.85-2.93 (2H, m), 4.10 (1H, quint, J 8.0 Hz), 4.23 (1H, q, J 7.2 Hz), 5.02-5.10 (2H, m), 7.45-7.48 (2H, m), 7.54 (1H, dd, J 1.6, 8.8 Hz), 7.62 (2H, d, J 8.8 Hz), 7.82-7.87 (6H, m). $^{13}$C NMR (400 MHz, CDCl$_3$) δ 14.52, 40.75, 40.79, 61.21, 79.48, 119.21, 124.97, 126.43, 126.65, 126.78, 126.87, 127.92, 128.04, 129.37, 130.94, 133.11, 133.59, 135.89, 141.68, 166.37, 168.54. MS (API-ES): m/z found 407 [M+H]$^+$ (100%), HRMS (API-ES) m/z 407.1607 [M+H]$^+$.

Methyl 2-(benzyloxy)-4-(3-(naphthalen-2-yl)-4-nitrobutanamido)benzoate (49). Benzyl bromide (0.236 g, 1.38 mmol) and K$_2$CO$_3$ (0.190 g, 1.38 mmol) were added to a stirred solution of 43 (0.400 g, 1.15 mmol) in anhydrous DMF (7 ml) under Ar. The reaction mixture was stirred at room temperature overnight and the mixture was poured in water (15 ml). The product was extracted with ethyl acetate (2×15 ml), dried over Na$_2$SO$_4$ and the solvent removed under reduced pressure. The resultant product 44 was stirred in the microwave reactor in presence of DBU (0.192 g, 1.27 mmol), and nitromethane (7 ml) in the microwave), at 100° C. for 15 min. After cooling to room temperature, the reaction mixture was poured into HCl 1M (10 ml). The product was extracted with ethyl acetate (2×15 ml), dried over Na$_2$SO$_4$ and the solvent removed under reduced pressure. Chromatography on silica gel (60:40 hexanes/ethyl acetate) afforded 49 (0.413 g, 0.83 mmol, 72%) as a yellow oil. $^1$H NMR (400 MHz, CDCl$_3$) δ 2.88 (1H, dd, J 6.8, 15.6 Hz), 2.96 (1H, dd, J 7.2, 15.2 Hz), 3.86 (3H, s), 4.26 (1H, quint, J 7.1 Hz), 4.83 (1H, dd, J 7.4, 12.6 Hz), 4.93 (1H, dd, J 6.8, 12.4 Hz), 5.10 (2H, s), 6.71 (1H, dd, J 2.0, 8.8 Hz), 7.13 (1H, bs), 7.28-7.32 (1H, m), 7.36-7.39 (3H, m), 7.47-7.52 (5H, m), 7.71 (1H, bs), 7.77-7.86 (4H, m). $^{13}$C NMR (400 MHz, CDCl$_3$) δ 40.68, 40.81, 52.15, 70.70, 79.44, 101.39, 111.15, 115.91, 124.94, 126.67, 126.79, 126.89, 127.22, 127.93, 128.05, 128.79, 128.72, 129.39, 133.11, 133.60, 135.89, 136.54, 142.68, 159.61, 166.42, 168.57. MS (API-ES): m/z found 499 [M+H]$^+$ (100%), HRMS (API-ES) m/z 499.1862 [M+H]$^+$.

Methyl 2-(benzyloxy)-4-(3-(4-chlorophenyl)-4-nitrobutanamido)benzoate (50). Benzyl bromide (0.575 g, 3.36 mmol) and K$_2$CO$_3$ (0.77 g, 5.60 mmol) were added to a stirred solution of 45 (0.9 g, 2.80 mmol) in anhydrous DMF (20 ml) under Ar. The reaction mixture was stirred at room temperature overnight and the mixture was poured in water (20 ml). The product was extracted with ethyl acetate (2×20 ml), dried over Na$_2$SO$_4$ and the solvent removed under reduced pressure. The resultant crude 46 was stirred in the microwave reactor in presence of DBU (0.468 g, 3.08 mmol), and nitromethane (10 mL in the microwave), at 100° C. for 15 min. After cooling to room temperature, the reaction mixture was poured into HCl 1M (15 ml). The product was extracted with ethyl acetate (2×20 ml), dried over Na$_2$SO$_4$ and the solvent removed under reduced pressure. Chromatography on silica gel (80:20, hexanes/ethyl acetate) afforded 50 (0.521 g, 1.10 mmol, 40%) as a white solid, mp 81-83° C. $^1$H NMR (400 MHz, CDCl$_3$) δ 2.75 (1H, dd, J 6.6, 15.4 Hz), 2.85 (1H, dd, J 7.6, 15.6 Hz), 3.87 (3H, s), 4.07 (1H, quint, J 6.8 Hz), 4.70 (1H, dd, J 7.8, 13.0 Hz), 4.83 (1H, dd, J 6.4, 12.8 Hz), 5.17 (2H, s), 6.77 (1H, dd, J 2.0, 8.4 Hz), 7.19 (3H, d, J 8.0 Hz), 7.32 (3H, d, J 8.8 Hz), 7.39 (2H, t, J 8.0 Hz), 7.51 (2H, d, J 7.2 Hz), 7.55 (1H, bs), 7.82 (1H, d, J 8.0 Hz). $^{13}$C NMR (100 MHz, CDCl$_3$) δ39.89, 40.59, 52.18, 70.79, 79.25, 104.96, 111.08, 116.14, 127.20, 128.11, 128.76, 128.92, 129.61, 133.17, 134.28, 136.56, 137.04, 142.50, 159.65, 166.36, 168.17. $v_{max}$ (pure sample)/(cm$^{-1}$) 3329, 1695, 1591, 1549, 1530, 1245, 1090. MS (API-ES): m/z 483 [M+H]$^+$ (100%), HRMS (API-ES) m/z found 483.1236 [M+H]$^+$.

Ethyl 4-(4-amino-3-phenylbutanamido)benzoate (51). Ref. *J. Org. Chem.*, 2000, 65, 8001. To a stirred solution of nitro compound 47 (0.749 g, 2.10 mmol) and NiCl$_2$.6H$_2$O (1.99 g, 8.40 mmol) in methanol (10 ml) NaBH$_4$ (0.719 g, 18.93 mmol) was added portionwise over 20 min at 0° C. After stirring for 15 min at room temperature, the solvent was removed under reduced pressure. Water (20 ml) and ethyl acetate (40 ml) were added to the solid residue. The resulting mixture was filtered through a celite bed which was washed with ethyl acetate (20 ml). After collecting the filtrate, the organic phase was separated, dried over Na$_2$SO$_4$ and the solvent removed under reduced pressure to afford amine 51 as an off white solid (0.596 g, 1.83 mmol, 87%). The amine was used in the next step without further purification.

Ethyl 4-(4-amino-3-(naphthalen-2-yl)butanamido)benzoate (52). This was obtained as a yellow solid (0.819 g, 2.178 mmol, 89%) from nitro compound 48 (0.995 g, 2.450 mmol) in a similar manner as described for preparation of 51. The product amine 52 used in the next step without further purification.

Methyl 4-(4-amino-3-(naphthalen-2-yl)butanamido)-2-(benzyloxy)benzoate (53). This was obtained as a white solid (0.023 g, 0.033 mmol, 36%) from nitro compound 49 (0.043 g, 0.091 mmol) a similar manner as described for preparation of 51. The product amine 53 was taken to the next step without further purification.

Methyl 4-(4-amino-3-(4-chlorophenyl)butanamido)-2-(benzyloxy)benzoate (54). This was obtained as yellow solid (0.349 g, 0.79 mmol, 77%) from nitro compound 50 (0.488 g, 1.033 mmol) a similar manner as described for preparation of 51. The crude amine 54 was taken to the next step without further purification.

Ethyl 4-(4-(4-methylphenylsulfonamido)-3-phenylbutanamido)benzoate (55). Potassium carbonate (0.325 g, 2.35 mmol) was added to a solution of 51 (0.128 g, 0.392 mmol) in 1,4-dioxane/H$_2$O 1:1 (5 mL) and followed by tosyl chloride (0.074 g, 0.392 mmol) at room temperature. After stirring for 2 h at room temperature, the resulting mixture was evaporated in vacuo to dryness. Water (10 ml) was added and the resulting white solid was separated by filtration and dried in vacuo. Pure 55 was obtained as an off-white solid (0.122 g, 0.254 mmol, 65%) without further purification, mp 135-137° C. $^1$H NMR (400 MHz, CD$_3$OD) 1.36 (3H, t, J 7.2 Hz), 2.39 (3H, s), 2.63 (1H, dd, J 8.6, 14.6 Hz), 2.85 (1H, dd, J 6.2, 15.0 Hz), 3.05 (1H, dd, J 7.4, 13.0 Hz), 3.12 (1H, dd, J 6.8, 11.8 Hz), 4.32 (2H, q, J 7.2 Hz), 7.17-7.19 (3H, m), 7.23-7.27 (2H, m), 7.31 (2H, d, J 8.0 Hz), 7.54 (2H, d, J 8.4 Hz), 7.65 (2H, d, J 8.4 Hz), 7.90 (2H, d, J 8.8 Hz). $^{13}$C NMR (100 MHz, CDCl$_3$) 14.57, 21.73, 40.65, 42.04, 47.77, 61.07, 119.15, 127.14, 127.75, 127.77, 129.29, 130.07, 130.94, 136.79, 140.74, 142.12, 143.97, 166.36, 170.24. $v_{max}$ (solid)/(cm$^{-1}$) 3324, 3191, 1707, 1675, 1597, 1534, 1270, 1157, 1105. MS (API-ES): m/z 481 [M+H]$^+$ (100%), HRMS (API-ES) m/z found 481.1801 [M+H]$^+$.

Ethyl 4-(4-(4-phenoxyphenylsulfonamido)-3-phenylbutanamido)benzoate (56). This was obtained as an off white solid (0.182 g, 0.326 mmol, 77%) from 51 (0.137 g, 0.420 mmol) and 4-phenoxybenzenesulfonyl chloride (0.112 g, 0.420 mmol) in a similar manner as described for preparation of 55, mp 147-149° C. $^1$H NMR (400 MHz, CD$_3$OD) δ 1.36 (3H, t, J 7.6 Hz), 2.63 (1H, dd, J 8.4, 14.8 Hz), 2.84 (1H, dd, J 7.4, 13.2 Hz), 3.09 (1H, dd, J 7.2, 12.8 Hz), 3.16 (1H, dd, J 7.2, 12.4 Hz), 4.31 (2H, q, J 6.8 Hz), 7.00 (2H, d, J 7.2 Hz), 7.06 (2H, dd, J 0.8, 8.8 Hz), 7.18-7.22 (3H, m), 7.23-7.26 (3H, m), 7.39-741 (2H, m), 7.73 (2H, d, J 8.8 Hz), 7.89 (2H, d, J 8.8 Hz). $^{13}$C NMR (100 MHz, CDCl$_3$) 14.57, 40.73, 42.06, 47.80, 61.07, 117.92, 119.15, 120.52, 125.25, 127.75, 127.80, 129.32, 129.35, 130.41, 130.95, 133.27, 140.74, 142.08, 155.23, 161.95, 166.34, 170.20. $v_{max}$ (solid)/(cm$^{-1}$) 3322, 1702, 1596, 1532, 1487, 1407, 1274, 1243, 1151, 1104, 695. MS (API-ES): m/z 559[M+H]$^+$ (100%), HRMS (API-ES) m/z found 559.1906[M+H]$^+$.

Ethyl 4-(4-(4-methylphenylsulfonamido)-3-(naphthalen-2-yl)butanamido)benzoate (57). This was obtained as an off white solid (0.058 g, 0.109 mmol) from 52 (0.138 g, 0.375 mmol) in a similar manner as described for preparation of 55. $^1$H NMR (400 MHz, CD$_3$OD) δ 1.34 (3H, t, J 7.2 Hz), 2.34 (3H, s), 2.73 (1H, dd, J 8.2, 14.6 Hz), 2.92 (1H, dd, J 6.4, 14.8 Hz), 3.17-3.28 (2H, m), 3.47-3.52 (1H, m), 4.30 (2H, q, J 7.2 Hz, CH$_2$CH$_3$), 7.19 (2H, d, J 8.0 Hz), 7.32 (1H, dd, J 1.4, 8.6 Hz), $\overline{7.40}$-7.45 (2H, m), 7.51 (2H, d, J 8.4 Hz), 7.59 (2H, d, J 8.8 Hz), 7.60 (1H, s), 7.73-7.79 (3H, m), 7.90 (2H, d, J 9.2 Hz). $\nu_{max}$ (solid)/(cm$^{-1}$) 2958, 1706, 1596, 1531, 1273, 1171, 1152, 1105, 1020. MS (API-ES): m/z 531 [M+H]$^+$ (100%), HRMS (API-ES) m/z found 531.1962[M+H]$^+$.

Ethyl 4-(3-(naphthalen-2-yl)-4-(4-phenoxyphenylsulfonamido)butanamido)benzoate (58). The compound was obtained as a white solid in (0.100 g, 0.164 mmol, 73%) from 52 in a similar manner as described for preparation of 55, mp 141-143° C. $^1$H NMR (400 MHz, CD$_3$OD) δ 1.34 (3H, t, J 7.2 Hz), 2.75 (1H, dd, J 8.4, 14.8 Hz), 2.92 (1H, dd, J 6.6, 15.0 Hz), 3.25-3.29 (2H, m), 3.34-3.53 (1H, m) 4.30 (2H, q, J 7.2 Hz), 6.61 (2H, d, J 9.2 Hz), 7.05 (2H, dd, J 1.2, 8.8 Hz), 7.20-7.23 (1H, m), 7.34 (1H, dd, J 1.4, 8.6 Hz), 7.40-7.45 (4H, m), 7.54 (2H, d, J 8.8 Hz), 6.64 (1H, bs), 7.67 (2H, d, J 8.8 Hz), 7.75-7.90 (3H, m), 7.87 (2H, d, J 9.2 Hz). $^{13}$C NMR (100 MHz, CDCl$_3$) 14.55, 40.68, 42.12, 47.84, 61.05, 117.89, 119.19, 120.51, 125.22, 125.67, 126.21, 126.35, 126.53, 126.73, 127.85, 127.96, 129.09, 129.83, 130.39, 130.90, 132.85, 133.27, 133.61, 138.16, 142.13, 155.24, 161.90, 166.34, 170.26. $\nu_{max}$ (solid)/(cm$^{-1}$) 1707, 1596, 1531, 1486, 1275, 1243, 1151, 1098. MS (API-ES): m/z 609 [M+H]$^+$ (100%), HRMS (API-ES) m/z found 609.2058 [M+H]$^+$.

4-(4-(4-methylphenylsulfonamido)-3-phenylbutanamido)benzoic acid (59). A solution of the ester 55 (0.106 g, 0.220 mmol) in methanol (3 ml) and THF (3 ml) was stirred in presence of NaOH (aq, 1M, 1 ml) at room temperature overnight. The solvent was removed under reduced pressure. HCl (aq, 1M, 1.5 ml) was added and the white precipitate was filtered, washed with water (5 ml) and dried under vacuum. Pure 59 was obtained as a white solid (0.085 g, 0.188 mmol, 85%) without further purification, mp 225-227° C. $^1$H NMR (400 MHz, CD$_3$OD) δ2.39 (3H, s), 2.62 (1H, dd, J 8.4, 14.8 Hz), 2.35 (1H, dd, J 6.6, 14.6 Hz), 3.05 (1H, dd, J 8.0, 13.0 Hz), 3.12 (1H, dd, J 7.2, 12.8 Hz), 7.16-7.19 (3H, m), 7.24-7.27 (2H, m), 7.30 (2H, d, J 7.6 Hz), 7.53 (2H, d, J 8.4 Hz), 7.65 (2H, d, J 8.4 Hz), 7.91 (2H, d, J 9.2 Hz). $^{13}$C NMR (100 MHz, DMSO-d$_3$) δ 21.61, 40.65, 42.32, 48.33, 118.95, 125.61, 127.18), 127.26, 128.38, 128.96, 130.02, 130.98, 138.09, 142.47, 143.22, 143.72, 167.55, 170.64. $\nu_{max}$ (solid)/(cm$^{-1}$) 3316, 3277), 1668, 1595, 1531, 1408, 1317, 1254, 1152. MS (API-ES): m/z 451[M–H]$^-$ (100%), HRMS (API-ES) m/z found 451.1334 [M–H]$^-$.

4-(4-(4-phenoxyphenylsulfonamido)-3-phenylbutanamido)benzoic acid (60). This was obtained as a white solid (0.120 g, 0.226 mmol, 83%) from the ester 56 (0.152, 0.272 mmol) in a similar manner as described for preparation of 59, mp 187-189° C. $^1$H NMR (400 MHz, CD$_3$OD) δ 2.63 (1H, dd, J 8.8, 14.8 Hz), 2.84 (1H, dd, J 6.6, 14.6 Hz), 3.09 (1H, dd, J 7.8, 13.0 Hz), 3.16 (1H, dd, J 6.8, 12.8 Hz), 7.00 (2H, d, J 9.2 Hz), 7.06 (2H, dd, J 1.2, 8.4 Hz), 7.16-7.28 (6H, m), 7.39-743 (2H, m), 7.53 (2H, d, J 8.4 Hz), 7.73 (2H, d, J 8.4 Hz), 7.90 (2H, d, J 8.4 Hz). $^{13}$C NMR (100 MHz, CD$_3$OD) 40.86, 42.63, 47.85, 117.47, 119.00, 120.09, 124.77, 125.74, 126.70, 127.66, 128.46, 129.12, 130.10, 130.49, 134.36, 141.39, 142.91, 155.62, 161.59, 168.23, 171.43. $\nu_{max}$ (solid)/(cm$^{-1}$) 3060, 1681, 1596, 1585, 1487, 1318, 1294, 1251, 11511. MS (API-ES): m/z found 529 [M–H]$^-$ (100%), HRMS (API-ES) m/z found 529.1433 [M–H]$^-$.

4-(3-(naphthalen-2-yl)-4-(4-phenoxyphenylsulfonamido)butanamido)benzoic acid (61). This was obtained as a white solid (0.052 g, 0.090 mmol, 70%) from 57 (0.079 g, 0.129 mmol) in a similar manner as described for preparation of 59, mp 183-184° C. $^1$H NMR (400 MHz, CD$_3$OD) δ 2.65 (1H, dd, J 8.4, 14.8 Hz), 2.82 (1H, dd, J 6.8, 14.8 Hz), 3.11-3.20 (2H, m), 3.40-3.44 (1H, m), 6.81 (2H, d, J 8.4 Hz), 6.94-6.96 (2H, m), 7.10-7.14 (1H, m), 7.25 (1H, dd, J 1.6, 8.8 Hz), 7.29-7.35 (4H, m), 7.41 (2H, d, J 8.8 Hz), 7.54 (1H, bs), 7.58 (2H, d, J 8.8 Hz), 7.65-7.68 (3H, m), 7.78 (2H, d, J 8.4 Hz). $^{13}$C NMR (100 MHz, CD$_3$OD) 40.82, 42.70, 47.90, 117.34, 119.00, 120.115, 124.76, 125.53, 125.66, 125.91, 126.54, 127.39, 127.53, 128.12, 129.06, 130.09, 130.51, 132.92, 133.74, 134.38, 138.80, 142.80, 155.55, 161.50, 171.36. $\nu_{max}$ (solid)/(cm$^{-1}$) 3061, 1683, 1599, 1584, 1514, 1486, 1304, 1240, 1147. MS (API-ES): m/z found 579 [M–H]$^-$ (100%), HRMS (API-ES) m/z found 579.1585 [M–H]$^-$.

4-(4-(4-methylphenylsulfonamido)-3-(naphthalen-2-yl)butanamido)benzoic acid (62). This was obtained as a white solid (0.021 g, 0.042 mmol, 65%) from 58 (0.034 g, 0.064 mmol) in a similar manner as described for preparation of 59, mp. $^1$H NMR (400 MHz, CD$_3$OD) δ 2.34 (3H, s), 2.73 (1H, dd, J 8.2, 14.6 Hz), 2.91 (1H, dd, J 6.4, 14.8 Hz), 3.20 (1H, dd, J 7.6, 12.8 Hz), 3.25-3.29 (1H, m), 3.47-3.53 (1H, m), 7.19 (2H, d, J 8.0 Hz), 7.32 (1H, dd, J 1.6, 8.8 Hz), 7.39-7.45 (2H, m), 7.51 (2H, d, J 9.2 Hz), 7.59 (2H, d, J 8.8 Hz), 7.60 (1H, s), 7.73-7.79 (3H, m), 7.88 (2H, d, J 9.2 Hz). $^{13}$C NMR (100 MHz, DMSO-d$_6$) 21.60, 42.52, 48.31, 118.92, 125.73, 126.20, 126.65, 126.88, 126.95, 127.13, 128.09, 128.20, 128.41, 130.18, 130.95, 132.73, 133.62, 138.16, 140.03, 143.15, 143.67, 167.57, 170.61. $\nu_{max}$ (solid)/(cm$^{-1}$) 1680, 1595, 1530, 1408, 1305, 1252, 1152. MS (API-ES): m/z 5019 [M–H]$^-$ (100%), HRMS (API-ES) m/z found 501.14831 [M–H]$^-$.

Methyl 2-(benzyloxy)-4-(3-(naphthalen-2-yl)-4-(4-phenoxyphenylsulfonamido)butanamido)benzoate (63). This was obtained as an off white solid (0.023 g, 0.032 mmol, 36%) from amine 53 (0.043 g, 0.091 mmol) in a similar manner as described for preparation of 55. The crude ester was used in the next step without further purification.

Methyl 2-hydroxy-4-(3-(naphthalen-2-yl)-4-(4-phenoxyphenylsulfonamido)butanamido)benzoate (64). A solution of 63 (0.023 g, 0.032 mmol) in methanol (1 ml) was stirred in presence of ammonium formate (0.089 g) and 10% Pd/C (0.023 g), under H$_2$, at room temperature for 2 days. The solution was then filtered through a celite bed and the solvent removed under reduced pressure to afford ester 64 (0.014 g, 0.0230 mmol, 70%) as yellow solid, which was used in the next step without further purification.

2-hydroxy-4-(3-(naphthalen-2-yl)-4-(4-phenoxyphenylsulfonamido)butanamido)benzoic acid (65). This was obtained as an off-white solid (0.0063 g, 0.011 mmol, 50%) ester 64 (0.013 g, 0.021 mmol) in a similar manner as described for preparation of 59. mp 153-155° C. $^1$H NMR (400 MHz, CD$_3$OD) δ 2.63 (1H, dd, J 14.6, 8.2 Hz), 2.86 (1H, dd, J 15.0, 6.6 Hz), 3.13 (1H, dd, J 13.2, 7.6 Hz), 3.16-3.20 (1H, m), 3.37-3.48 (1H, m), 6.77-6.83 (3H, m), 6.94-6.96 (2H, m), 7.08-7.14 (2H, m), 7.24 (1H, dd, J 8.4, 1.66 Hz), 7.29-7.35 (4H, m), 7.53 (1H, bs), 7.57-7.60 (1H, m), 7.66-7.69 (3H, m), 9.80 (1H, bs). MS (API-ES): m/z 595 [M–H]$^-$ (100%), HRMS (API-ES) m/z found 595.1537 [M–H]$^-$.

Methyl 2-(benzyloxy)-4-(3-(4-chlorophenyl)-4-(4-phenoxyphenylsulfonamido)butanamido)benzoate (66). This was obtained as an off-white solid (0.205 g, 0.304 mmol, 78%) from the amine 54 (0.137 g, 0.391 mmol) in a similar manner as described for preparation of 55. The crude product sulfonamide was taken to the next step without further purification.

Methyl 4-(3-(4-chlorophenyl)-4-(4-phenoxyphenylsulfonamido)butanamido)-2-hydroxybenzoate (67). This was obtained as an off-white solid (0.106 g, 0.181 mmol, 67%) from benzyl ether 66 (0.183 g, 0.27 mmol) in a similar manner as described for preparation of 64. The crude ester 67 was taken to the next step without further purification.

4-(3-(4-Chlorophenyl)-4-(4-phenoxyphenylsulfonamido)butanamido)-2-hydroxybenzoic acid (68). This was obtained as an off-white solid (0.047 g, 0.082 mmol, 67%) from the ester 67 (0.076 g, 0.130 mmol) in a similar manner as described for preparation of 59. The crude acid 68 was taken to the next step without further purification. $^1$H NMR (400 MHz, CDCl$_3$) δ 2.59 (1H, dd, J 14.8, 8.8 Hz), 2.80 (1H, dd, J 14.8, 6.8 Hz), 3.12 (2H, m), 6.90 (1H, dd, J 10.4, 2.0 Hz), 6.99 (2H, d, J 9.2 Hz), 7.07 (2H, d, J 9.2 Hz), 7.16-7.27 (6H, m), 7.40-7.44 (2H, m), 7.69-7.74 (3H, m). MS (API-ES): m/z 579 [M–H]$^-$ (100%), HRMS (API-ES) m/z found 579.1000 [M–H]$^-$.

Ethyl 4-(3-(naphthalen-2-yl)propanamido)benzoate (69). Ref. *J. of Org. Chem.*, 2000, 65, 8001. To a stirred solution of amide 42 (0.086 g, 0.249 mmol) and NiCl$_2$ 6H$_2$O (0.118 g, 0.498 mmol, 2 eq) in methanol (8 ml) and THF (4 ml) NaBH$_4$ (0.028 g, 0.749 mmol, 4 eq) was added portionwise over 20 min at 0° C. After stirring for 1 h at room temperature, the solvent was distilled off under reduced pressure. Water (10 ml) and ethyl acetate (10 ml) was added. The resulting mixture was filtered through a celite bed which was washed with ethyl acetate (20 ml). After collecting the filtrate, the organic phase was separated, dried over Na$_2$SO$_4$ and the solvent was distilled off under reduced pressure to give the pure product 69 as a white solid (0.066 g, 0.190 mmol, 79%), mp 119-121° C. $^1$H NMR (400 MHz, CDCl$_3$) δ 1.38 (3H, t, J 7.2 Hz, CH$_2$CH$_3$) 2.75 (2H, t, J 7.2 Hz, CH$_2$CO), 3.23 (2H, t, J 7.2 Hz, CH$_2$—Ar), 4.35 (2H, q, J 7.2 Hz, CH$_2$CH$_3$), 7.12 (1H, bs, N—H), 7.37 (1H, dd, J 1.6, 8.4 Hz, CH, Ar), 7.42-7.50 (4H, m, 4×CH, Ar), 7.69 (1H, bs, CH, Ar), 7.76-7.82 (3H, m, 3×CH, Ar), 7.97 (2H, d, J 9.2 Hz, 2×CH, Ar). MS (API-ES): m/z 348 [M+H]$^+$ (100%), HRMS (API-ES) m/z found 348.1602 [M+H]$^+$.

Ethyl 4-(3-phenylpropanamido)benzoate (70). This was as obtained from 41 in a similar manner as described for preparation of 69. The crude product 70 was taken to the next step without further purification, mp 109-111° C. $^1$H NMR (400 MHz, CDCl$_3$) δ (3H, t, J Hz, CH$_2$CH$_3$), (2H, t, J Hz, CH$_2$CO), (2H, t, J Hz, CH$_2$—Ar), (2H, q, J 7 Hz, CH$_2$CH$_3$), (1H, bs, N—H), 7.37 (1H, dd, J 1.6, 8.4 Hz, CH, Ar), 7.42-7.50 (4H, m, 4×CH, Ar), 7.69 (1H, bs, CH, Ar), 7.76-7.82 (3H, m, 3×CH, Ar), 7.97 (2H, d, J 9.2 Hz, 2×CH, Ar). MS (API-ES): m/z 298 [M–H]$^-$ (100%), HRMS (API-ES) m/z found 298.1444 [M–H]$^-$.

4-(3-(Naphthalen-2-yl)propanamido)benzoic acid (71). The pure compound was obtained as a white solid in 73% yield from 69 in a similar manner as described for preparation of 59, mp 255-257° C. $^1$H NMR (400 MHz, CD$_3$OD) δ 2.69 (2H, t, J 7.2 Hz, CH$_2$CO), 3.07 (2H, t, J 7.6 Hz, CH$_2$—Ar), 7.28-7.35 (3H, m, 3×CH, Ar), 7.53 (2H, d, J 8.4 Hz, 2×CH, Ar), 7.61 (1H, bs, CH, Ar), 7.66-7.71 (3H, m, 3×CH, Ar), 7.84 (2H, d, J 9.2 Hz, 2×CH, Ar). $^{13}$C NMR (400 MHz, DMSO-d$_6$) δ 31.53 (s) (CH$_2$CO), 38.60 (s) (CH$_2$Ar), 118.95 (s) (2×CH, Ar), 125.99 (s) (CH, Ar), 126.71 (s) (CH, Ar), 126.80 (s) (CH, Ar), 127.91 (s) (CH, Ar), 127.98 (s) (CH, Ar), 128.15 (s) (CH, Ar), 128.46 (s) (CH, Ar), 131.03 (s) (2×CH, Ar), 132.34 (s) (C, Ar), 133.82 (s) (C, Ar), 139.41 (s) (C, Ar), 143.85 (s) (C, Ar), 167.65 (s) (C=O), 171.62 (s) (C=O). ν$_{max}$ (pure sample)/(cm$^{-1}$) 3298 (st) (OH), 1701 (md) (C=O), 1674 (st) (C=O) 1607 (md), 1595 (md), 1530 (st), 1429, 1405, 1293.

MS (API-ES): m/z 318 [M–H]$^-$ (100%), HRMS (API-ES) m/z found 318.11327 [M–H]$^-$.

4-(3-Phenylpropanamido)benzoic acid (72). This was obtained pure as a white solid in 76% yield from 69 in a similar manner as described for preparation of 59. $^1$H NMR (400 MHz, CD$_3$OD) δ 2.68 (2H, t, J 7.6 Hz), 2.99 (2H, t, J 8.4 Hz), 7.16-7.19 (1H, m), 7.23-7.26 (4H, m), 7.63 (2H, d, J 8.4 Hz), 7.94 (2H, d, J 8.4 Hz). ν$_{max}$ (pure sample)/(cm$^{-1}$) 3310, 1666, 1607 (md), 1593, 1522, 1428, 1404, 1318. MS (API-ES): m/z 268 [M–H]$^-$ (100%), HRMS (API-ES) m/z 268.0979 [M–H]$^-$.

4-(3-Phenylpropanamido)-2-hydroxybenzoic acid (73). A solution of the chlorocinnamide 45 (0.118 g, 0.367 mmol) in methanol (6 ml) and THF (6 ml) was stirred in presence of ammonium formate (0.231 g) and 10% Pd/C (0.010 g) at room temperature under Ar. After stirring overnight, the solution was filtered through a celite bed and the solvent removed under reduced pressure to afford an off-white solid. The solution of the crude compound in methanol (10 ml) and THF (4 ml) was stirred in presence of NaOH (aq, 1 M, 3 ml) at 100° C. for 2 h. After cooling to room temperature, the solvent was removed under reduced pressure, and the resulting aqueous solution acidified with HCl (aq, 1 M) until pH 1. The precipitate was collected by filtration, washed with H$_2$O (3 ml) and dried in vacuo. Pure 22 was obtained as an off-white solid without further purification (0.045 g, 0.165 mmol, 45%), mp 165-167° C. $^1$H NMR (400 MHz, DMSO-d$_6$) δ 2.61 (2H, t, J 8.0 Hz), 2.88 (2H, t, J 8.0 Hz), 7.00 (1H, dd, J 8.8, 2.4 Hz), 7.21-7.33 (5H, m), 7.67 (2H, d, J 8.8 Hz), MS (API-ES): m/z 284 [M–H]$^-$ (100%), HRMS (API-ES) m/z found 284.097194 [M–H]$^-$.

The following compounds were prepared according to Scheme 6.

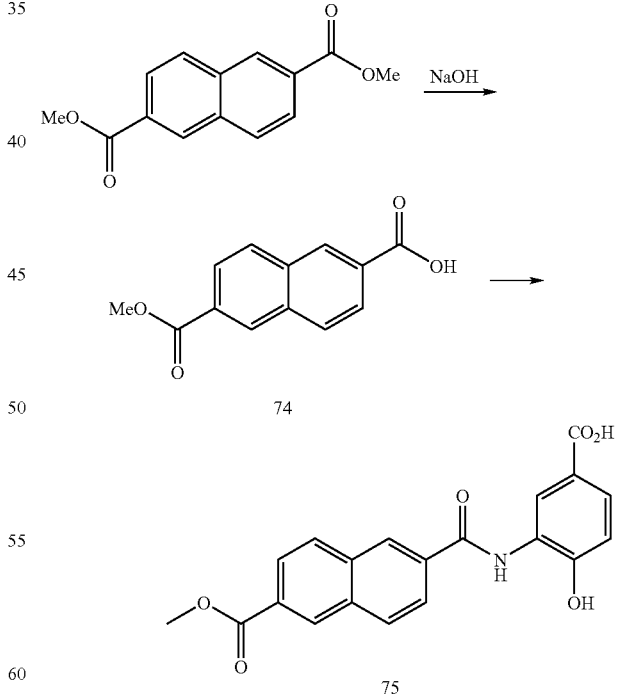

6-(Methoxycarbonyl)-2-naphthoic acid (74). A solution of KOH (0.459 g, 8.18 mmol) in methanol (1.5 ml) was added to a suspension of dimethyl 2,6-naphthlene dicarboxylate (2.0 g, 8.18 mmol) in dioxane (20 ml). The reaction mixture was stirred at 80° C. for 4 h, cooled to room temperature and a solid residue was rinsed with diethyl ether (10 ml). The solid was dissolved in water and treated with HCl (aq, 2M) to pH 3. The precipitate was filtered, washed with water, dried under vacuum to provide pure 74 as a white solid (1.55 g, 6.72 mmol, 82%). $^1$H NMR (400 MHz, DMSO-d$_6$) δ 3.91 (3H, s), 8.02 (2H, dd, J 8.4 Hz), 8.22 (2H, dd, J 8.4 Hz), 8.66 (2H, dd, J 10.4 Hz).

4-hydroxy-3-(6-(methoxycarbonyl)-2-naphthamido)benzoic acid (75). A solution of 3-amino-4-hydroxybenzoic acid (0.142 g, 0.927 mmol) and the acyl chloride prepared from acid 74 (in 84% yield) (0.259 g, 1.019 mmol) in DCM (5 ml) and pyridine (6 ml) was stirred at room temperature for under at for 24 h. The solvent was removed under reduced pressure. HCl (aq, 4 M, 6 ml) was added and the precipitate was filtered, washed with water (10 ml) and dried under vacuum. Trituration with methanol (15 ml) and acetone (10 ml) afforded 75 as an off-white solid (0.084 g, 0.230 mml, 25%). $^1$H NMR (400 MHz, DMSO-d$_6$) δ 3.92 (3H, s), 7.00 (1H, d, J 8.4 Hz), 7.67 (1H, d, J 8.8 Hz), 8.04-8.10 (2H, m), 8.16-8.27 (2H, m), 8.33 (1H, s), 8.70-8.66 (2H, m), 9.80 (1H, s), 10.55 (1H, bs). $^{13}$C NMR (100 MHz, DMSO-d$_6$) δ 53.09, 116.18, 122.59, 125.94, 126.45, 126.26, 126.80, 128.45, 128.48, 129.19, 130.35, 130.40, 130.93, 134.13, 134.66, 134.94, 154.61, 165.85, 166.84, 167.73. $v_{max}$ (solid)/(cm$^{-1}$) 3059, 1716, 1666, 1592, 1541, 1283, 1247, 1132, 759.

Example 12

Effects of Compounds on Activation of STATs, Shc, and Erks

The following experiments and results are described and shown in Siddiquee, K. et al., PNAS USA, 2007, May, 104 (18):7391-7396, Epub 2007 Apr. 26, which is incorporated by reference herein in its entirety. Nuclear extracts containing activated Stat1, Stat3, and Stat5 proteins were pre-incubated with increasing concentrations of compounds for 30 minutes at room temperature prior to incubation with radiolabeled hSIE probe that binds Stat1 and Stat3 or MGFe probe that binds Stat1 and Stat5 and subjecting to EMSA analysis. Cell lysates containing activated Stat3 were pre-incubated with NSC 74859 in the presence and absence of increasing amount of cell lysates containing inactive Stat3 protein (monomer) prior to incubation with radiolabeled hSIE probe and subjecting to EMSA analysis. Nuclear extract preparations from v-Src-transformed NIH3T3/v-Src fibroblasts treated for the times indicated in FIG. 2 of Siddiquee, K et al. (2007) or human breast cancer MDA-MB-231 and MDA-MB-468 treated for 48 hours with 100 μM NSC 74859 were incubated with radiolabeled hSIE probe and subjected to EMSA analysis. SDS-PAGE and Western blot analysis of whole-cell lysates from NIH3T3/v-Src fibroblasts treated with or without NSC 74859 (100 μM, 48 hours) for pTyr705Stat3 or Stat3. SDS-PAGE and Western blot analysis of cell lysates prepared from NIH3T3/v-Src or EGF-stimulated NIH3T3/hEGFR was carried out using antibodies against pShc, pErk1/2 (pp42/pp44), Erk, or β-actin, or antiphosphotyrosine antibody, clone 4G10. Controls included nuclear extracts untreated with compounds, and nuclear extracts or lysates prepared from untreated cells.

Virtual high throughput screening relied upon computational modeling of the native pTyr peptide sequence (APY*LKT; SEQ ID NO:1) from one Stat3 monomer bound within the SH2 domain of the second Stat3 monomer, as observed for the Stat3 dimer protein bound to DNA (Becker, S. et al. Nature, 1998, 394:145-151). For the docking studies, DNA was removed and only one of the two monomers was employed. The approach was used to evaluate the NCI Diversity Set and Plated Set chemical libraries. Three-dimensional structures for compounds from the NCI Diversity Set and NCI Plated Set were downloaded from NCI's DTP website (presented in Siddiquee, K. et al. (2007)), processed with LigPrep (36; available from Schrödinger, L.L.C.) to produce 2,392 3D structures for the Diversity Set and 150,829 3D structures for the Plated Set. These structures were docked using GLIDE 2.7 in SP (Standard Precision) mode into the pTyr peptide binding site within the SH2 domain of the monomer employed. The best scoring compounds (74 compounds selected via visual inspection from the top 100 compounds with the best score from the Diversity Set and the top 200 compounds from the Plated Set that then were filtered by MW (<700) and computed logs (>−10) to yield 122 compounds) were selected for evaluation in in vitro Stat3 DNA-binding assay. Nuclear extracts containing activated STATs were incubated for 30 minutes with or without increasing concentrations of compounds prior to incubation with radiolabeled hSIE probe that binds to Stat1 and Stat3 or MGFe probe that binds Stat1 and Stat5 and subjected to EMSA analysis. Results for a representative number of compounds show differential inhibition of DNA binding activity of Stat3 following preincubation of nuclear extracts with compounds (Table 4) (data not shown for the remainder of the 194 compounds evaluated in the DNA-binding assay). Potent inhibition of Stat3 DNA-binding activity by the NCI Plated Set compounds, NSC 42067, NSC 59263, NSC 74859, and NSC 75912, was observed. Other notable potent inhibitors of Stat3 DNA-binding activity from the Plated Set include NSC 11421, NSC 91529, and NSC 263435 (Table 4). A few compounds with weak inhibitory activity were also identified from the NCI Diversity Set (data not shown). To determine selectivity against other STAT family members, selected active compounds were evaluated in in vitro DNA-binding assay of the three STAT proteins, Stat1, Stat3, and Stat5, in nuclear extracts prepared from EGF-stimulated NIH3T3/hEGFR fibroblasts that activates all three STATs. EMSA analyses of the DNA-binding activities of STAT proteins show that of the representative compounds, NSC 74859 preferentially inhibits Stat3 over Stat1 or Stat5 DNA-binding activity (Table 4), while NSC 42067 and NSC 59263 preferentially inhibit Stat3 and Stat5 over that of Stat1 (Table 4). In recognition of the role of constitutive Stat5 in hematological and other cancers, the inhibition of Stat5 DNA-binding activity could have clinical implications. Where Stat1 DNA-binding activity was inhibited, as with NSC 42067 and NSC 59263, it occurred at concentrations 3-4 times higher than concentrations that inhibited Stat3 or Stat5 (Table 4). In contrast, NSC 75912 preferentially inhibits Stat1 over Stat3 or Stat5 (Table 4). For the remaining compounds, no appreciable pattern of specificity of inhibition of the STAT family members was observed (Table 4 and data not shown). These studies identify NSC 42067, NSC 59263, and NSC 74859 from the NCI chemical libraries as binders within the SH2 domain of Stat3 and which potently inhibit Stat3 DNA-binding activity. The best of these compounds is NSC 74859 (re-synthesized as a pure sample named BG2065p or S3I-201).

TABLE 4

IC$_{50}$ values for the inhibition of STATs DNA-binding activity in vitro

| NSC# | IC$_{50}$ (μM) | | | |
|---|---|---|---|---|
| | Stat3:3 | Stat1:3 | Stat1:1 | Stat5:5 |
| 11421 | 80 | 145 | 105 | 221 |
| 24056 | 245 | 256 | 267 | 235 |
| 26685 | 85 | 68 | 95 | 125 |
| 42067 | 65 | 86 | 197 | 88 |
| 51926 | 292 | 300 | 300 | >300 |
| 59263 | 72 | 89 | 226 | 69 |
| 71906 | 295 | 258 | 225 | 285 |
| 74859 | 86 | 160 | >300 | 166 |
| 75912 | 160 | 104 | 72 | >300 |
| 75914 | 276 | 263 | 113 | >300 |
| 87849 | >300 | >300 | >300 | >300 |

TABLE 4-continued

IC$_{50}$ values for the inhibition of STATs DNA-binding activity in vitro

| NSC# | IC$_{50}$ (μM) | | | |
|---|---|---|---|---|
| | Stat3:3 | Stat1:3 | Stat1:1 | Stat5:5 |
| 90438 | >300 | >300 | >300 | >300 |
| 91529 | 95 | 85 | 155 | 85 |
| 101595 | 275 | >300 | >300 | 288 |
| 117907 | 202 | 292 | >300 | >300 |
| 205965 | 225 | 256 | 253 | 255 |
| 216360 | 220 | 290 | >300 | >300 |
| 263435 | 25 | 40 | 50 | 25 |
| 645885 | 245 | 250 | 205 | 250 |
| 647608 | 295 | >300 | >300 | >300 |

Example 13

Inhibition of STAT3 Dimerization

Table 5 shows half maximal inhibitory concentration (IC$_{50}$) for inhibition of STAT3 dimerization, as measured by the EMSA asay (Yu, C. L. et al. *Science*, 1995, 269:81-83; Garcia, R. et al. *Oncogene*, 2001, 20:2499-2513; Turkson, J. et al. *Mol. Cell. Biol.*, 1998, 18:2545-2552).

TABLE 5

Inhibition of STAT3 dimerization

| Compound # | Compound Identifier | Figure | IC$_{50}$ for the inhibition of STAT3 dimerization |
|---|---|---|---|
| 1 | NSC-74859 | 7 | <500 μM |
| 2 | BG2066 | 28 | >500 μM |
| 6 | BG3006A | 31 | >500 μM |
| 7 | BG3006B | 32 | >500 μM |
| 8 | BG3006D | 33 | >500 μM |
| 11 | BG2069-1 | 23 | >500 μM |
| 15 | BG2074 | 29 | >500 μM |
| 19 | BG3004 | 30 | >500 μM |
| 20 | BG3009 | 34 | >500 μM |
| 21 | HL2-006-1 | 13 | >500 μM |
| 22 | HL2-006-2 | 14 | >500 μM |
| 23 | HL2-006-3 | 15 | >500 μM |
| 24 | HL2-006-4 | 16 | <500 μM |
| 25 | HL2-006-5 | 17 | <500 μM |
| 27 | HL2-011-2 | 19 | >500 μM |
| 28 | HL2-011-5 | 22 | >500 μM |
| 29 | HL2-011-6 | 24 | >500 μM |
| 30 | HL2-011-6 | 25 | >500 μM |
| 31 | HL2-005 | 26 | >500 μM |
| 32 | HL2-003 | 27 | >500 μM |
| 36 | RPM381 | 35 | <500 μM |
| 38 | RPM384 | 35 | <500 μM |
| 39 | RPM385 | 35 | <500 μM |
| 55 | RPM405 | 36 | >500 μM |
| 59 | RPM411 | 36 | >500 μM |
| 37 | RPM407 | 37 | >500 μM |
| 40 | RPM412 | 37 | >500 μM |
| 56 | RPM408 | 38 | >500 μM |
| 60 | RPM410 | 38 | >500 μM |
| 57 | RPM415 | 39 | >500 μM |
| 61 | RPM416 | 39 | >500 μM |
| 58 | RPM418 | 40 | >500 μM |
| 62 | RPM418-A | 40 | >500 μM |
| 65 | RPM427 | 41 | >500 μM |
| 45 | RPM431 | 42 | >500 μM |
| 73 | RPM431 | 43 | >500 μM |
| 70 | RPM444 | 44 | >500 μM |
| 72 | RPM448 | 44 | >500 μM |
| 69 | RPM445 | 45 | >500 μM |
| 71 | RPM447 | 45 | >500 μM |
| 68 | RPM452 | 46 | >500 μM |
| 75 | RPM202 | 47 | <500 μM |

All patents, patent applications, provisional applications, and publications referred to or cited herein, supra or infra, are incorporated by reference in their entirety, including all figures and tables, to the extent they are not inconsistent with the explicit teachings of this specification.

We claim:

1. A method of treating a subject that has a proliferation disorder, comprising administering an effective amount of an isolated compound to a subject, wherein the isolated compound is at least one compound selected from

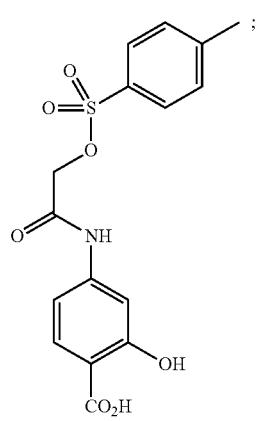

NSC-74859

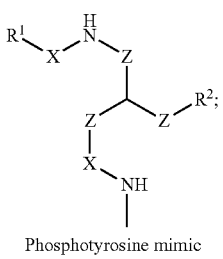

Formula C

Phosphotyrosine mimic

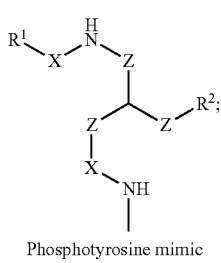

Formula D

Phosphotyrosine mimic

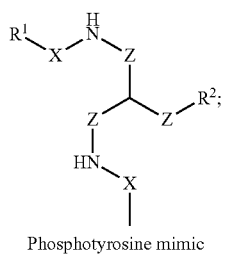

Formula E

Phosphotyrosine mimic

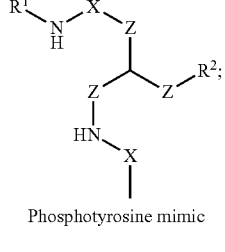

Formula F

Phosphotyrosine mimic wherein for the compound of formula C, formula D, formula E, or formula F:
$R^1$ is an aliphatic or aromatic group;
$R^2$ is an aliphatic or aromatic group;
each X is independently CO, $SO_2$, CONH, or alkyl; and
Z is alkyl; and the phosphotyrosine mimic is $CO_2H$, $SO_3H$, $PO_3H$, $NO_2$, $CH_2CO_2H$, or $CF_2CO_2H$ or a pharmaceutically acceptable salt or analog of any of the foregoing.

2. The method of claim 1, wherein the proliferation disorder is cancer.

3. The method of claim 2, wherein the compound is administered locally at the site of a tumor.

4. The method of claim 1, wherein the proliferation disorder is cancer, and wherein the subject is suffering from a tumor and the compound inhibits growth of the tumor.

5. The method of claim 1, wherein the proliferation disorder is a non-malignant disease characterized by aberrant Stat3 activation of cells.

6. The method of claim 1, wherein the compound is administered locally at the site of the proliferation disorder.

7. The method of claim 1, wherein the route of administration is selected from the group consisting of intravenous, intramuscular, oral, and intra-nasal.

8. The method of claim 1, wherein the subject is human.

9. The method of claim 1, wherein the subject is a non-human mammal.

10. The method of claim 1, further comprising identifying the subject as one suffering from the proliferation disorder.

11. The method of claim 1, wherein the subject is suffering from a tumor and wherein said administering comprises administering at the site of the tumor the compound:

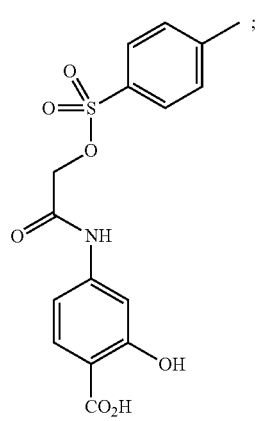
NSC-74859
;

or a pharmaceutically acceptable salt or analog thereof.

12. The method according to claim 1, wherein for the compound of any of formula C, formula D, formula E, or formula F, the $R_1$ group is alkyl, alkenyl, cycloalkyl, heterocycloalkyl, cylcoalkenyl, heterocycloalkenyl, acyl, or aryl, any of which may be optionally substituted.

13. The method according to claim 1, wherein for the compound of any of formula C, formula D, formula E, or formula F, the $R_2$ group is alkyl, alkenyl, cycloalkyl, heterocycloalkyl, cylcoalkenyl, heterocycloalkenyl, acyl, or aryl, any of which may be optionally substituted.

14. The method according to claim 1, wherein for the compound of any of formula C, formula D, formula E, or formula F, the $R_1$ group is aryl, substituted aryl, heteroaryl, or alkyl.

15. The method according to claim 1, wherein for the compound of any of formula C, formula D, formula E, or formula F, the $R_2$ group is aryl, substituted aryl, heteroaryl, or alkyl.

16. The method of claim 1, wherein the compound is

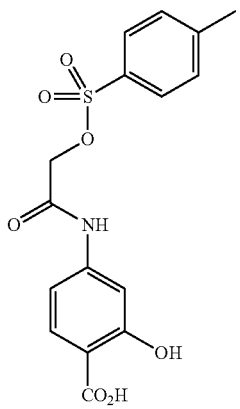
NSC-74859 or a pharmaceutically acceptable salt or analog thereof.

* * * * *

UNITED STATES PATENT AND TRADEMARK OFFICE
CERTIFICATE OF CORRECTION

PATENT NO.         : 7,960,434 B2
APPLICATION NO.    : 11/805217
DATED              : June 14, 2011
INVENTOR(S)        : James Turkson et al.

It is certified that error appears in the above-identified patent and that said Letters Patent is hereby corrected as shown below:

Column 14
Line 1, "5-decenyl, decenyl," should read --5-decenyl, 6-decenyl,--.

Column 45
Line 53, "(1000.6 MHz," should read --(100.6 MHz,--.

Column 47
Line 1, "Hydroxy-4-" should read --2-Hydroxy-4- --.

Column 53
Lines 59-60, "C(CH$_3$)," should read --C(CH$_3$)$_3$),--.

Column 55
Line 53 (compound #59), "R$_2$ = CO$_2$Et," should read --R$_2$ = CO$_2$H,--.

Column 70
Line 32 (Formula D),

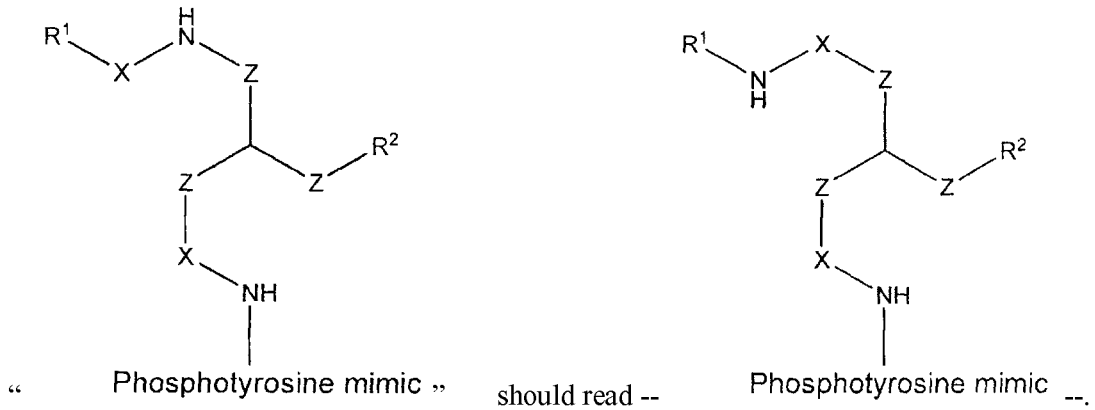

Signed and Sealed this
Eleventh Day of October, 2011

David J. Kappos
*Director of the United States Patent and Trademark Office*

UNITED STATES PATENT AND TRADEMARK OFFICE
CERTIFICATE OF CORRECTION

PATENT NO. : 7,960,434 B2
APPLICATION NO. : 11/805217
DATED : June 14, 2011
INVENTOR(S) : James Turkson et al.

It is certified that error appears in the above-identified patent and that said Letters Patent is hereby corrected as shown below:

Column 1,
Lines 17-18, "the National Cancer Institute" should read --the National Institutes of Health--.

Signed and Sealed this
Twenty-second Day of May, 2012

David J. Kappos
*Director of the United States Patent and Trademark Office*

SEQUENCE LISTING

```
<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: pTyr-peptide
<220> FEATURE:
<221> NAME/KEY: MISC_FEATURE
<222> LOCATION: (3)..(3)
<223> OTHER INFORMATION: phosphorylation

<400> SEQUENCE: 1

Ala Pro Tyr Leu Lys Thr
1               5

<210> SEQ ID NO 2
<211> LENGTH: 9
<212> TYPE: PRT
<213> ORGANISM: Artificial Sequence
<220> FEATURE:
<223> OTHER INFORMATION: biotinylated conjugate pTyr-peptide
<220> FEATURE:
<221> NAME/KEY: MISC_FEATURE
```

```
<222> LOCATION: (4)..(4)
<223> OTHER INFORMATION: phosphorylation

<400> SEQUENCE: 2

Glu Pro Gln Tyr Glu Glu Ile Glu Leu
1               5

<210> SEQ ID NO 3
<211> LENGTH: 24
<212> TYPE: DNA
<213> ORGANISM: Artificial Sequence
<220> FEATURE:
<223> OTHER INFORMATION: hSIE oligonucleotide probe

<400> SEQUENCE: 3
agcttcattt cccgtaaatc ccta                                          24

<210> SEQ ID NO 4
<211> LENGTH: 18
<212> TYPE: DNA
<213> ORGANISM: Artificial Sequence
<220> FEATURE:
<223> OTHER INFORMATION: MGFe oligonucleotide probe

<400> SEQUENCE: 4
agatttctag gaattcaa                                                 18
```